(12) United States Patent
Feng et al.

(10) Patent No.: US 11,643,670 B2
(45) Date of Patent: May 9, 2023

(54) METHODS OF ENHANCING CHROMOSOMAL HOMOLOGOUS RECOMBINATION

(71) Applicant: Massachusetts Institute of Technology, Cambridge, MA (US)

(72) Inventors: Guoping Feng, Newton, MA (US); Jonathan Wilde, Cambridge, MA (US); Tomomi Aida, Arlington, MA (US); Martin Wienisch, Arlington, MA (US); Qiangge Zhang, Quincy, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 13 days.

(21) Appl. No.: 16/260,630

(22) Filed: Jan. 29, 2019

(65) Prior Publication Data
US 2019/0233846 A1  Aug. 1, 2019

Related U.S. Application Data

(60) Provisional application No. 62/673,473, filed on May 18, 2018, provisional application No. 62/623,006, filed on Jan. 29, 2018.

(51) Int. Cl.
| | |
|---|---|
| *C12N 15/90* | (2006.01) |
| *C12N 9/22* | (2006.01) |
| *C12N 15/113* | (2010.01) |
| *C12N 15/10* | (2006.01) |
| *A01K 67/027* | (2006.01) |
| *A61K 31/136* | (2006.01) |
| *A61K 35/54* | (2015.01) |
| *C12N 5/073* | (2010.01) |
| *C12N 15/877* | (2010.01) |

(52) U.S. Cl.
CPC ........ *C12N 15/907* (2013.01); *A01K 67/0275* (2013.01); *A61K 31/136* (2013.01); *A61K 35/54* (2013.01); *C12N 5/0603* (2013.01); *C12N 9/22* (2013.01); *C12N 15/102* (2013.01); *C12N 15/113* (2013.01); *C12N 15/8776* (2013.01); *C12N 2310/20* (2017.05); *C12Q 2521/301* (2013.01); *C12Y 301/21001* (2013.01)

(58) Field of Classification Search
CPC ...... C12N 15/907; C12N 5/0603; C12N 9/22; C12N 15/102; C12N 15/113; C12N 15/8776; C12N 2310/20; A01K 67/0275; A61K 31/136; A61K 35/54; C12Q 2521/301; C12Y 301/21001
See application file for complete search history.

(56) References Cited

U.S. PATENT DOCUMENTS

| | | | |
|---|---|---|---|
| 2012/0231449 A1* | 9/2012 | Mermod | C12N 15/85 435/6.1 |
| 2016/0101111 A1* | 4/2016 | Yen | A61K 2300/00 514/49 |

FOREIGN PATENT DOCUMENTS

| | | |
|---|---|---|
| WO | WO 2014/131833 A1 | 9/2014 |
| WO | WO 2015/088643 A1 | 6/2015 |
| WO | WO 2016/081923 A2 | 5/2016 |
| WO | WO-2017165826 A1 * | 9/2017 ........... C12N 15/111 |
| WO | WO-2018060238 A1 * | 4/2018 ........... C12N 15/102 |

OTHER PUBLICATIONS

Song, J., Yang, D., Xu, J. et al. 2016 RS-1 enhances CRISPR/Cas9- and TALEN-mediated knock-in efficiency. Nat Commun 7, 10548 (Year: 2016).*
Ma, Hong et al 2017 "Correction of a pathogenic gene mutation in human embryos", Nature, vol. 548, No. 7668, pp. 413-419 (Year: 2017).*
Brunner et al. 2019 CRISPR-induced double-strand breaks trigger recombination between homologous chromosome arms. Life Science Alliance 2(3) p. 1-11 (Year: 2019).*
Marsden et. al. 2016. The Tumor-Associated Variant RAD51 G151D Induces a Hyper-Recombination Phenotype. PLoS Genet 12(8): e1006208, p. 1-29 (Year: 2016).*
Ma et al. reply. 2018. Nature vol. 560, pp. E10-E230 (Year: 2018).*
Toth et al. Cpf1 nucleases demonstrate robust activity to induce DNA modification by exploiting homology directed repair pathways in mammalian cells. 2016 Biology Direct 11:46 (Year: 2016).*
Moynahan and Jasin. Loss of heterozygosity induced by a chromosomal doublestrand break. 1997. Proc. Natl. Acad. Sci. USA vol. 94, pp. 8988-8993 (Year: 1997).*
Vispe et al. Overexpression of Rad51 protein stimulates homologous recombination and increases resistance of mammalian cells to ionizing radiation. 1988 Nucleic Acids Research, vol. 26, No. 12 (Year: 1988).*

(Continued)

*Primary Examiner* — Samuel C Woolwine
*Assistant Examiner* — Tiffany Nicole Grooms
(74) *Attorney, Agent, or Firm* — Wolf, Greenfield & Sacks, P.C.

(57) ABSTRACT

Described herein are methods of enhancing chromosomal homologous recombination to stimulate a loss of heterozygosity at a gene locus of interest in a living cell. These methods are driven by an enhancer component and a target-specific endonuclease component and proceed through a mechanism whereby: exogenous donor DNA that is homologous to the gene locus of interest is not introduced into the living cell; the desired allele of the gene locus of interest remains uncleaved; and the undesired allele is either uncleaved, cleaved at a single location, or cleaved at multiple locations. These methods have numerous applications, including the repair of risk alleles for disease prevention, the correction of heterozygous mutations in dividing cells, the design of cancer therapeutics, and the design of novel gene-drive strategies.

24 Claims, 18 Drawing Sheets

Specification includes a Sequence Listing.

(56) References Cited

OTHER PUBLICATIONS

Pohl et al. Rad51-Independent Interchromosomal Double-Strand Break Repair by Gene Conversion Requires Rad52 but Not Rad55, Rad57, or Dmc1 Molecular and Cellular Biology, Feb. 2008, p. 897-906 (Year: 2008).*
[No Author Listed], Gene Drives on the Horizon: Advancing Science, Navigating Uncertainty, and Aligning Research with Public Values. National Academies Press (US). 2016:C1-217.
Abkevich et al., Patterns of genomic loss of heterozygosity predict homologous recombination repair defects in epithelial ovarian cancer. British J Cancer. 2012;107:1776-82.
Aida et al., Cloning-free CRISPR/Cas system facilitates functional cassette knock-in in mice. Genome Biol. Apr. 29, 2015; 16: 87.
Aida et al., Gene cassette knock-in in mammalian cells and zygotes by enhanced MMEJ. BMC Genomics. Nov. 28, 2016; 17(1): 979.
Canny et al., Inhibition of 53BP1 Favors Homology-Dependent DNA Repair and Increases CRISPR-Cas9 Genome-Editing Efficiency. Nat Biotechnol. Jan. 2018;36(1):95-102. doi: 10.1038/nbt.4021. Epub Nov. 27, 2017.
Chen et al., Tumor-associated mutations in a conserved structural motif alter physical and biochemical properties of human RAD51 recombinase. Nucleic Acids Res. Jan. 2015; 43(2): 1098-111.
Cheung et al., Recent insights into the molecular basis of Fanconi anemia: genes, modifiers, and drivers. Int J Hematol. 2017;106:335-44.
Chia et al., Genomic instability during reprogramming by nuclear transfer is DNA replication dependent. Nat Cell Biol. Apr. 2017;19(4):282-93. Supplementary Information: 1-6. 18 pages.
Christie et al., Towards personalised allele-specific CRISPR gene editing to treat autosomal disorders. Sci Reports. Nov. 23, 2017;7:16174, 12 pages.
Cohn et al., A UAF1-Containing Multisubunit Protein Complex Regulates the Fanconi Anemia Pathway. Mol Cell. Dec. 14, 2007;26:766-97.
Critchlow et al., Mammalian DNA double-strand break repair protein XRCC4 interacts with DNA ligase IV. Curr. Biol. Aug. 1, 1997; 7(8): 588-98.
Deng et al., Single-cell RNA-seq reveals dynamic, random monoallelic gene expression in mammalian cells. Science. Jan. 10, 2014; 343(6167): 193-96.
Dutta et al., Microhomology-mediated end joining is activated in irradiated human cells due to phosphorylation-dependent formation of the XRCC1 repair complex. Nucleic Acids Res. Mar. 17, 2017; 45(5): 2585-99.
Egli et al., Inter-homologue repair in fertilized human eggs? bioRxiv. Aug. 28, 2017; doi:10.1101/181255.
Gaudelli et al., Programmable Base Editing of A-T to G-C in Genomic DNA Without DNA Cleavage. Nature. Nov. 23, 2017;551(7681):464-71.
Hashimoto et al., Mechanisms of interstrand DNA crosslink repair and human disorders. Genes Environ. 2016;38(9):1-8.
Jinek et al., A Programmable Dual-RNA-Guided DNA Endonuclease in Adaptive Bacterial Immunity. Sci. Aug. 17, 2012;337(6096):816-21.
Kelso et al., The ?-isoform of BCCIP promotes ADP release from the RAD51 presynaptic filament and enhances homologous DNA pairing. Nucleic Acids Res. Jan. 25, 2017; 45(2): 711-25.
Komor et al., Programmable editing of a target base in genomic DNA without double-stranded DNA cleavage. Nature. May 19, 2016;533(7603):420-24.
Ladstatter et al., A Surveillance Mechanism Ensures Repair of DNA Lesions during Zygotic Reprogramming. Cell. Dec. 15, 2016; 167(7): 1774-87.
Li et al., Small molecules enhance CRISPR/Cas9-mediated homology-directed genome editing in primary cells. Sci Rep. Aug. 21, 2007; 7(1): 8943.
Lin et al., Genome dynamics of the human embryonic kidney 293 lineage in response to cell biology manipulations. Nat. Commun. Sep. 3, 2014; 5:4767.
Liu et al., Homozygous defect in HIV-1 coreceptor accounts for resistance of some multiply-exposed individuals to HIV-1 infection. Cell. Aug. 9, 1996; 86(3):367-77.
Lu et al., The BRCA2-Interacting Protein BCCIP Functions in RAD51 and BRCA2 Focus Formation and Homologous Recombinational Repair. Mol. Cell Biol. May 2005; 25(5): 1949-57.
Ma et al., Correction of a pathogenic gene mutation in human embryos. Nature. Aug. 24, 2017; 548(7668): 413-9.
Ma et al., CRISPR/Cas9-mediated gene manipulation to create single-amino-acid-substituted and Boxed mice with a cloning-free method. Sci. Rep. Feb. 8, 2017; 7: 42244.
Macias et al., Gene Drive for Mosquito Control: Where Did It Come from and Where Are We Headed? Int J Environ Res Public Health. Sep. 2, 2017;14(9):ppi: E1006.
Malik et al., Rad51 Gain-Of-Function Mutants That Exhibit High Affinity DNA Binding Cause DNA Damage Sensitivity in the Absence of Srs2. Nucleic Acids Res. Nov. 2008; 36(20): 6504-10.
Marsden et al., The Tumor-Associated Variant RAD51 G151D Induces a Hyper-Recombination Phenotype. PLoS Genet. Aug. 11, 2016; 12(8): e1006208.
Maruyama et al., Increasing the efficiency of precise genome editing with CRISPR-Cas9 by inhibition of nonhomologous end joining. Nat Biotechnol. May 2015; 33(5): 538-42.
Mcvey et al., MMEJ repair of double-strand breaks (director's cut): deleted sequences and alternative endings. Trends Genet. Nov. 2008; 24(11): 529-38.
Moldovan et al., How the Fanconi anemia pathway guards the genome. Annu. Rev. Genet. 2009; 43: 223 49.
Monteys et al., CRISPR/Cas9 editing of the mutant huntingtin allele in vitro and in vivo. Mol Ther. Jan. 2017;25(1):12-23.
Moynahan et al., Loss of heterozygosity induced by a chromosomal double-strand break. Proc. Natl. Acad. Sci. U.S.A. Aug. 19, 1997; 94(17): 8988-93.
Murai et al., The USP1/UAF1 complex promotes double-strand break repair through homologous recombination. Mol. Cell Biol. Jun. 2011; 31(12): 2462-69.
Nishida et al., Targeted nucleotide editing using hybrid prokaryotic and vertebrate adaptive immune systems. Science. Sep. 16, 2016; 353(6305); aaf8729-aaf8729.
Normanno et al., Mutational phospho-mimicry reveals a regulatory role for the XRCC4 and XLF C-terminal tails in modulating DNA bridging during classical non-homologous end joining. Elife. May 13, 2017; 6.
Paquet et al., Efficient introduction of specific homozygous and heterozygous mutations using CRISPR/Cas9. Nature. May 5, 2016; 533(7601): 125-9.
Prakash et al., Homologous recombination and human health: the roles of BRCA1, BRCA2, and associated proteins. Cold Spring Harbor Perspectives in Biology. 2015:1-28.
Qi et al., HEK293T Cells are Heterozygous for CCR5 Delta 32 Mutation. PLoS One. Apr. 4, 2016; 11(4): e0152975.
Quadros et al., Easi-CRISPR: a robust method for one-step generation of mice carrying conditional and insertion alleles using long ssDNA donors and CRISPR ribonucleoproteins. Genome Biol. May 17, 2017; 18(1): 92.
Ran et al., Double Nicking by RNA-guided CRISPR Cas9 for Enhanced Genome Editing Specificity. Cell. Sep. 12, 2013;154(6):1380-9. doi: 10.1016/j.cell.2013.08.021. Epub Aug. 29, 2013.
Richardson et al., Double-strand break repair by interchromosomal recombination: suppression of chromosomal translocations. Genes Dev. Dec. 15, 1998; 12(24): 3831-42.
Rohn et al., The potential of CRISPR/Cas9 Gene editing as a treatment strategy for Alzheimer's disease. J Alzheimers Dis Parkinsonism. 2018;8(3):1-12.
Sehorn et al., Human meiotic recombinase Dmc1 promotes ATP-dependent homologous DNA strand exchange. Nature. May 27, 2004; 429(6990): 433-37.
Shin et al., CRISPR/Cas9 targeting events cause complex deletions and insertions at 17 sites in the mouse genome. Nat. Commun. May 31, 2017; 8: 15464.

(56) References Cited

OTHER PUBLICATIONS

Sinkins et al., Gene Drive Systems for Insect Disease Vectors. Nat Rev Genet. Jun. 2006;7(6):427-35. doi: 10.1038/nrg1870.
Song et al., RS-1 enhances CRISPR/Cas9- and TALEN-mediated knock-in efficiency. Nat. Commun. Jan. 28, 2016; 10548.
Stark et al., Extensive loss of heterozygosity is suppressed during homologous repair of chromosomal breaks. Mol. Cell Biol. Jan. 2003; 23(2): 733-43.
Takayama et al., Highly efficient biallelic genome editing of human ES/iPS cells using a CRISPR/Cas9 or TALEN system. Nucleic Acids Res. May 19, 2017; 45(9): 5198-207.
Taylor et al., A cell cycle-specific requirement for the XRCC1 Brct II domain during mammalian DNA strand break repair. Mol. Cell Biol. Jan. 2000; 20(2): 735-40.
Wesoly et al., Differential Contributions of Mammalian Rad54 Paralogs to Recombination, DNA Damage Repair, and Meiosis. Mol Cell Biol. Feb. 2006;26(3):976-89.
Wilde et al., Efficient Zygotic Genome Editing via RAD51-Enhanced Interhomolog Repair. bioRxiv. Aug. 6, 2018. 39 pages.
Wilde et al., RAD51 Enhances Zygotic Interhomolog Repair. bioRxiv. Jul. 11, 2018. 17 pages.
Wray et al., Distinct RAD51 Associations with RAD52 and BCCIP in Response to DNA Damage and Replication Stress. Cancer Res. Apr. 15, 2008; 68(8): 2699-707.
Wu et al., Correction of a genetic disease in mouse via use of CRISPR-Cas9. Cell Stem Cell. Dec. 5, 2013; 13(6): 659-62.
Xu et al., Translation of CRISPR Genome surgery to the bedside for retinal diseases. Frontiers Cell Devel Biol. May 23, 2016;6(48):1-6.
Yu et al., Dynamic control of Rad51 recombinase by self-association and interaction with BRCA2. Mol. Cell. Oct. 2003; 12(4): 1029 41.
Yu et al., Small molecules enhance CRISPR genome editing in pluripotent stem cells. Cell Stem Cell. Feb. 5, 2015; 16(2): 142-7.
Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.
PCT/US2019/015577, Apr. 11, 2019, International Search Report and Written Opinion.
[No Author Listed] Study identifies pitfall in correcting mutations in human embryos with CRISPR. Science Daily. Oct. 29, 2020;2 pages. https://www.sciencedaily.com/releases/2020/10/201029142001.htm [last accessed Jan. 20, 2021].
Adikusuma et al., Large deletions induced by Cas9 cleavage. Nature. Aug. 2018;560(7717):E8-E9. doi: 10.1038/s41586-018-0380-z. Epub Aug. 8, 2018.
Alanis-Lobato et al., Frequent loss-of-heterozygosity in CRISPR-Cas9-edited early human embryos. bioRxiv. Jun. 5, 2020;135913:14 pages, doi: 10.1101/2020.06.05.135913. Epub Oct. 31, 2020.
Callaway E., Doubts raised about gene-editing study in human embryos. Scientific American. Sep. 1, 2017;6 pages. https://www.scientificamerican.com/article/doubts-raised-about-gene-editing-study-in-human-embryos/ [last accessed Jan. 20, 2021].
Kosicki et al., Repair of double-strand breaks induced by CRISPR-Cas9 leads to large deletions and complex rearrangements. Nat Biotechnol. Sep. 2018;36(8):10 pages. doi: 10.1038/nbt.4192. Epub Jul. 16, 2018.
Larocque et al., Interhomolog recombination and loss of heterozygosity in wild-type and Bloom syndrome helicase (BLM)-deficient mammalian cells. Proc Natl Acad Sci USA. Jul. 19, 2011;108(29):11971-6. doi: 10.1073/pnas.1104421108. Epub Jul. 5, 2011.
Ledford H., Crispr gene editing in human embryos wreaks chromosomal mayhem. Nature. Jul. 2020;583(7814):5 pages. https://www.nature.com/articles/d41586-020-01906-4 [last accessed. Jan. 20, 2021].
Liang et al., Frequent gene conversion in human embryos induced by double strand breaks. bioRxiv. Jun. 19, 2020;162214:54 pages; doi: 10.1101/2020.06.19.162214. Epub Jun. 20, 2020.
Prakash et al., Distinct pathways of homologous recombination controlled by the SWS1-SWSAP1-SPIDR complex. bioRxiv. May 15, 2020;098848:33 pages, doi: 10.1101/2020.05.15.098848.
Zuccaro et al., Allele-Specific Chromosome Removal after Cas9 Cleavage in Human Embryos. Cell. Dec. 10, 2020;183(6):31 pages. doi: 10.1016/j.cell.2020.10.025. Epub Oct. 29, 2020.
Huang et al., Single-Cell Whole-Genome Amplification and Sequencing: Methodology and Applications. Annu Rev Genomics Hum Genet. 2015;16:79-102. doi: 10.1146/annurev-genom-090413-025352. Epub Jun. 12, 2015.
Lao et al., Meiotic crossover control by concerted action of Rad51-Dmc1 in homolog template bias and robust homeostatic regulation. PLoS Genet. 2013;9(12):e1003978. doi: 10.1371/journal.pgen.1003978. Epub Dec. 19, 2013.
Palmerola et al., Replication stress impairs chromosome segregation and preimplantation development in human embryos. Cell. Aug. 4, 2022;185(16):2988-3007.e20. doi: 10.1016/j.cell.2022.06.028. Epub Jul. 19, 2022.
Rouet et al., Expression of a site-specific endonuclease stimulates homologous recombination in mammalian cells. Proc Natl Acad Sci USA. Jun. 21, 1994;91(13):6064-8.

* cited by examiner

FIG. 1A
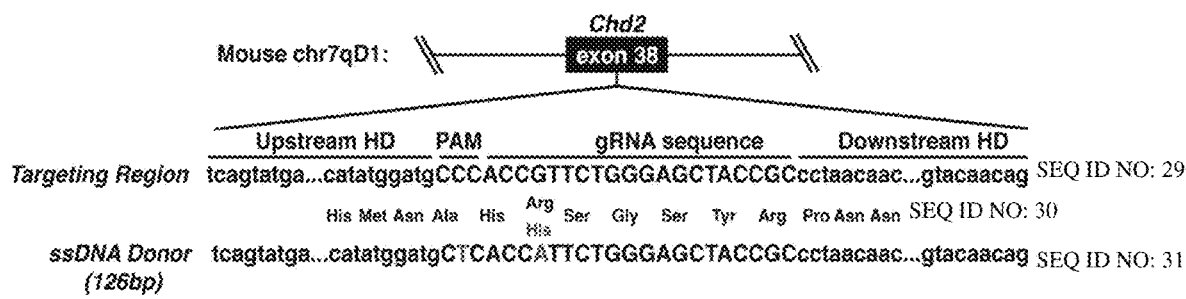
FIG. 1B
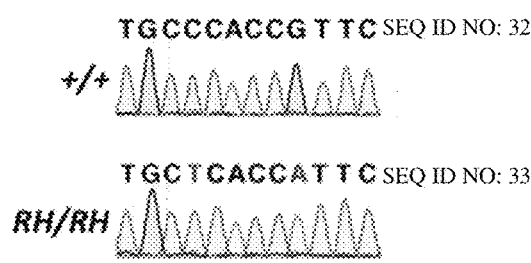
FIG. 1C
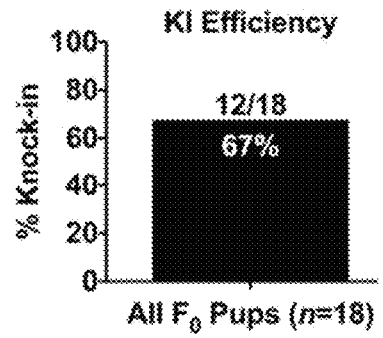
FIG. 1D
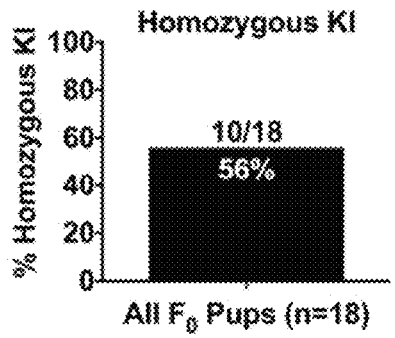
FIG. 1E

FIG. 3C
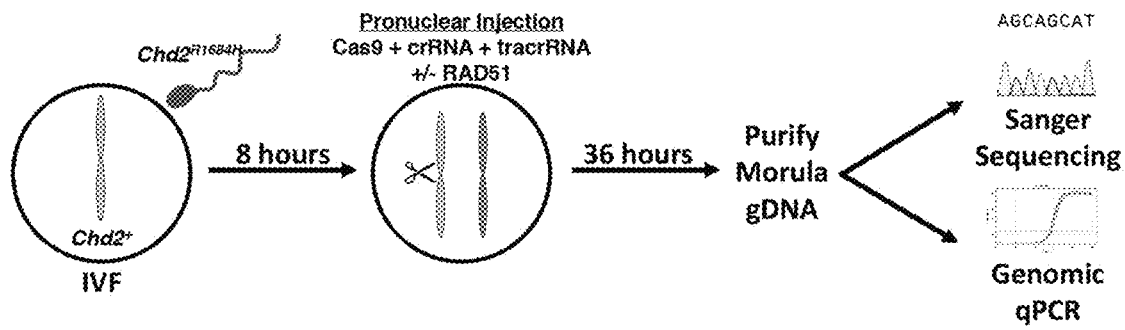
FIG. 3D
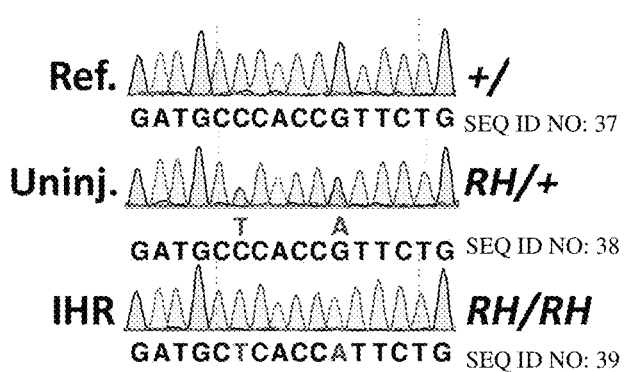
FIG. 3E
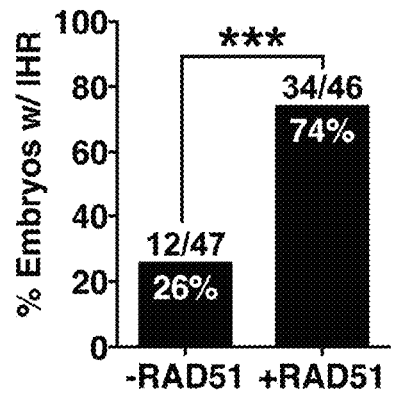
FIG. 3F
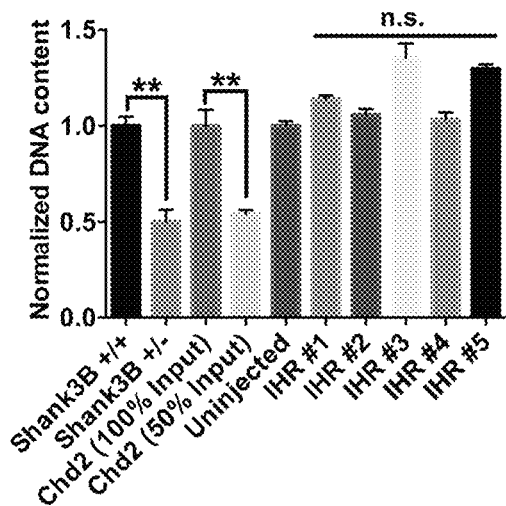
FIG. 3G
| Father ID (Genotype) | Mother ID (Genotype) | F₁ Het Pups |
|---|---|---|
| C57BL/6N (+/+) | 9162 (RH/RH) | 3/3 |
| 9164 (RH/RH) | C57BL/6N (+/+) | 7/7 |
| 9165 (RH/RH) | C57BL/6N (+/+) | 7/7 |
| C57BL/6N (+/+) | 9168 (RH/RH) | 4/4 |
| C57BL/6N (+/+) | 9170 (RH/RH) | 6/6 |

FIG. 4A
| Embryo | Cell 1 Genotype | Cell 2 Genotype |
|---|---|---|
| 1 | RH/RH | RH/RH |
| 2 | RH/Indel | RH/+ |
| 3 | RH/RH | RH/+ |
| 4 | RH/+ | RH/RH |
| 5 | RH/RH | RH/RH |
| 6 | RH/Indel | RH/Indel |
| 7 | RH/Indel | RH/+ |
| 8 | RH/+ | RH/RH |
| 9 | RH/Indel | RH/Indel |
| 10 | RH/Indel | RH/RH |
FIG. 4B
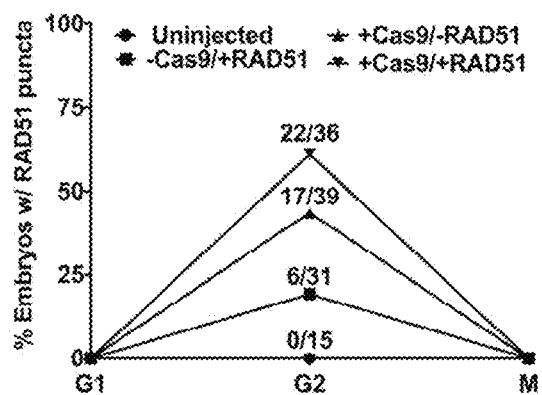
FIG. 4C
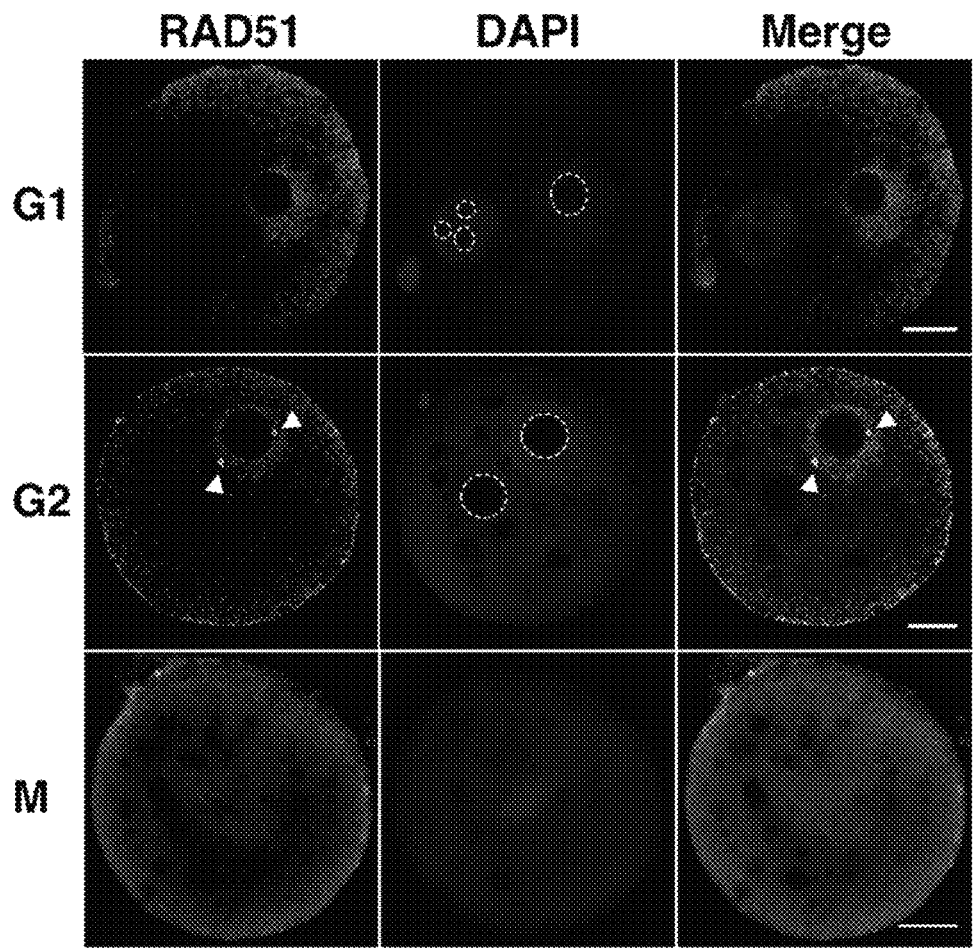

FIG. 10A
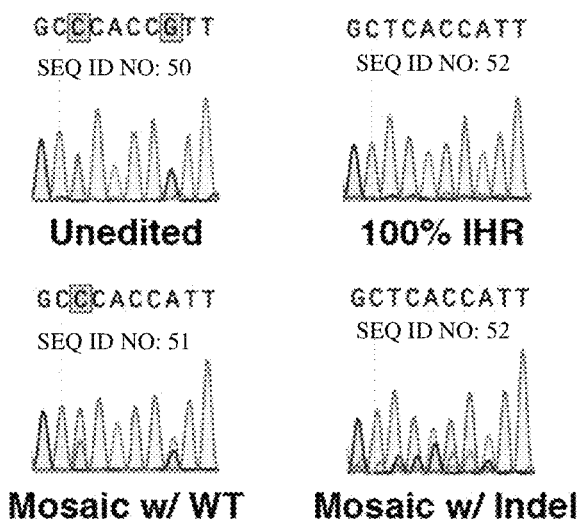
FIG. 10B
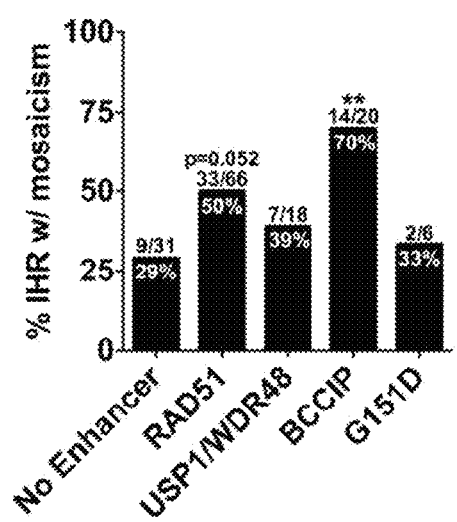
FIG. 10C
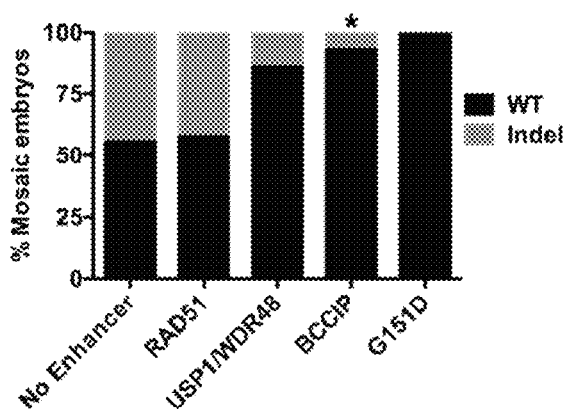
FIG. 10D
| Condition | # Mosaic w/ WT | # Mosaic w/ Indel |
|---|---|---|
| No Enhancer | 5 | 4 |
| RAD51 | 19 | 14 |
| Rad51 mRNA | 0 | 4 |
| T131P | 1 | 0 |
| G151D | 2 | 0 |
| SA208-209ED | 3 | 5 |
| USP1/WDR48 | 6 | 1 |
| BCCIP | 13 | 1 |
| XRCC1 | 1 | 0 |
| XRCC4 | 0 | 3 |
| DMC1 | 5 | 0 |

Embryo genotyping

| Target | # Embryos | KI (%) |
|---|---|---|
| Cas9-D10X | 10 | 4 (40) |
| EGFP-I188X | 10 | 4 (40) |

Newborn genotyping

| Target | # newborns | KI (%) |
|---|---|---|
| Cas9-D10X | 5 | 2 (40) |
| EGFP-I188X | 13 | 6 (46) |

METHODS OF ENHANCING CHROMOSOMAL HOMOLOGOUS RECOMBINATION

RELATED APPLICATIONS

This application claims priority under 35 U.S.C. § 119(e) to U.S. provisional application No. 62/673,473, filed May 18, 2018, and U.S. provisional application No. 62/623,006, filed Jan. 29, 2018, the entire contents of which are incorporated herein by reference.

FIELD

Described herein are methods of enhancing chromosomal homologous recombination to stimulate a loss of heterozygosity at a gene locus of interest in a living cell.

BACKGROUND

Previously published data from human embryos reported a zygotic interchromosomal homologous recombination mechanism whereby one allele can serve as the repair template for the other after induction of a double-strand break (DSB) by Cas9 (Ma H., et al. Nature. 2017 Aug. 24; 548(7668): 413-19). While a few studies have reported evidence of interchromosomal homologous recombination events in experiments using mouse ES cells (Moynahan M. E. and Jasin M., Proc. Natl. Acad. Sci. U.S.A. 1997 Aug. 19; 94(17): 8988-93; Richardson C., et al., Genes Dev. 1998 Dec. 15; 12(24): 3831-42), others have disputed the findings of interchromosomal homologous recombination in human embryos (Egli D., et al., bioRxiv. 2017 Aug. 28; doi: 10.1101/181255), arguing: that inter-homologue repair requires physical interaction of the maternal and paternal genomes which does not occur until long after the induction of a DSB by Cas9; that karyotyping data support the possibility of parthenogenesis in some of the edited embryos that could lead to false positive results; and that a significant source of the observed homozygosity comes from large deletions at the DSB site that remove one or both binding sites for genotyping primers. Thus, the potential mechanism of interchromosomal homologous recombination has remained controversial and the development of interchromosomal homologous recombination technologies has remained largely unexplored.

SUMMARY

Described herein are methods of enhancing chromosomal homologous recombination (CHR) to stimulate a loss of heterozygosity at a gene locus of interest in a living cell. These methods provide conclusive evidence supporting the previous controversial finding of interchromosomal homologous recombination in human embryos (Ma H., et al. Nature. 2017 Aug. 24; 548(7668): 413-19; Egli D., et al., bioRxiv. 2017 Aug. 28; doi:10.1101/181255).

These methods are driven by an enhancer component and a target-specific endonuclease component and can proceed through a mechanism whereby: exogenous donor DNA that is homologous to the gene locus of interest is not introduced into the living cell; the desired allele of the gene locus of interest remains uncleaved; and the undesired allele is either uncleaved, cleaved at a single location, or cleaved at multiple locations. These methods have numerous applications, including the repair of risk alleles for disease prevention, the correction of heterozygous mutations in living cells, cancer therapeutics, and novel gene-drive strategies.

In some aspects, the disclosure relates to a method of stimulating a loss of heterozygosity at a gene locus of interest in a living cell. In some embodiments, the method comprises: identifying at least one gene locus of interest in a living cell, wherein each of the at least one gene locus of interest comprises a desired allele and an undesired allele; and introducing an enzymatic unit into the living cell, wherein the enzymatic unit cleaves the undesired allele of each of the at least one gene locus of interest and enhances chromosomal homologous recombination between the desired allele and the undesired allele of each of the at least one gene locus of interest and wherein the enzymatic unit comprises at least one enhancer component and at least one target-specific endonuclease component; and wherein: each of the at least one enhancer component is selected from the group consisting of a Rad51, Rad51 G151D, Rad52, Rad54, BRCA1, BRCA2, PALB2, XRCC1, XRCC4, USP1, WDR48, DMC1, BCCIP, BLM, C19ORF40, EME1, EME2, FANCA, FANCB, FANCC, FANCD2, FANCE, FANCF, FANCG, FANC1, FANCL, MRE11A, MSH4, MSH5, and MUS81 component; the undesired allele of each of the at least one gene locus of interest is cleaved only once; the desired allele of each of the at least one gene locus of interest remains uncleaved; the chromosomal homologous recombination generates homozygosity at each of the at least one gene locus of interest, wherein each of the at least one gene of interest comprises two desired alleles after chromosomal homologous recombination; and exogenous donor DNA is not introduced into the living cell, wherein the exogenous donor DNA comprises at least one polynucleic sequence that is homologous to at least one of the at least one gene locus of interest.

In some embodiments, the enzymatic unit cleaves the undesired allele of at least one of the at least one gene locus of interest through the introduction of a single-strand break. In some embodiments, the enzymatic unit cleaves the undesired allele of at least one of the at least one gene locus of interest through the introduction of a double-strand break. In some embodiments, the enzymatic unit cleaves at least two undesired alleles, and at least one of the at least two undesired alleles is cleaved through the introduction of a single-strand break and at least one of the at least two undesired alleles is cleaved through the introduction of a double-strand break.

In some embodiments, the method comprises: identifying at least one gene locus of interest in a living cell, wherein each of the at least one gene locus of interest comprises a desired allele and an undesired allele, and introducing an enzymatic unit into the living cell, wherein the enzymatic unit enhances chromosomal homologous recombination between the desired allele and the undesired allele of each of the at least one gene locus of interest and lacks the ability to cleave DNA and wherein the enzymatic unit comprises at least one enhancer component; and at least one target-specific endonuclease component; and wherein: each of the at least one enhancer component is selected from the group consisting of a Rad51, Rad51 G151D, Rad52, Rad54, BRCA1, BRCA2, PALB2, XRCC1, XRCC4, USP1, WDR48, DMC1, BCCIP, BLM, C19ORF40, EME1, EME2, FANCA, FANCB, FANCC, FANCD2, FANCE, FANCF, FANCG, FANC1, FANCL, MRE11A, MSH4, MSH5, and MUS81 component; the at least one target-specific endonuclease component specifically binds to the undesired allele of at least one of the at least one gene locus of interest; the chromosomal homologous recombination generates homozygosity at each of the at least one gene locus of interest, wherein each of the at least one gene of interest comprises two desired alleles after chromosomal homologous recombination; and exogenous donor DNA is not introduced into the living cell, wherein the exogenous donor DNA comprises at least one polynucleic sequence that is homologous to at least one of the at least one gene locus of interest.

In some embodiments, at least one of the at least one enhancer component comprises a polynucleic acid that encodes for a polypeptide sequence that comprises the polypeptide sequence of Rad51, Rad51 G151D, Rad52, Rad54, BRCA1, BRCA2, PALB2, XRCC1, XRCC4, USP1, WDR48, DMC1, BCCIP, BLM, C19ORF40, EME1, EME2, FANCA, FANCB, FANCC, FANCD2, FANCE, FANCF, FANCG, FANC1, FANCL, MRE11A, MSH4, MSH5, or MUS81. In some embodiments, at least one of the at least one enhancer component comprises a polypeptide that comprises the polypeptide sequence of Rad51, Rad51 G151D, Rad52, Rad54, BRCA1, BRCA2, PALB2, XRCC1, XRCC4, USP1, WDR48, DMC1, BCCIP, BLM, C19ORF40, EME1, EME2, FANCA, FANCB, FANCC, FANCD2, FANCE, FANCF, FANCG, FANC1, FANCL, MRE11A, MSH4, MSH5, or MUS81.

In some embodiments, at least one of the at least one enhancer component is a Rad51, Rad51 G151D, or BCCIP component. In some embodiments, the Rad51, Rad51 G151D, or BCCIP component comprises a polynucleic acid sequence that encodes for a polypeptide sequence that comprises the polypeptide sequence of Rad51, Rad51 G151D, or BCCIP, respectively. In some embodiments, the Rad51, Rad51 G151D, or BCCIP component comprises a polypeptide sequence that comprises the polypeptide sequence of Rad51, Rad51 G151D, or BCCIP, respectively. In some embodiments, the Rad51 component comprises a small molecule that enhances homologous directed repair. In some embodiments, the small molecule is RS-1.

In some embodiments, at least one of the at least one target-specific endonuclease component comprises a polynucleic acid that encodes for a polypeptide sequence that comprises the polypeptide sequence of a target-specific endonuclease. In some embodiments, at least one of the at least one target-specific endonuclease component comprises a polypeptide that comprises the polypeptide sequence of a target-specific endonuclease.

In some embodiments, the polypeptide sequence that comprises the sequence of a target-specific endonuclease comprises the polypeptide sequence of an RNA-dependent endonuclease. In some embodiments, the RNA-dependent endonuclease is a CRISPR/Cas protein. In some embodiments, the enzymatic unit further comprises at least one crRNA, at least one tracrRNA, and/or at least one sgRNA. In some embodiments, the CRISPR/Cas protein is Cas9. In some embodiments, the CRISPR/Cas protein is a mutated CRISPR/Cas protein, wherein the mutated CRISPR/Cas protein comprises a mutated nuclease domain and wherein the mutated CRISPR/Cas protein generates single-strand breaks.

In some embodiments, the polypeptide sequence that comprises the sequence of a target-specific endonuclease comprise the polypeptide sequence of an RNA-independent endonuclease. In some embodiments, the RNA-independent endonuclease is selected from the group consisting of a meganuclease, a zinc-finger nuclease, a transcription activator-like effector nuclease, and a restriction enzyme. In some embodiments, the RNA-independent endonuclease is a restriction enzyme, wherein the restriction enzyme is a site-specific DNA-nicking enzyme.

In some embodiments, the loss of heterozygosity is enhanced by at least 20% relative to the loss of heterozygosity in the absence of the at least one enhancer component. In some embodiments, the loss of heterozygosity is enhanced by at least 100% relative to the loss of heterozygosity in the absence of the at least one enhancer component. In some embodiment, the enhancer component stimulates essentially error-free chromosomal homologous recombination. In some embodiments, the enhancer component stimulates error-free chromosomal homologous recombination.

In some embodiments, the living cell is a cell of a multicellular organism, wherein the multicellular organism is administered a composition comprising: the at least one enhancer component; the at least one target-specific endonuclease component; and optionally a cellular delivery component. In some embodiments, the multicellular organism comprises multiple cell types. In some embodiments, the multicellular organism is an animal. In some embodiments, the animal is a human patient suffering from a disease, wherein the disease is caused by heterozygosity at at least one gene locus of interest. In some embodiments, the multicellular organism is an insect. In some embodiments, the multicellular organism is a plant.

In some embodiments, the living cell is a unicellular organism. In some embodiments, the unicellular organism is a bacteria.

In some embodiments, the living cell is a cell of a genetically engineered transgenic organism and wherein at least one of the at least one gene locus of interest comprises a transgenic gene locus, wherein the desired allele of the transgenic gene locus is a transgenic payload gene and the undesired allele of the transgenic gene locus is an endogenous sequence.

In some aspects, the disclosure relates to a therapeutic composition for use in a method of treating a medical condition caused by heterozygosity at an allele of a gene of interest comprising administering to a patient a composition comprising: the at least one enhancer component; the at least one target-specific endonuclease component; and optionally a cellular delivery component. In some embodiments, the medical condition is an autosomal dominant disorder. In some embodiments, the medical condition is caused by codominance or incomplete dominance.

In some aspects, the disclosure relates to a therapeutic composition for use in a method of preventing a medical condition caused by homozygosity at an allele of a gene of interest comprising administering to a patient a composition comprising: the at least one enhancer component; the at least one target-specific endonuclease component; and optionally a cellular delivery component. In some embodiments, the medical condition is caused by an autosomal recessive disorder.

In some aspects, the disclosure relates to interchromosomal homologous recombination/repair (ICHR) reporter animals that facilitate visualization/identification of ICHR in vivo. In some embodiments, the genome of the reporter animal comprises at least one pair of exogenous nucleic acid sequences, wherein: the exogenous nucleic acid sequences in the pair are homologous; each of the exogenous nucleic acid sequences in the pair comprises a reporter gene; and ICHR between the exogenous nucleic acid sequences in the pair results in activation of the reporter gene of at least one of the exogenous nucleic acids in the pair. As used herein, "activation of a reporter gene" may relate to increased transcription of at least one reporter gene. For example, in some embodiments, no mRNA of either reporter is produced in the absence of ICHR. "Activation of a reporter gene" may also relate to increased translation of at least one reporter gene. For example, in some embodiments, no protein of either reporter gene is produced in the absence of ICHR. In some embodiments, the ICHR reporter animal is a single cell. In other embodiments, the ICHR reporter animal is a multicellular organism. In some embodiments, the ICHR reporter animal is as described in Example 11.

In some aspects, the disclosure relates to the use of an ICHR reporter animal described herein. In some embodiments, the ICHR reporter animal is used to evaluate: enhancers of ICHR; ICHR dynamics; and/or ICHR mosaicism. In some embodiments, the ICHR reporter animal is used for genome-wide CRISPR screening.

These and other aspects of the invention are further described below.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIGS. 1A-1E. Efficient homozygous knock-in with RAD51. FIG. 1A. Schematic of the targeting locus and homologous recombination (HR) donor for generating $Chd2^{R1684H}$ mutant mice. HR donor contains both the c.5051G>A point mutation and a synonymous mutation that ablates the relevant PAM site (HD=homology domain). FIG. 1B. Example chromatograms of wildtype (top) and $Chd2^{R1684H/R1684H}$ animals (RH=R1684H). FIG. 1C. Overall knock-in (KI) efficiency observed in $F_0$ pups (pups with ≥1 KI allele/total pups). FIG. 1D. Homozygous KI rate observed in $F_0$ pups. FIG. 1E. Genotyping results from $F_1$ pups derived from crosses between $F_0$ $Chd2^{R1684H/R1684H}$ animals and wildtype C57BL/6N animals.

FIG. 2A. Quantification of KI efficiency (left) and homozygous KI efficiency in embryos generated by $Chd2^{R1684H}$ PNI using 30 ng/μL ssODN with or without RAD51 (KI: p=0.034, one-tailed chi-square test; homo KI: p<0.0001, one-tailed chi-square test). FIG. 2B. Schematic of knock-in strategy for the albinism-associated $Tyr^{C89S}$ mutation. FIG. 2C. Representative examples of $Tyr^{+/+}$ (black) and $Tyr^{C89S/C89S}$ (white) littermates derived from three-component CRISPR injections using exogenous RAD51 protein. FIG. 2D. Representative chromatograms from $Tyr^{+/+}$ (top) and $Tyr^{C89S/C89S}$ animals. FIG. 2E. Genotyping of $F_0$ animals generated by three-component CRISPR targeting the $Tyr^{C89S}$ locus with or without RAD51 (KI: n.s.=not significant, p=0.166, one-tailed chi-square test; Homo KI: p=0.0081, one-tailed chi-square test).

FIGS. 3A-3F. RAD51 enhances interchromosomal homologous recombination. FIG. 3A. Schematic of strategy to test homozygous KI mechanism. Fertilized embryos were injected with Cas9 protein, crRNA, tracrRNA, and an equimolar mixture of two ssODNs varying by two nucleotides with or without RAD51 protein. FIG. 3B. Genotyping results from embryos collected following mixed ssODN injection. Homozygous KI efficiency represents the fraction of homozygous KI events observed in all injected embryos (p=0.0008, one-tailed chi-square test). Compound heterozygous rates represent the fraction of homozygous KI embryos with a different KI event on each allele (p=0.0120, two-tailed chi-square test). FIG. 3C. Schematic of strategy for testing RAD51-enhanced interchromosomal homologous recombination. Wildtype C57BL/6N eggs were fertilized in vitro by sperm collected from male $Chd2^{R1684H/R1684H}$ mice and cultured for 8 hours. At 8hpf, the PNI was performed with Cas9 protein, crRNA, and tracrRNA with or without RAD51 protein. Since R1684H mutants carry a mutation in the PAM associated with the crRNA utilized in these experiments, Cas9 is only capable of cutting the maternal allele. Injected embryos were then cultured for 48 hours and collected at morula stage. Half of the purified DNA was used for nested PCR and Sanger sequencing and the other half was used for multiplex PCR and subsequent qPCR to analyze genomic copy number at the Chd2 editing locus. FIG. 3D. Representative chromatograms showing the wildtype reference sequence (Ref., top), an uninjected $Chd2^{R1684H/+}$ embryo generated by IVF (Uninj., middle), and a $Chd2^{R1684H/R1684H}$ homozygous mutant (ICHR, bottom) generated via donor-free, RAD51-enhanced three-component CRISPR. FIG. 3E. Quantification of Sanger sequencing results from IVF-derived embryos co-injected with or without RAD51 (one-tailed chi-square test). FIG. 3F. Genomic qPCR targeting Shank3B using 180 pg genomic DNA from wildtype and Shank3B$^{+/-}$ mice as a control for copy-number sensitivity (lanes 1-2, p=0.00295, unpaired t-test, t=6.47, df=4, n=3 technical replicates per sample, error bars=SEM). Lanes 3-4 illustrate genomic qPCR for the $Chd2^{R1684H}$ locus using 100% and 50% input of DNA derived from wildtype blastocysts for Chd2 quantification (but 100% input for Gapdh) as a control for copy-number sensitivity at the locus (p=0.0099, unpaired t-test, t=5.355, df=3.302, n=4 technical replicates per condition, error bars=SEM). Lanes 5-10 illustrate genomic qPCR for the $Chd2^{R1684H}$ locus using DNA from an uninjected embryo and 5 randomly selected homozygous $Chd2^{R1684H}$ embryos (p>0.05, unpaired t-test, t=4.60, df=6, n=4 technical replicates per sample, error bars=SEM). FIG. 3G. Genotyping of the F1 offspring confirmed that 100% were heterozygous for the R1684H mutation.

FIGS. 4A-4F. Zygotic ICHR occurs during G2 and is significantly increased by RAD51 G151D and BCCIP. FIG. 4A. $Chd2^{R1684H}$ genotyping results from blastomeres collected from 2-cell embryos generated via injection of IVF-derived zygotes with Cas9, crRNA/tracrRNA, and RAD51 protein. Unedited cells genotype as RH/+. FIG. 4B. Quantification of immunocytochemistry for RAD51 displayed number of zygotes positive for RAD51 puncta during G1 (9hpf, 1hpi), G2 (14hpf, 6hpi, PN4-5), or M-phase (16hpf, 8hpi). FIG. 4C. Representative images of RAD51 immunostaining from Cas9+RAD51-injected embryos during G1, G2, and M-phase. Arrowheads indicate RAD51 puncta. Dotted lines outline pronuclear nucleoli. FIG. 4D. Quantification of embryos positive for ICHR based on $Chd2^{R1684H}$ genotyping of blastocysts derived from embryos injected with Cas9/crRNA/tracrRNA and the indicated RAD51 variants (one-tailed chi-square test). FIG. 4E. Quantification of editing efficiency in blastocysts derived from Cas9/crRNA/tracrRNA-injected embryos co-injected with the indicated RAD51 variants (one-tailed chi-square test). FIG. 4F. Quantification of embryos positive for ICHR based on $Chd2^{R1684H}$ genotyping of blastocysts derived from embryos injected with Cas9/crRNA/tracrRNA and the indicated DSB repair-related proteins (one-tailed chi-square test).

FIG. 7A. Representative Sanger sequencing traces of putative homozygous indels observed in $F_0$ animals obtained from Chd2$^{R1684H}$ knock-in experiments. FIG. 7B. Representative Sanger sequencing traces of putative homozygous indels observed in $F_0$ animals obtained from Tyr$^{C89S}$ knock-in experiments. FIG. 7C. Genotyping traces for a putative homozygous Chd2 indel and an $F_1$ offspring from a cross between the founder and a wildtype C57BL/6N mate. The $F_1$ genotyping, which was consistent for all 7 pups in the litter, indicates heterozygous presence of the indel observed in the founder.

FIGS. 10A-10D. Effects of ICHR enhancers on mosaicism. FIG. 10A. Representative chromatograms showing example traces for genotypes characterized as unedited (top left), 100% ICHR (top right), mosaic with wildtype (bottom left), and mosaic with indel (bottom right). FIG. 10B. Quantification of mosaicism in embryos displaying ICHR for all conditions analyzed. Data includes all embryos derived IVF (FIG. 3E, FIG. 4D, and FIG. 4F; SA208-209ED: p=0.037, two-tailed chi-square test; BCCIP: p=0.0041, two-tailed chi-square test). FIG. 10C. Distribution of types of mosaicism observed in mosaic embryos described in FIG. 10B. (BCCIP: p=0.034, two-tailed chi-square test). FIG. 10D. Numbers for observed mosaicism used to generate FIG. 10B and FIG. 10C.

FIG. 11A. Quantification of RAD51 puncta number observed in G2 zygotes injected with nothing, RAD51 alone, Cas9/crRNA/tracrRNA alone, or Cas9/crRNA/tracrRNA and RAD51. Each point represents a single cell. FIG. 11B. Representative images of cells with one (top left), two (top right), three (bottom left), or four (bottom right) RAD51 puncta (arrowheads indicate puncta; DAPI, blue; RAD51, green; scale=10 µm).

FIG. 13A. Total protein staining and Western blotting of recombinant RAD51. Membrane was stained for total protein, imaged, then stripped and probed with an anti-RAD51 antibody. FIG. 13B. Coomassie staining (left, prior to His-tag removal; right, after tag removal) and His-tag Western blotting of recombinant RAD51 mutants produced for injections described in FIGS. 4A-4I. FIG. 13C. Total protein staining of recombinant DSB repair- and HR-associated proteins used in FIG. 4F (protein marker on far-right).

FIG. 15A. Schematic depicting experimental design. FIG. 15B. ICHR enhancement increases delta 32 allele frequency in heterozygous HEK293T cells (p<0.001). FIG. 15C. Representative chromatograms showing example traces for WT/Delta32 heterozygous and Delta32 homozygous genotypes.

FIG. 16A. Schematic depicting experimental design. For Line-1: P2A-donor, a premature stop codon was introduced at the 3' end of the nucleic acid sequence of EGFP (EGFP-I188X). For Line-2: EGFP-donor, a premature stop codon was introduced in the nucleic acid sequence of P2A. For Line-3: EGFP-donor.2, a premature stop codon was introduced in the nucleic acid sequence of hSpCas9 (D10X). FIG. 16B. Schematic depicting targeted ICHR (i.e., EGFP conversion) in a Line-1/2 transgenic mouse using a guideRNA (i.e., guideRNA$^{StopEGFP}$) directed at the premature stop codon at the 3' end of the nucleic acid sequence of EGFP. FIG. 16C. Schematic depicting targeted ICHR (i.e., EGFP conversion) in a Line-1/2 transgenic mouse using a guideRNA (i.e., guideRNA$^{StopP2A}$) directed at the premature stop codon in the nucleic acid sequence of P2A.

DETAILED DESCRIPTION

Figure 2A:
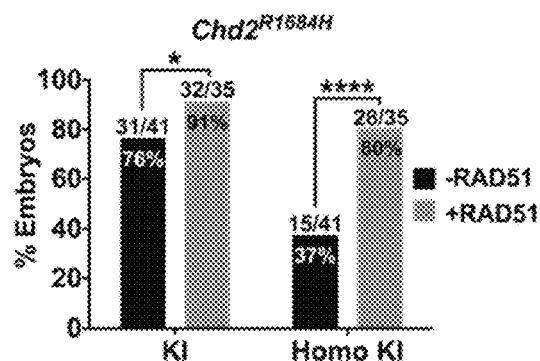
FIGS. 2A-2E. Exogenous RAD51 enhances KI efficiency at multiple loci.
Figure 2B:
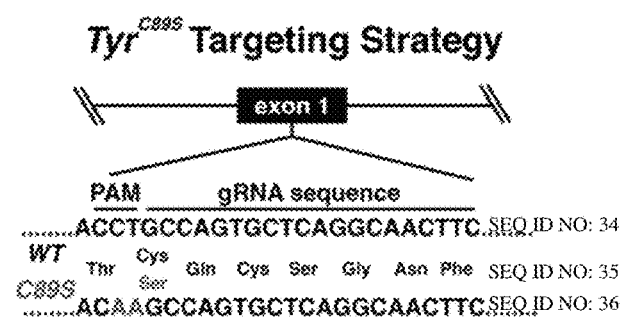

Recent advances in CRISPR/Cas-based genome editing, including three-component CRISPR (Aida T., et al., Genome Biol. 2015 Apr. 29; 16: 87), long single-strand donors (Quadros R. M., et al., Genome Biol. 2017 May 17; 18(1): 92), enhanced microhomology-mediated end-joining (MMEJ) (Aida T., et al., BMC Genomics. 2016 Nov. 28; 17(1): 979.4), and pharmacological approaches (Li G., et al., Sci. Rep. 2007 Aug. 21; 7(1): 8943; Maruyama T., et al., Nat. Biotechnol. 2015 May; 33(5): 538-42; Song J., et al., Nat. Commun. 2016 Jan. 28; 10548; Yu C., et al., Cell Stem Cell. 2015 Feb. 5; 16(2): 142-7) have greatly improved knock-in (KI) efficiency.

In a search for factors to further improve KI efficiency for broad therapeutic use and efficient generation of primate disease models, it is reported herein that the strand exchange protein RAD51 can significantly increase CRISPR/Cas9-mediated homology-dependent KI efficiency in mouse embryos. Surprisingly, it was found that in the presence of exogenous RAD51, most KI embryos are homozygous. More importantly, it was found that exogenous RAD51 greatly enhances interchromosomal homologous recombination/repair ("ICHR") for both generating homozygous KI animals from wildtype zygotes with exogenous donors and for converting heterozygous alleles into homozygous alleles without exogenous templates. These results provide both conclusive evidence supporting the previous controversial finding of interchromosomal homologous recombination in human embryos (Ma H., et al. Nature. 2017 Aug. 24; 548(7668): 413-19; Egli D., et al., bioRxiv. 2017 Aug. 28; doi:10.1101/181255) and a new method to significantly improve ICHR efficiency.

Described herein are methods of enhancing ICHR to stimulate a loss of heterozygosity at a gene locus of interest in a living cell. These methods have broad implications for applications in basic sciences, disease modeling, and therapeutic gene editing. In some embodiments, the methods enhance interchromosomal homologous recombination, or recombination between two or more chromosomes. In other embodiments, the methods enhance intrachromosomal homologous recombination, or recombination within a single chromosome. For example, in some embodiments, the methods enhance intrachromosomal homologous recombination between gene homologs on the same chromosome.

As used herein, the term "gene locus of interest" refers to at least two homologous polynucleic acid sequences, or "alleles" or "homologs," encoded on at least one chromosome of a cell. As used herein, the terms "allele" and "homolog" can be used interchangeably. As used herein, "homologous polynucleic acid sequences" refers to sequences that have at least 90% sequence identity over a sequence length of at least 30 base pairs. In some embodiments, the homologous polynucleic acid sequences have 90%, 95%, 96%, 97%, 98%, 99%, or 99.9% sequence identity over a sequence length of at least 30, 40, 50, 100, 500, 1000, 10,000, or greater than 10,000 base pairs.

In some embodiments, the gene locus of interest comprises two alleles on a single chromosome of a cell. For example, a desired allele and an undesired allele of a gene locus of interest may be on the same chromosome. In other embodiments, the gene locus of interest comprises two alleles on at least two pair chromosomes of a cell. For example, a desired allele and an undesired allele of a gene locus of interest may be on homologous chromosomes. In some embodiments, the cell is diploid (i.e., has two sets of chromosomes). In other embodiments, the cell is polyploid. For example, a cell may be tetraploid (i.e., has four sets of chromosomes) or hexaploid (i.e., has six sets of chromosomes).

A gene locus of interest may be homozygous (i.e., the polynucleic acid sequence of each allele of a gene of interest is identical) or heterozygous (i.e., the polynucleic acid sequence of the alleles of a gene of interest differ). Thus, a gene of interest that is heterozygous may comprise at least one desired allele (on at least one chromosome) and at least one undesired allele (on at least one chromosome). In some embodiments, the at least one desired allele and the at least one undesired allele are on the same chromosome. In some embodiments, the at least one desired allele and the at least one undesired allele are on different chromosomes.

In some embodiments, a desired allele and an undesired allele of a heterozygous gene of interest differ by only a single nucleotide. In other embodiments, a desired allele and an undesired allele of a heterozygous gene of interest differ by multiple nucleotides. As used herein, "loss of heterozygosity" refers to the conversion of a heterozygous gene of interest into a homozygous gene of interest. Methods of identifying genes of interest, comprising heterozygous alleles, in a living cell are known to those having skill in the art. For example, the genome of a parent or a sister cell can be sequenced or the transcriptome or proteome of the living cell can be sequenced.

In some embodiments, the homologous polynucleic acid sequence of a gene of interest comprises a gene coding segment of DNA. In other embodiments, the homologous polynucleic acid sequence comprises a noncoding segment of DNA. For example, in some embodiments, the homologous polynucleic acid sequence of a gene of interest comprises the sequence of a regulatory element, an intron, a noncoding functional RNA, a repeat sequence, or a telomere. In some embodiments, the regulatory element is selected from the group consisting of an operator, an enhancer, a silencer, a promoter, or an insulator. In some embodiments, a homologous polynucleic acid sequence comprises a gene coding and noncoding segment of DNA.

The length of each particular gene locus of interest can vary. For example, in some embodiments, a gene locus of interest is less than 1 kb in length. In other embodiments, a gene locus of interest is greater than 1 kb in length. For example, in some embodiments, a gene locus of interest is greater than 5 kb, 10 kb, 50 kb, 100 kb, or 1000 kb in length.

In some embodiments, the disclosure relates to methods of stimulating a loss of heterozygosity at a gene locus of interest in a living cell comprising: (a) identifying at least one gene locus of interest in a living cell, wherein each of the at least one gene locus of interest comprises a desired allele and an undesired allele, and (b) introducing an enzymatic unit into the living cell, wherein the enzymatic unit enhances chromosomal homologous recombination between the desired allele and the undesired allele of each of the at least one gene locus of interest and wherein the enzymatic unit comprises at least one enhancer component and at least one target-specific endonuclease component and wherein the chromosomal homologous recombination generates homozygosity at each of the at least one gene locus of interest, wherein each of the at least one gene of interest comprises only desired alleles after chromosomal homologous recombination.

In some embodiments, exogenous donor DNA is not introduced into the living cell, wherein the exogenous donor DNA comprises at least one polynucleic sequence that is homologous to at least one of the at least one gene locus of interest. In other embodiments, exogenous donor DNA is introduced into the living cell.

The "enhancer component" of the enzymatic unit, in some embodiments, is selected from the group consisting of a Rad51, Rad51 G151D, Rad52, Rad54, BRCA1, BRCA2, PALB2, XRCC1, XRCC4, USP1, WDR48, DMC1, BCCIP, BLM, C19ORF40, EME1, EME2, FANCA, FANCB, FANCC, FANCD2, FANCE, FANCF, FANCG, FANC1, FANCL, MRE11A, MSH4, MSH5, and MUS81 component. In some embodiments, at least one of the at least one enhancer component comprises a polynucleic acid that encodes for a polypeptide sequence that comprises the polypeptide sequence of Rad51 (e.g., NCBI Reference Sequences NM_001164269.1, NM_001164270.1, NM_002875.4, NM_133487.3, and polynucleic acid sequences encoding for polypeptide sequences that comprise functional variants, thereof), Rad51 G151D (e.g., sequence in Table 2 below; Chen et al. Nucleic Acids Res. 2015 Jan. 30; 43(2): 1098-1111, Rad52 (e.g., NCBI Reference Sequences NM_001297419.1, NM_001297420.1, NM_001297421.1, NM_001297422.1, NM_134424.3, and polynucleic acid sequences encoding for polypeptide sequences that comprise functional variants, thereof), Rad54

(e.g., NCBI Reference Sequences NM_000489.4, NM_138270.2, and polynucleic acid sequences encoding for polypeptide sequences that comprise functional variants, thereof), BRCA1 (e.g., NCBI Reference Sequences NM_007294.3, NM_007297.3, NM_007298.3, NM_007299.3, NM_007300.3, and polynucleic acid sequences encoding for polypeptide sequences that comprise functional variants, thereof), BRCA2 (e.g., NCBI Reference Sequences NM_000059.3 and polynucleic acid sequences encoding for polypeptide sequences that comprise functional variants, thereof), PALB2 (e.g., NCBI Reference Sequence NM_024675.3 and polynucleic acid sequences encoding for polypeptide sequences that comprise functional variants, thereof), XRCC1 (e.g., NCBI Reference Sequence NM_006297.2 and polynucleic acid sequences encoding for polypeptide sequences that comprise functional variants, thereof), XRCC4 (e.g., NCBI Reference Sequences NM_001318012.1, NM_001318013.1, NM_003401.4, NM_022406.3, NM_022550.3, and polynucleic acid sequences encoding for polypeptide sequences that comprise functional variants, thereof), USP1 (e.g., NCBI Reference Sequences NM_001017415.1, NM_001017416.1, NM_003368.4, and polynucleic acid sequences encoding for polypeptide sequences that comprise functional variants, thereof), WDR48 (e.g., NCBI Reference Sequences NM_001303402.1, NM_001303403.1, NM_001346225.1, NM_001346226.1, NM_001346227.1, NM_001346228.1, NM_020839.3, and polynucleic acid sequences encoding for polypeptide sequences that comprise functional variants, thereof), DMC1 (e.g., NCBI Reference Sequences NM_001278208.1, NM_007068.3, and polynucleic acid sequences encoding for polypeptide sequences that comprise functional variants, thereof), BCCIP (e.g., NCBI Reference Sequences NM_016567.3, NM_078468.2, NM_078469.2, and polynucleic acid sequences encoding for polypeptide sequences that comprise functional variants, thereof), BLM (e.g., NCBI Reference Sequences NM_000057.3, NM_001287246.1, NM_001287247.1, NM_001287248.1, and polynucleic acid sequences encoding for polypeptide sequences that comprise functional variants, thereof), C19ORF40 (e.g., NCBI Reference Sequences NM_001300978.1, NM_152266.4, and polynucleic acid sequences encoding for polypeptide sequences that comprise functional variants, thereof), EME1 (e.g., NCBI Reference Sequences NM_001166131.1, NM_152463.2, and polynucleic acid sequences encoding for polypeptide sequences that comprise functional variants, thereof), EME2 (e.g., NCBI Reference Sequences NM_001257370.1, and polynucleic acid sequences encoding for polypeptide sequences that comprise functional variants, thereof), FANCA (e.g., NCBI Reference Sequences NM_000135.3, NM_001018112.2, NM_001286167.2, NM_001351830.1, and polynucleic acid sequences encoding for polypeptide sequences that comprise functional variants, thereof), FANCB (e.g., NCBI Reference Sequences NM_001018113.2, NM_001324162.2, NM_152633.3, and polynucleic acid sequences encoding for polypeptide sequences that comprise functional variants, thereof), FANCC (e.g., NCBI Reference Sequences NM_000136.2, NM_001243743.1, NM_001243744.1, and polynucleic acid sequences encoding for polypeptide sequences that comprise functional variants, thereof), FANCD2 (e.g., NCBI Reference Sequences NM_001018115.2, NM_001319984.1, NM_033084.4, and polynucleic acid sequences encoding for polypeptide sequences that comprise functional variants, thereof), FANCE (e.g., NCBI Reference Sequences NM_021922.2, and polynucleic acid sequences encoding for polypeptide sequences that comprise functional variants, thereof), FANCF (e.g., NCBI Reference Sequences NM_022725.3, and polynucleic acid sequences encoding for polypeptide sequences that comprise functional variants, thereof), FANCG (e.g., NCBI Reference Sequences NM_004629.1, and polynucleic acid sequences encoding for polypeptide sequences that comprise functional variants, thereof), FANCI (e.g., NCBI Reference Sequences NM_001113378.1, NM_018193.2, and polynucleic acid sequences encoding for polypeptide sequences that comprise functional variants, thereof), FANCL (e.g., NCBI Reference Sequences NM_001114636.1, NM_018062.3, and polynucleic acid sequences encoding for polypeptide sequences that comprise functional variants, thereof), MRE11A (e.g., NCBI Reference Sequences NM_001330347.1, NM_005590.3, NM_005591.3, and polynucleic acid sequences encoding for polypeptide sequences that comprise functional variants, thereof), MSH4 (e.g., NCBI Reference Sequences NM_002440.3, and polynucleic acid sequences encoding for polypeptide sequences that comprise functional variants, thereof), MSH5 (e.g., NCBI Reference Sequences NM_002441.4, NM_025259.5, NM_172165.3, NM_172166.3, and polynucleic acid sequences encoding for polypeptide sequences that comprise functional variants, thereof), or MUS81 (e.g., NCBI Reference Sequences NM_001350283.1, NM_025128.4, and polynucleic acid sequences encoding for polypeptide sequences that comprise functional variants, thereof).

In some embodiments, at least one of the at least one enhancer component comprises a polypeptide that comprises the polypeptide sequence of Rad51 (e.g., NCBI Reference Sequences NP_001157741.1, NP_001157742.1, NP_002866.2, NP_597994.3, and functional variants, thereof), Rad51 G151D (e.g., Chen et al. Nucleic Acids Res. 2015 Jan. 30; 43(2): 1098-1111, Rad52 (e.g., NCBI Reference Sequences NP_001284348.1, NP_001284349.1, NP_001284350.1, NP_001284351.1, NP_602296.2, and functional variants, thereof), Rad54 (e.g., NCBI Reference Sequences NP_000480.3, NP_612114.2, and functional variants, thereof), BRCA1 (e.g., NCBI Reference Sequences NP_009225.1, NP_009228.2, NP_009229.2, NP_009230.2, NP_009231.2, v), BRCA2 (e.g., NCBI Reference Sequence NP_000050.2, and functional variants, thereof), PALB2 (e.g., NCBI Reference Sequence NP_078951.2, and functional variants, thereof), XRCC1 (e.g., NCBI Reference Sequences NP_006288.2, and functional variants, thereof), XRCC4 (e.g., NCBI Reference Sequences NP_001304941.1, NP_001304942.1, NP_003392.1, NP_071801.1, NP_072044.1, and functional variants, thereof), USP1 (e.g., NCBI Reference Sequences NP_001017415.1, NP_001017416.1, NP_003359.3, and functional variants, thereof), WDR48 (e.g., NCBI Reference Sequences NP_001290331.1, NP_001290332.1, NP_001333154.1, NP_001333155.1, NP_001333156.1, NP_001333157.1, NP_065890.1, and functional variants, thereof), DMC1 (e.g., NCBI Reference Sequences NP_001265137.1, NP_008999.2, and functional variants, thereof), BCCIP (e.g., NCBI Reference Sequences NP_057651.1, NP_510868.1, NP_510869.1, and functional variants, thereof), BLM (e.g., NCBI Reference Sequences NP_000048.1, NP_001274175.1, NP_001274176.1, NP_001274177.1, and functional variants, thereof), C19ORF40 (e.g., NCBI Reference Sequences NP_001287907.1, NP_689479.1, and functional variants, thereof), EME1 (e.g., NCBI Reference Sequences NP_001159603.1, NP_689676.2, and functional variants, thereof), EME2 (e.g., NCBI Reference Sequences NP_001244299.1, and functional variants, thereof), FANCA (e.g., NCBI Reference Sequences NP_000126.2, NP_001018122.1, NP_001273096.1, NP_001338759.1, and functional variants, thereof), FANCB (e.g., NCBI Reference Sequences NP_001018123.1, NP_001311091.1, NP_689846.1, and functional variants, thereof), FANCC (e.g., NCBI Reference Sequences NP_000127.2, NP_001230672.1, NP_001230673.1, and functional variants, thereof), FANCD2 (e.g., NCBI Reference Sequences NP_001018125.1, NP_001306913.1, NP_149075.2, and functional variants, thereof), FANCE (e.g., NCBI Reference Sequences NP_068741.1, and functional variants, thereof), FANCF (e.g., NCBI Reference Sequences NP_073562.1, and functional variants, thereof), FANCG (e.g., NCBI Reference Sequences NP_004620.1, and functional variants, thereof), FANCI (e.g., NCBI Reference Sequences NP_001106849.1, NP_060663.2, and functional variants, thereof), FANCL (e.g., NCBI Reference Sequences NP_001108108.1, NP_060532.2, and functional variants, thereof), MRE11A (e.g., NCBI Reference Sequences NP_001317276.1, NP_005581.2, NP_005582.1, and functional variants, thereof), MSH4 (e.g., NCBI Reference Sequences NP_002431.2, and functional variants, thereof), MSH5 (e.g., NCBI Reference Sequences NP_002432.1, NP_079535.4, NP_751897.1, NP_751898.1, and functional variants, thereof), or MUS81 (e.g., NCBI Reference Sequences NP_001337212.1, NP_079404.3, and functional variants, thereof).

Inhibition of 53BP1 increases the efficiency of homology-dependent repair (Canny M. D., et al., Nat. Biotechnol., 2018 January; 36(1): 95-102). As such, the "enhancer component" of the enzymatic unit, in some embodiments, is a 53BP1 component. In some embodiments, the 53BP1 component comprises a polynucleic acid that encodes for a polypeptide sequence that comprises the polypeptide sequence of a dominant negative form of 53BP1. In some embodiments, the 53BP1 component comprises a polypeptide sequence that comprises the polypeptide sequence of a dominant negative form of 53BP1. In some embodiments the dominant negative form of 53BP1 is the previously published i53 variant (Canny M. D., et al., Nat. Biotechnol., 2018 January; 36(1): 95-102). In some embodiments, the 53BP1 component comprises a small molecule inhibitor of 53BP1.

In some embodiments, at least one of the at least one enhancer component is a Rad51, Rad51 G151D, or BCCIP component. In some embodiments, the Rad51, Rad51 G151D, or BCCIP component comprises a polynucleic acid sequence that encodes for a polypeptide sequence that comprises the polypeptide sequence of Rad51, Rad51 G151D, or BCCIP, respectively. In some embodiments, the Rad51, Rad51 G151D, or BCCIP component comprises a polypeptide sequence that comprises the polypeptide sequence of Rad51, Rad51 G151D, or BCCIP, respectively. Of note, BCCIP and RAD51 G151D are capable of stimulating essentially error-free (and, at least in some contexts, error-free) ICHR. As used herein, "error-free" means that 100% of the potential cellular editing events occur during chromosomal homologous recombination/repair (i.e., there are no indels/errors, each cell is edited). The term "essentially error-free" means that at least 70% of the potential cellular editing events occur during chromosomal homologous recombination/repair (i.e., at least 70% of the events are indel/error free). As such, in some embodiments, chromosomal homologous recombination/repair is essentially error-free when at least 70%, at least 75%, at least 80%, at least 85%, at least 90%, at least 91%, at least 92%, at least 93%, at least 94%, at least 95%, at least 96%, at least 97%, at least 98%, at least 99%, or between 99% and 100% of the events are indel/error free.

In some embodiments, the Rad51 component comprises a small molecule that enhances homologous directed repair. In some embodiments, the small molecule that enhances homologous directed repair knocks down the expression of a repressor of Rad51 expression (e.g., an siRNA or chemical inhibitor). In some embodiments, the small molecule that enhances homologous directed repair enhances expression of Rad51 (e.g., doxorubicin). In some embodiments, the small molecule enhances the activity of Rad51. For example, in some embodiments, the small molecule is RS-1. Other examples of small molecules that stimulate the activity of Rad51 are known to those having skill in the art (e.g., US published patent application 2017/0014360, the entirety of which is incorporated, herein).

In some embodiments, the enzymatic unit is catalytically dead in that the introduction of the enzymatic unit does not result in DNA cleavage. In other embodiments, the enzymatic unit cleaves the undesired allele of each of the at least one gene locus of interest. As used herein, the term "cleaves" refers to a reaction that breaks the covalent sugar-phosphate linkage between nucleotides of a polynucleic acid sequence. In some embodiments, the enzymatic unit cleaves the undesired allele of at least one of the at least one gene locus of interest through the introduction of a single-strand break. In some embodiments, the enzymatic unit cleaves the undesired allele of at least one of the at least one gene locus of interest through the introduction of a double-strand break. In some embodiments comprising at least two genes of interest, at least one of the at least two undesired alleles is cleaved through the introduction of a single-strand break and at least one of the at least two undesired alleles is cleaved through the introduction of a double-strand break.

In some embodiments, the undesired allele of each of the at least one gene locus of interest is cleaved only once. In some embodiments, the undesired allele of the only gene of interest is cleaved only once. In other embodiments, at least two genes of interest are identified in the living cell and the undesired allele of at least one gene locus of interest is cleaved only once and the undesired allele of at least one gene of interest is cut more than once. In other embodiments, the undesired allele of each of the at least one gene of interest is cleaved more than once. In some embodiments, the undesired allele of the only gene of interest is cleaved more than once. Introduction of multiple cuts in an undesired allele may be particularly desirable for the enhancement of chromosomal recombination long genes of interest.

In some embodiments, the desired allele of each of the at least one gene locus of interest remains uncleaved. In some embodiments, the desired allele of the only gene of interest remains uncleaved. In other embodiments, at least two genes of interests are identified in the living cell and the desired allele of at least one gene locus of interest remains uncleaved and the desired allele of at least one gene of interest is cleaved at least once. For example, in some embodiments the genome of the living cell comprises two genes of interest, with the desired allele of one gene of interest remaining uncleaved and the desired allele of the other gene of interest being cleaved at least once. In other embodiments, the desired allele of each of the at least one gene of interest is cleaved at least once. In other embodiments, the desired allele of each of the at least one gene of interest is cleaved more than once. In some embodiments, the desired allele of the only gene of interest is cleaved more than once.

The "target-specific endonuclease component" of the enzymatic unit provides for target specificity. In some embodiments, at least one of the at least one target-specific endonuclease component comprises a polynucleic acid that encodes for a polypeptide sequence that comprises the polypeptide sequence of a target-specific endonuclease. In some embodiments, at least one of the at least one target-specific endonuclease component comprises a polypeptide that comprises the polypeptide sequence of a target-specific endonuclease.

In some embodiments, the polypeptide sequence of the target-specific endonuclease comprises the polypeptide sequence of an RNA-dependent endonuclease. As used herein the term "RNA-dependent endonuclease" refers to an endonuclease that utilizes an RNA molecule for targeting and/or binding of a specific DNA sequence. In some embodiments, the RNA-dependent endonuclease cleaves both strands of a double-stranded DNA molecule. In other embodiments, the RNA-dependent endonuclease cleaves only one strand of a double-stranded DNA molecule (e.g., a nickase). In some embodiments, the RNA-dependent endonuclease is a CRISPR/Cas protein.

As used herein, the term "CRISPR/Cas protein" refers to an RNA-guided DNA endonuclease, including, but not limited to, Cas9, Cpf1, C2c1, and C2c3 and each of their orthologs and functional variants. CRISPR/Cas protein orthologs have been identified in many species and are known or recognizable to those of ordinary skill in the art. For example, Cas9 orthologs have been described in various species, including, but not limited to Bacteroides coprophilus (e.g., NCBI Reference Sequence: WP_008144470.1), Campylobacter jejuni susp. jejuni (e.g., GenBank: AJP35933.1), Campylobacter lari (e.g., GenBank: AJD02827.1), Fancisella novicida (e.g., UniProtKB/Swiss-Prot: A0Q5Y3.1), Filifactor alocis (e.g., NCBI Reference Sequence: WP_083799662.1), Flavobacterium columnare (e.g., GenBank: AMA50561.1), Fluviicola taffensis (e.g., NCBI Reference Sequence: WP_013687888.1), Gluconacetobacter diazotrophicus (e.g., NCBI Reference Sequence: WP_041249387.1), Lactobacillus farciminis (e.g., NCBI Reference Sequence: WP_010018949.1), Lactobacillus johnsonii (e.g., GenBank: KXN76786.1), Legionella pneumophila (e.g., NCBI Reference Sequence: WP_062726656.1), Mycoplasma gallisepticum (e.g., NCBI Reference Sequence: WP_011883478.1), Mycoplasma mobile (e.g., NCBI Reference Sequence: WP_041362727.1), Neisseria cinerea (e.g., NCBI Reference Sequence: WP_003676410.1), Neisseria meningitidis (e.g., GenBank: ODP42304.1), Nitratifractor salsuginis (e.g., NCBI Reference Sequence: WP_083799866.1), Parvibaculum lavamentivorans (e.g., NCBI Reference Sequence: WP_011995013.1), Pasteurella multocida (e.g., GenBank: KUM14477.1), Sphaerochaeta globusa (e.g., NCBI Reference Sequence: WP_013607849.1), Staphylococcus aureus (e.g., GenBank: HE980450.1), Streptococcus pasteurianus (e.g., Gene ID: 901176), Streptococcus pyogenes (e.g., NCBI Reference Sequence: WP_061100419.1), Streptococcus thermophilus (e.g., GenBank: ANJ62426.1), Sutterella wadsworthensis (e.g., NCBI Reference Sequence: WP_005430658.1), and Treponema denticola (e.g., NCBI Reference Sequence: WP_002684945.1). In some embodiments, the CRISPR/Cas protein is Cas9.

In some embodiments, the CRISPR/Cas protein is a mutated CRISPR/Cas protein, wherein the mutated CRISPR/Cas protein comprises a mutated nuclease domain and wherein the mutated CRISPR/Cas protein generates single-strand breaks. For example, nickase Streptococcus pyogenes Cas9 (i.e., SpCas9) mutants have been generated through incorporation of D10 and H480 mutations (Jinek et al., Science 337, 816-21 (2012); Ran et al., Cell 154, 1380-89 (2013)). In other embodiments, the CRISPR/Cas protein is a mutated CRISPR/Cas protein, wherein the mutated CRISPR/Cas protein comprises a mutated nuclease domain and wherein the mutated CRISPR/Cas protein is catalytically inactive. The term "catalytically-inactive" as used herein refers to a CRISPR/Cas protein variant or mutant that lacks endonuclease activity (i.e., the ability to cleave a polynucleic acid molecule). For example, catalytically-inactive SpCas9 mutants have been generated through incorporation of D10 and H481 mutations (Jinek et al., Science 337, 816-21 (2012)). Catalytically-inactive Acidaminococcus sp. BV3L6 Cpf1 (i.e., AsCpf1) and catalytically-inactive Lachnospiraceae bacterium ND2006 (i.e., LbCpf1) mutants have been generated through incorporation of D908 and D832 mutations, respectively (Zetsche et al., Cell 163, 759-71 (2015)).

In some embodiments, the enzymatic unit further comprises at least one crRNA, at least one tracrRNA (i.e., trans-activating crRNA), and/or at least one sgRNA. crRNAs and sgRNAs are polynucleic acid molecules that have sequences that complement the target site, which mediate the binding of the CRISPR/Cas complex to the target site, providing the specificity of the CRISPR/Cas complex. Typically, crRNAs and sgRNAs that exist as single RNA species comprise two domains: (1) a "guide" domain that shares homology to a target nucleic acid (e.g., directs binding of a CRISPR/Cas complex to a target site); and (2) a "direct repeat" domain that binds a CRISPR/Cas protein. In this way, the sequence and length of a small guide RNA may vary depending on the specific guide RNA target site and/or the specific CRISPR/Cas protein (Zetsche et al. Cell 163, 759-71 (2015)). The term "CRISPR/Cas complex" refers to a CRISPR/Cas protein that is bound to a crRNA or a sgRNA. A tracrRNA plays a role in the maturation of some crRNAs.

In some embodiments, the polypeptide sequence of the target-specific endonuclease comprises the polypeptide sequence of an RNA-independent endonuclease. As used herein, the term "RNA-independent endonuclease" refers to an endonuclease that does not utilize an RNA molecule for targeting and/or binding of a specific DNA sequence. In some embodiments, the RNA-independent endonuclease is selected from the group consisting of a meganuclease, a zinc-finger nuclease, a transcription activator-like effector nuclease, and a restriction enzyme, including functional variants thereof. In some embodiments, the RNA-independent endonuclease is a restriction enzyme, wherein the restriction enzyme is a site-specific DNA-nicking enzyme.

As used herein, the term "functional variant" includes polypeptides which are about 70% identical, at least about 80% identical, at least about 90% identical, at least about 95% identical, at least about 98% identical, at least about 99% identical, at least about 99.5% identical, or at least about 99.9% identical to a protein's native amino acid sequence (i.e., wild-type amino acid sequence) and which retain functionality.

The term "functional variant" also includes polypeptides which are shorter or longer than a protein's native amino acid sequence by about 5 amino acids, by about 10 amino acids, by about 15 amino acids, by about 20 amino acids, by about 30 amino acids, by about 40 amino acids, by about 50 amino acids, by about 75 amino acids, by about 100 amino acids or more and which retain functionality.

The term "functional variant" also includes orthologs found in other species.

The term "functional variant" also includes fusion/chimeric/hybrid proteins which retain functionality (e.g., fusion proteins that contain the binding domain of a CRISPR/Cas protein). The term "fusion protein," "chimeric protein," or "hybrid protein" refers to the combination of two or more polypeptides/peptides in a single polypeptide chain. Fusion/chimeric/hybrid proteins typically are produced genetically through the in-frame fusing of the nucleotide sequences encoding for each of the said polypeptides/peptides. Expression of the fused/chimeric/hybrid coding sequence results in the generation of a single protein without any translational terminator between each of the polypeptides/peptides. Alternatively, fusion/chimeric/hybrid proteins also can be produced by chemical synthesis. Examples of fusion/chimeric/hybrid proteins include, but are not limited to, a fusion between a target-specific endonuclease and a nuclease-domain (e.g., FokI or TEV) and/or a homing endonuclease.

In the context of an enhancer component, the term "retain functionality" refers to a protein that retains at least 10%, 20%, 30%, 40%, 50%, 60%, 70%, 80%, 90%, 100%, 150%, 200%, or more, of the enhancement of chromosomal homologous recombination between the desired allele and the undesired allele of each of the at least one gene locus of interest as described herein. Methods of measuring and comparing levels of chromosomal homologous recombination are known to those skilled in the art and are disclosed herein. In the context of a Rad51 component, examples of known Rad51 functional variants include, but are not limited to Rad51 G151D, Rad51 G135C, Rad51 T131P, Rad51 P339S, Rad51 I345T, and Rad51 V328A (Marsden C. G., et al., PLoS Genet. 2016 Aug. 11; 12(8): e1006208; Malik P. S. and Symington L. S., Nucleic Acids Res. 2008 November; 36(20): 6504-10). Methods of generating additional Rad51 functional variants, such as directed evolution, are known to those having skill in the art.

In the context of a target-specific endonuclease component, the term "retain functionality" refers to the target-specific endonuclease variant's ability to specifically target DNA at least about 5%, 10%, 20%, 25%, 30%, 40%, 50%, 60%, 70%, 75%, 80%, 90%, 100%, or more than 100% as efficiently as the respective non-variant (i.e., wild-type) target-specific endonuclease. Methods of measuring and comparing the efficiency of DNA targeting are known to those skilled in the art.

Methods of introducing material into a living cell are known to those having skill in the art. Examples include, but are not limited to, transduction, transfection (e.g., DEAE dextran-mediated transfection, CaPO4-mediated transfection, lipid-mediated DNA uptake, and PEI-mediated DNA uptake, laser transfection), transformation (e.g., calcium chloride, electroporation, and heat-shock), gene transfer, particle bombardment, and viral (or bacteriophage) infection.

In some embodiments, the enzymatic unit is packaged within a viral (or bacteriophage) delivery system that is cell-specific. In some embodiments, the viral delivery system comprises a single viral particle (i.e., the entire enzymatic unit is packaged within a single viral particle). In other embodiments, the viral delivery system comprises multiple viral particles. For examples, in some embodiments, the enhancer component and the target-specific endonuclease component of an enzymatic unit are contained in different viral particles. In some embodiments, the enhancer or target-specific endonuclease component are contained in more than one viral particle.

In some embodiments, the enzymatic unit is introduced into the cell in vitro. In other embodiments the enzymatic unit is introduced into the cell in vivo.

The term "enhances chromosomal homologous recombination" refers to an increase in the levels of chromosomal homologous recombination by at least 15%, 20%, 25%, 30%, 40%, 50%, 100%, 200%, 300% or more than 300% relative to the levels of chromosomal homologous recombination in the absence of the enzymatic unit. Methods of measuring and comparing levels of chromosomal homologous recombination are known to those skilled in the art. Various methods of doing so are provided herein (e.g., Materials and Methods and Example 3). In some embodiments, the loss of heterozygosity is enhanced by at least 15%, 20%, 25%, 30%, 40%, 50%, 100%, 200%, 300% or more than 300% relative to the loss of heterozygosity in the absence of the enhancer component. In some embodiments, the loss of heterozygosity is enhanced by at least 20% relative to the loss of heterozygosity in the absence of the at least one enhancer component. In some embodiments, the loss of heterozygosity is enhanced by at least 100% relative to the loss of heterozygosity in the absence of the at least one enhancer component.

In some embodiments, the living cell is a unicellular organism. In some embodiments, the unicellular organism is selected from the group consisting of a bacteria, archaea, protozoa, unicellular algae, and unicellular fungi. In some embodiments, the living cell is a cultured cell.

In some embodiments, the living cell is a cell of a multicellular organism, wherein the multicellular organism is administered a composition comprising: the at least one enhancer component; the at least one target-specific endonuclease component; and optionally a cellular delivery component. In some embodiments, the multicellular organism comprises multiple cell types.

As used herein the term "cellular delivery component" refers to any mechanism where by a cell of a multicellular organisms can be induced to uptake a composition. Examples of cellular delivery components include, but are not limited to, liposomes, micelles, nanoparticles, extracellular vesicles, cell membrane coated particles, and viruses (included bacteriophages).

In some embodiments, the multicellular organism is an animal. In some embodiments, the animal is a human patient suffering from a disease, wherein the disease is caused by heterozygosity at at least one gene locus of interest. In other embodiments, the multicellular organism is an insect. In other embodiments, the multicellular organism is a plant.

In some aspects, the disclosure relates to novel gene drive technologies (see Macias V. M. et al., Int. J. Environ. Res. Public Health, 14(9): ppi: E1006 (2017); Gene Drives on the Horizon: Advancing Science, Navigating Uncertainty, and Aligning Research with Public Values, National Academies Press (US), (2016); Sinkins and Gould, Nat. Rev. Genet., 7(6): 427-35 (2006) for background on current gene drive technologies, the entire contents of which are incorporated here by reference. As such, in some embodiments, the living cell is a cell of a genetically engineered transgenic organism, wherein at least one of the at least one gene locus of interest comprises a transgenic gene locus, wherein the desired allele of the transgenic gene locus is a transgenic payload gene and the undesired allele of the transgenic gene locus is an endogenous sequence. Thus, introduction of an enzymatic unit into a living cell of the genetically engineered transgenic organism enhances chromosomal homologous recombination between the transgenic payload gene and the undesired allele, generating cells that are homozygous for the transgenic payload gene. In some embodiments, the transgenic payload gene does not include an enzymatic component or an enhancer component. In some embodiments, the transgenic payload gene comprises at least one enhancer component. In some embodiments, the transgenic payload gene comprises at least one enzymatic unit. In some embodiments, the transgenic payload gene comprises at least one enhancer component and at least one enzymatic unit.

In other aspects, the disclosure relates to a therapeutic composition for use in a method of treating a medical condition caused by heterozygosity at an allele of a gene of interest. In other aspects, the disclosure relates to a therapeutic composition for use in a method of preventing a medical condition caused by a homozygosity at an allele of a gene of interest. For example, one potentially immediate application is the treatment and prevention of HIV infection. The C—C chemokine receptor type 5 (CCR5) is a co-receptor for HIV infection of white blood cells. 1% Europeans has a homozygous loss-of-function mutation of the gene (CCR5-delta32 mutation), and they are healthy and resistant to HIV infection. See Example 9.

The cause of the medical conditions that can be treated or prevented by the methods disclosed herein vary. For example, in some embodiments, the medical condition is monogenetic or Mendelian (i.e., caused by a single mutation). In other embodiments, the medical condition is polygenetic or a common complex diseases (i.e., caused by multiple mutations). With regard to polygenetic or common complex diseases, in some embodiments, the therapeutic composition can be used for the treatment of risk alleles or SNPs associated with the medical condition. Many risk alleles are often detected by genome-wide association studies. Risk alleles associated with various medical conditions are known to those having skill in the art.

The medical condition may be an autosomal dominant disorder. Examples of autosomal dominant disorders include, but are not limited to, Tuberous sclerosis, Marfan syndrome, Huntington's disease, Waardenburg syndrome, myotonic dystrophy, familial hypercholesterolemia, adult polycystic kidney disease, Von Hippel Lindau syndrome, Peutz-Jeghers syndrome, hereditary spherocytosis, Ehlor's Danlos, acute intermittent *porphyria*, hypertrophic obstructive cardiomyopathy, Von Willebrand Disease, polydactyly, and osteogenesis imperfecta.

The medical condition may be a disease caused by codominance or incomplete dominance, such as sickle cell anemia.

The medical condition may be an autosomal recessive disease. For example, a patient may be at risk of developing an autosomal recessive disease due to heterozygosity of allele at a particular gene of interest. Alternatively, a patient may be at risk of passing on a heterozygous allele to a biological offspring. Examples of autosomal recessive disease are known to those having skill in the art.

The therapeutic compositions described herein comprise an enzymatic unit, wherein the enzymatic unit enhances chromosomal homologous recombination between the desired allele and the undesired allele of each of the at least one gene locus of interest and wherein the enzymatic unit comprises at least one enhancer component and at least one target-specific endonuclease component and wherein the chromosomal homologous recombination generates homozygosity at each of the at least one gene locus of interest, wherein each of the at least one gene of interest comprises only desired alleles after chromosomal homologous recombination, as described above.

The therapeutic compositions can include a pharmaceutically-acceptable carrier. Generally, for pharmaceutical use, the therapeutic may be formulated as a pharmaceutical preparation or composition comprising at least one enzymatic unit and at least one pharmaceutically acceptable carrier, diluent or excipient, and optionally one or more further pharmaceutically active compounds. Such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such administration forms may be solid, semi-solid or liquid, depending on the manner and route of administration. For example, formulations for oral administration may be provided with an enteric coating that will allow the formulation to resist the gastric environment and pass into the intestines. More generally, formulations for oral administration may be suitably formulated for delivery into any desired part of the gastrointestinal tract. In addition, suitable suppositories may be used for delivery into the gastrointestinal tract. Various pharmaceutically acceptable carriers, diluents and excipients useful in therapeutic compositions are known to the skilled person.

In other aspects, the disclosure relates to the use of an enzymatic unit, as described herein, in the manufacture of a medicament for the treatment of a medical condition caused by a heterozygosity at an allele of a gene of interest. In yet other aspects, the disclosure relates to the use of an enzymatic unit, as described herein, in the manufacture of a medicament for the prevention of a medical condition caused by a homozygosity at an allele of a gene of interest.

In other aspects, the disclosure relates to a method of generating homozygous animal models comprising administering the animal a composition comprising an enzymatic unit, as described herein, and a single or double-stranded DNA donor, wherein the single or double-stranded donor DNA comprises terminal regions of homology to the target integration site. Examples of this methodology are provided in Example 1 and Example 2. This methodology facilitates the single-step generation of homozygous animal models. For example, ongoing efforts to generate primate models of human diseases have been hindered by low efficiency, long generation times, and high costs associated with obtaining homozygotes. However, this method has the potential to generate $F_0$ homozygotes with high efficiency, significantly decreasing costs and study length.

EXAMPLES

Methods and Materials

Animal Care and Use:

All mouse work was performed with the supervision of the Massachusetts Institute for Technology Division of Comparative Medicine (DCM) under protocol 0416-024-19, which was approved by the Committee for Animal Care (CAC). All procedures were in accordance with the guidelines set forth by the Guide for Care and Use of Laboratory Animals, National Research Council, 1996 (institutional animal assurance no. A-3125-01). All embryos injected for the experiments described herein were on a C57BL/6NTac background (Taconic; referred to as C57BL/6N herein).

Preparation of Injection Mixtures:

tracrRNA, crRNAs, and ssODNs were synthesized by Integrated DNA Technologies (TABLE 1). All injection mixtures were prepared in a final volume of 50 µL according to the following methodology: Using RNase-free water, reagents, and consumables, crRNA (final concentration 0.61 µM), tracrRNA (final concentration 0.61 µM), and ultrapure Tris-HCl, pH 7.39 (final concentration 10 mM, ThermoFisher) were mixed and incubated at 95° C. for 5 minutes. The mixtures were cooled to room temperature for 10 minutes on the benchtop, and then, EnGen Cas9-NLS *S. pyogenes* (New England Biolabs) was added to a final concentration of 30 ng/µL. The mixtures were incubated at 37° C. for 15 minutes before adding any remaining components: ssODN (final concentration 3 ng/µL or 30 ng/µL), RAD51 (Creative Biomart, final concentration 10 ng/µL). Injection mixtures were stored on ice and briefly heated to 37° C. prior to injection. For experiments utilizing RS-1, embryos were cultured in KSOM-AA (EMD Millipore MR-121-D) with 7.504 RS-1 (Sigma) dissolved in DMSO or DMSO (Sigma, 1:1000) for 24 hours, washed, and cultured in EmbryoMax FHM HEPES Buffered Medium (Sigma) until collection for genotyping.

TABLE 1

Sequences of Injection Components. Guide sequences are underlined.

| Component | Sequence | SEQ ID NO: |
|---|---|---|
| tracrRNA | AAACAGCAUAGCAAGUUAAAAUAAGGCUAGU CCGUUAUCAACUUGAAAAAGUGGCACCGAGU CGGUGCU | 1 |
| Chd2$^{R1684H}$ crRNA | <u>GCGGUAGCUCCCAGAACGGUGUUUUAGAGCU</u> AUGCUGUUUUG | 2 |
| Chd2$^{R1684H}$ ssODN | TCAGTATGAGCAGCATTGGTATAAGGACCAC CACTATGGTGACCGGAGGCATATGGATGCTC ACCATTCTGGGAGCTACCGCCCTAACAACAT GTCCAGAAAGAGGCCGTATGAGCAGTACAAC AG | 3 |
| Chd2$^{GT}$ Variant Donor | TCAGTATGAGCAGCATTGGTATAAGGACCAC CACTATGGTGACCGGAGGCATATGGATGCCA CCTTTCTGGGAGCTACCGCCCTAACAACATG TCCAGAAAGAGGCCGTATGAGCAGTACAACA G | 4 |
| Tyr$^{C89S}$ crRNA | <u>GAAGUUGCCUGAGCACUGGC</u>GUUUUAGAGCU AUGCUGUUUUG | 5 |
| Tyr$^{C89S}$ ssODN | GTTCCCCTTCAAAGGGGTGGATGACCGTGAG TCCTGGCCCTCTGTGTTTTATAATAGGACAA GCCAGTGCTCAGGCAACTTCATGGGTTTCAA CTGCGGAAACTGTAAGTTTGGATTTGGGG | 6 |

Recombinant Proteins:

For experiments using wildtype recombinant proteins, the following proteins were used: RAD51 (Creative Biomart RAD51-134H), USP1/WDR48 (Creative Biomart USP1&WDR48-1067H), BCCIP (Origene TP303061), XRCC1 (TP304952), XRCC4 (Origene TP312684), DMC1 (Origene TP318311). For experiments using mutant RAD51, custom RAD51 preparations were produced by Creative Biomart according to their standard protocol for producing the wildtype RAD51 used in all other experiments. Mutant DNA sequences used for cloning are described in TABLE 2. All RAD51 mutants were modeled in human RAD51 transcript variant 4 (NCBI accession NM_001164269), as this is the transcript variant of the wildtype RAD51-134H protein used in all other experiments.

TABLE 2

DNA Sequences for Production of Recombinant RAD51 Mutant Proteins. Mutated nucleotides are bold and underlined.

| RAD51 Mutant | DNA Sequence |
|---|---|
| T131P (SEQ ID NO: 7) | atggcaatgcagatgcagcttgaagcaaatgcagatactt cagtggaagaagaaagctttggcccacaacccatttcacg gttagagcagtgtggcataaatgccaacgatgtgaagaaa ttggaagaagctggattccatactgtggaggctgttgcct atgcgccaaagaaggagctaataaatattaagggaattag tgaagccaaagctgataaaattctgacggagtctcgctct gttgccaggctggagtgcaatagcgtgatcttggtctact gcaccctccgcctctcaggttcaagtgattctcctgcctc agcctcccgagtagttgggactacaggtggaattgagact ggatctatcacagaaatgtttggagaattccga<u>c</u>ctggga agacccagatctgtcatacgctagctgtcacctgccagct tcccattgaccggggtggaggtgaaggaaaggccatgtac attgacactgagggtacctttaggccagaacggctgctgg cagtggctgagaggtatggtctctctggcagtgatgtcct ggataatgtagcatatgctcgagcgttcaacacagaccac cagacccagctcctttatcaagcatcagccatgatggtag aatctaggtatgcactgcttattgtagacagtgccaccgc cctttacagaacagactactcgggtcgaggtgagctttca gccaggcagatgcacttggccaggtttctgcggatgcttc tgcgactcgctgatgagtttggtgtagcagtggtaatcac taatcaggtggtagctcaagtggatggagcagcgatgttt gctgctgatcccaaaaaacctattggaggaaatatcatcg cccatgcatcaacaaccagattgtatctgaggaaaggaag aggggaaaccagaatctgcaaaatctacgactctccctgt cttcctgaagctgaagctatgttcgccattaatgcagatg gagtgggagatgccaaagactga |
| G151D (SEQ ID NO: 8) | atggcaatgcagatgcagcttgaagcaaatgcagatactt cagtggaagaagaaagctttggcccacaacccatttcacg gttagagcagtgtggcataaatgccaacgatgtgaagaaa ttggaagaagctggattccatactgtggaggctgttgcct atgcgccaaagaaggagctaataaatattaagggaattag tgaagccaaagctgataaaattctgacggagtctcgctct gttgccaggctggagtgcaatagcgtgatcttggtctact gcaccctccgcctctcaggttcaagtgattctcctgcctc agcctcccgagtagttgggactacaggtggaattgagact ggatctatcacagaaatgtttggagaattccgaactggga agacccagatctgtcatacgctagctgtcacctgccagct tcccattgaccggg<u>at</u>ggaggtgaaggaaaggccatgtac attgacactgagggtacctttaggccagaacggctgctgg cagtggctgagaggtatggtctctctggcagtgatgtcct ggataatgtagcatatgctcgagcgttcaacacagaccac cagacccagctcctttatcaagcatcagccatgatggtag aatctaggtatgcactgcttattgtagacagtgccaccgc cctttacagaacagactactcgggtcgaggtgagctttca gccaggcagatgcacttggccaggtttctgcggatgcttc tgcgactcgctgatgagtttggtgtagcagtggtaatcac taatcaggtggtagctcaagtggatggagcagcgatgttt gctgctgatcccaaaaaacctattggaggaaatatcatcg cccatgcatcaacaaccagattgtatctgaggaaaggaag aggggaaaccagaatctgcaaaatctacgactctccctgt cttcctgaagctgaagctatgttcgccattaatgcagatg gagtgggagatgccaaagactga |
| SA208-209ED (SEQ ID NO: 9) | atggcaatgcagatgcagcttgaagcaaatgcagatactt cagtggaagaagaaagctttggcccacaacccatttcacg gttagagcagtgtggcataaatgccaacgatgtgaagaaa ttggaagaagctggattccatactgtggaggctgttgcct atgcgccaaagaaggagctaataaatattaagggaattag tgaagccaaagctgataaaattctgacggagtctcgctct gttgccaggctggagtgcaatagcgtgatcttggtctact gcaccctccgcctctcaggttcaagtgattctcctgcctc agcctcccgagtagttgggactacaggtggaattgagact ggatctatcacagaaatgtttggagaattccgaactggga |

TABLE 2-continued

DNA Sequences for Production of Recombinant
RAD51 Mutant Proteins. Mutated nucleotides
are bold and underlined.

| RAD51 Mutant | DNA Sequence |
|---|---|
| | agacccagatctgtcatacgctagctgtcacctgccagct tcccattgaccggggtggaggtgaaggaaaggccatgtac attgacactgagggtacctttaggccagaacggctgctgg cagtggctgagaggtatggtctctctggcagtgatgtcct ggataatgtagcatatgctcgagcgttcaacacagaccac cagacccagctcctttatcaagcagaagacatgatggtag aatctaggtatgcactgcttattgtagacagtgccaccgc cctttacagaacagactactcgggtcgaggtgagctttca gccaggcagatgcacttggccaggtttctgcggatgcttc tgcgactcgctgatgagtttggtgtagcagtggtaatcac taatcaggtggtagctcaagtggatggagcagcgatgttt gctgctgatcccaaaaaacctattggaggaaatatcatcg cccatgcatcaacaaccagattgtatctgaggaaaggaag aggggaaaccagaatctgcaaaatctacgactctccctgt cttcctgaagctgaagctatgttcgccattaatgcagatg gagtgggagatgccaaagactga |

Production of RAD51 mRNA:

Human RAD51 mRNA was prepared as described previously (Aida et al., BMC Genomics 17:979, 2016). pCMV-hRAD51 cDNA plasmid (a gift from Tetsushi Sakuma and Takashi Yamamoto, Hiroshima University) was linearized with SmaI (NEB) at 37° C. overnight, purified using DNA Clean & Concentrator kit (Zymo Research), eluted with nuclease-free water (Thermo Fisher Scientific), and used for T7-based in vitro transcription. RAD51 mRNA was in vitro transcribed using T7 mScript Standard mRNA Production System (Cellscript), purified using MEGAclear Kit (Thermo Fisher Scientific) according to manufacturer's instructions, and eluted with nuclease-free water. The quality of RAD51 mRNA was analyzed by NanoDrop (Thermo Fisher Scientific) and Bioanalyzer (Agilent Technologies).

Natural Mating for Zygotic Injections:

Female mice (4-5 weeks old, C57BL/6N) were superovulated by IP injection of PMS (5 IU/mouse, three days prior to microinjection) and hCG (5 IU/mouse, 47 hours after PMS injection) and then paired with males. Plugged females were sacrificed by cervical dislocation at day 0.5pcd and zygotes were collected into 0.1% hyaluronidase/FHM (Sigma). Zygotes were washed in drops of FHM and cumulus cells were removed. Zygotes were cultured in KSOM-AA for one hour and then used for microinjection.

In Vitro Fertilization for Zygotic Injections:

In vitro fertilization was performed using FERTIUP® Mouse Preincubation Medium and CARD MEDIA (Kyudo Company) according to the manufacturer's protocol. Non-virgin $Chd2^{R1684H/R1684H}$ males that were >8 weeks old were used as sperm donors. Following IVF, embryos were cultured for 8 hours and then injected using the PNI protocol described below.

Figure 6:
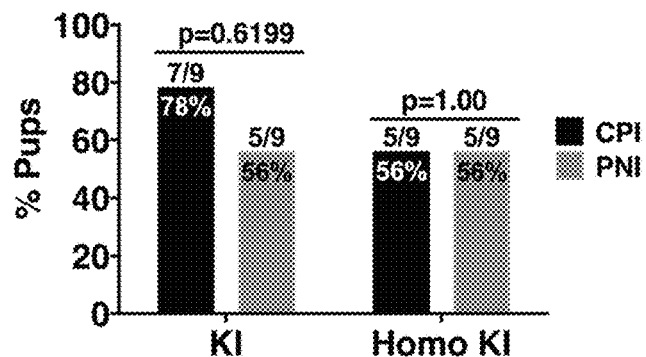
FIG. 6. Confirmation of $F_0$ homozygosity. Genotyping results for all $F_0$ pups obtained from either cytoplasmic (CPI) or pronuclear (PNI) injections for Chd2$^{R1684H}$ knock-in experiments described in FIGS. 1A-1E.

Zygotic Microinjections:

For all experiments except those described in FIG. 6, the male pronucleus was injected. Injections performed for the CPI portion of FIG. 6 were targeted to the cytoplasm. All microinjections were performed using a Narishige Micromanipulator, Nikon Eclipse TE2000-S microscope, and Eppendorf 5242 microinjector. Individual zygotes were injected with 1-2 pL of injection mixture using an "automatic" injection mode set according to needle size and adjusted for clear increase in pronuclear volume. Following injections, cells were cultured in KSOM-AA until collection for genotyping. For experiments giving rise to $F_0$ animals, embryos were surgically implanted into pseudopregnant CD-1 females (Charles River Laboratories, Strain Code 022) 24-hours post-injection and allowed to develop normally until natural birth.

Embryo Collection and DNA Purification:

Embryos were collected at morula-to-blastocyst stage in 4 µL nuclease-free water. After collection, 4 µL of 2× embryo digestion buffer was added to each sample (final concentrations: 125 µg/mL proteinase K, 100 mM Tris-HCl pH 8.0, 100 mM KCl, 0.02% gelatin, 0.45% Tween-20, 60 µg/mL yeast tRNA) and embryos were lysed for 1 hour at 56° C. Proteinase K was inactivated via incubation at 95° C. for 10 minutes and DNA was stored at −20° C. until use.

Tail DNA Purification:

Tail snips (~0.5 cm length) were collected from animals, placed in 75 µL alkaline lysis buffer (25 mM NaOH, 0.2 mM EDTA), and incubated at 95° C. for 30 minutes. Digestion was stopped via addition of 75 µL neutralization buffer (40 mM Tris-HCl pH 5.0). Samples were stored at 4° C. until genotyping.

$Chd2^{R1684H}$ PCR:

$Chd2^{R1684H}$ genotyping was performed via a two-step, nested approach. Except for experiments described in FIGS. 3A-3G, all 8 µL of embryo DNA were used as input for the initial, long round of PCR. Genotyping of mouse pups and adult animals was performed using 2 µL of purified tail DNA. For all embryo genotyping, reactions mixtures were set up in a UV-sterilized laminar flow hood using sterile reagents and filter tips to avoid contamination. All PCR was performed using Biolase DNA Polymerase (Bioline), fresh aliquots of dNTPs (New England Biolabs), and 2% DMSO (final concentration). The first PCR reaction of the nested PCR was performed using the C2RH-Long_F/R primer pairs listed in TABLE 3. Primer pair #1 was used for FIGS. 1A-1E, FIGS. 2A-2E, FIGS. 3A-3G, FIG. 5, FIGS. 7A-7C, FIG. 8, and FIG. 9. All other experiments utilized primer pair #2 to further rule out large deletions that could disrupt primer binding sites. 20 cycles of amplification were performed using 30 second extension and annealing times and an annealing temperature of 67° C. Nested PCR was then performed using 2 µL of the initial 25 µL PCR reaction as input. The C2RH-Short_F/R primer pairs listed in TABLE 3 were used for this PCR, with sets 1 and 2 being used as described above. Thirty-five cycles of amplification were performed using 30 second extension and annealing times and an annealing temperature of 68° C.

$Tyr^{C89S}$ PCR:

Initial PCR was performed using 2 µL purified tail DNA. The longer amplification of the nested PCR reaction was performed using the Tyr-Long_F/R primer pair listed in TABLE 3. PCR was performed using Biolase DNA polymerase (Bioline) and a final concentration of 2% DMSO. Twenty cycles of PCR were run with 30 second annealing and extension steps and an annealing temperature of 66° C. Nested PCR was performed using 2 µL of the initial 25 µL PCR reaction and the Tyr-Short_F/R primer pair listed in TABLE 3. The same PCR conditions were used for the nested PCR as were used for the initial PCR.

TABLE 3

Sequences of PCR primers and expected product sizes. C2RH-Long/Short_F1/R1 primers were used for experiments performed in FIGS. 1A-1E, FIGS. 2A-2E, FIGS. 3A-3G, FIG. 5, FIGS. 7A-7C, FIG. 8, and FIG. 9. In an attempt to further rule out large deletions as a source of apparent heterozygosity, a new genotyping strategy was designed with an initial ~1.3 kb amplimer and used primer sets C2RH-Long/Short_F2/R2 for all other experiments.

| Forward Primer | Sequence | SEQ ID NO: | Reverse Primer | Sequence | SEQ ID NO: | Product Size (bp) |
| --- | --- | --- | --- | --- | --- | --- |
| C2RH-Long_F1 | ACTGACACATGGGAGAAGCC | 10 | C2RH-Long_R1 | TCTCCTTATAACAGGCCAACC | 19 | 429 |
| C2RH-short_F1 | AGTGCCTCACCTCTCACACC | 11 | C2RH-short_R1 | ACTGGCAGAGGGAAAGAAAG | 20 | 266 |
| C2RH-Long_F2 | TCACTGGGTCACAAGCAAAG | 12 | C2RH-Long_R2 | GAAGCAGATGCCCATCTCAG | 21 | 1279 |
| C2RH-Short_F2 | ACTGACACATGGGAGAAGCC | 10 | C2RH-Short_R2 | GATCGAGGAGACTGGCAGAG | 22 | 358 |
| Tyr-Long_F | TCAATTTAGTTACCTCACTATGGGC | 13 | Tyr-Long_R | CAAGTACTCATCTGTGCAAATGTC | 23 | 992 |
| Tyr-Short_F | TTTGGCCATAGGTGCCTG | 14 | Tyr-Short_R | GAGCCTGTGCCTCCTCTAAG | 24 | 411 |
| Shank3-Long_F | AGGAAAGCAAGGTTGAGCTG | 15 | Shank3-Long_R | CTCTGAGGCTTGCAGACGG | 25 | 584 |
| Shank3-Short_F | GAGCTCTACTCCCTTAGGACTT | 16 | Shank3-Short_R | TCCCCCTTTCACTGGACACCC | 26 | 316 |
| Gapdh-Long_F | TACGGGTGCACGTAGCTCAG | 17 | Gapdh-Long_R | CGAAGGACACCAGGCAGTC | 27 | 396 |
| Gapdh-Short_F | TCCCTAGACCCGTACAGTGC | 18 | Gapdh-Short_R | CTCTGCTCCTCCCTGTTCC | 28 | 133 |

Sanger Sequencing:

For all sequencing reactions, 5 µL of PCR product was mixed with 3 µL dH$_2$O and 2 µL ExoSAP (exonuclease 1+shrimp alkaline phosphatase). Products were incubated at 37° C. for 30 minutes to degrade primers and dephosphorylate dNTPs and enzymes were then heat inactivated at 80° C. for 15 minutes. 2.5 µL dH$_2$O and 2.5 µL 10 µM sequencing primer were then added to each mixture and samples were submitted to Genewiz for Sanger sequencing. Sequence analysis was performed using SnapGene. Sequencing primers used were: Chd2-Short_R1, Chd2-Short_F2, and Tyr-Short_F (TABLE 3).

Total Protein Staining and Western Blotting:

1 µg of each recombinant protein was mixed with 2× Laemmli Sample Buffer (Bio-Rad) and heated to 95° C. for 5 minutes. After brief centrifugation, samples were loaded into 4-15% Mini-PROTEAN TGX Pre-Cast gels (Bio-Rad) along with 5 µL PrecisionPlus Protein Kaleidoscope Prestained Protein Standards (Bio-Rad) and run at 200V for 40 minutes in 1× Tris/Glycine/SDS running buffer. Protein was transferred to nitrocellulose at 100V for 1 hour at 4° C. and total protein was visualized using REVERT Total Protein Stain (LI-COR Biosciences) according to the manufacturer's protocol. For RAD51 Western blotting, REVERT Total Protein Stain was reversed according to the manufacturer's protocol, the membrane was blocked at room temperature for 1 hour in TBST containing 5% non-fat dry milk. Primary antibody (Rb anti-RAD51, Abcam ab63801, 1:500) was diluted in blocking buffer and applied to the membrane overnight at 4° C. Following washes with TBST, secondary antibody (IRDye 800CW Gt anti-rabbit IgG H+L, LI-COR 925-32211, 1:15,000) was diluted in blocking buffer and applied to the membrane for 1 hour at room temperature in the dark. The membrane was then washed and imaged. For all experiments, imaging was performed on an Odyssey CLx Imaging System with ImageStudio (LI-COR Biosciences).

In Vitro Cas9 Digestion Assays:

Wildtype or Chd2$^{R1684H/R1684H}$ genomic DNA was used as input for PCR using the conditions described above and the primers specified in FIGS. 10A-10D and FIG. 12. After confirmation of a single band via gel electrophoresis, the PCR reactions were purified using the DNA Clean & Concentrator kit (Zymo) according to the manufacturer's instructions. crRNA and tracrRNA were diluted 1 µM in nuclease-free Duplex Buffer (IDT) and incubated at 95° C. for 5 minutes before being allowed to cool to room temperature on the bench. Digestion mixtures were made in separate tubes by combining nuclease-free water, 10× Cas9 Nuclease Reaction Buffer (final concentration 1×, New England Biolabs), 1 µL of the cooled crRNA/tracrRNA duplex, and, if necessary, 1 µL of EnGen Cas9 NLS, S. pyogenes (New England Biolabs). These mixtures were heated to 37° C. for 10 minutes before adding 250 ng PCR product and, if necessary, RAD51 G151D (10 ng/µL final concentration, custom-produced by Creative Biomart) or BCCIP (10 ng/µL final concentration, Origene TP303061). Digestion was performed at 37° C. for 1 hour, Cas9 was denatured at 95° C., 6× Purple Gel Loading Dye (New England Biolabs) was added to a final concentration of 1×, and the samples were allowed to passively cool to room temperature. After cooling, reactions were separated via electrophoresis with 2% agarose gel, post-stained with Gel-Red Nucleic Acid Gel Stain (Biotium) according to manufacturer's instructions and visualized using an InGenius Gel Documentation System (Syngene).

Genomic qPCR:

To determine copy number at specific genomic loci, a strategy utilizing multiplex nested qPCR was developed. First, multiplex amplification was performed of both the edited Chd2 region and a region of the Gapdh promoter, which is located on a different chromosome, in a short round of PCR (10 cycles). In the case of the Shank3B control experiment, attempts were made to match the input DNA concentration used for experiments utilizing DNA from cultured embryos. Based on an estimation of ~6 pg DNA per cell and a PCR input of ~30 cells, 180 pg Shank3B$^{+/+}$ or Shank3B$^{+/-}$ genomic DNA was used per initial reaction using the Shank3-Long-F/R and Gapdh-Long_F/R primer pairs described in TABLE 3. The PCR products from the initial multiplex PCR was then used as input for nested qPCR using the Shank3-Short_F/R and Gapdh-Short_F/R primer pairs with Sso Advanced SYBR Green Supermix (Bio-Rad). qPCR was performed on a CFX96 Touch Real-Time PCR Detection System (Bio-Rad) and analyzed using CFX Maestro software (Bio-Rad). Shank3B signal was normalized to Gapdh signal to control for input and a second diploid locus. In a second control experiment to test qPCR sensitivity at the Chd2 locus, DNA from wildtype blastocysts was isolated and multiplex PCR was performed for Chd2 using the C2RH-Long_F1/R1 and Gapdh-Long_F/R primer pairs listed in TABLE 3. Genomic qPCR was then performed using the same input amount for Gapdh nested qPCR (Gapdh-Short_F/R primers), but either 1× or 0.5× input for the Chd2 nested qPCR (Chd2-Short_F1/R1 primers). Finally, the same strategy was used to perform nested genomic qPCR using genomic DNA isolated from 5 randomly-selected blastocysts that had genotyped positive for interhomolog repair with no evidence of mosaicism.

Blastomere Collection:

Zygotes were prepared by IVF as described above and cultured until 24hpf in FHM at 37° C. and 5% $CO_2$. Two-cell embryos were transferred 10 at a time into room temperature acidified Tyrode's solution. Embryos were monitored by microscopy and were transferred back to FHM once the zona pellucida was dissolved. Individual blastomeres were collected via mechanical dissociation with a glass micropipette and transferred to 4 µL nuclease-free water. Blastomeres were then lysed and processed for genotyping as previously described.

Immunocytochemistry:

Zygotes were fixed overnight at 4° C. in 4% PFA+0.1% Tween-20 in PBS and then briefly transferred to acidified Tyrode's (Sigma T1788) to remove the zona. After washing in PBS+0.1% Tween-20 (PBST), zygotes were permeabilized in PBS+1% Triton X-100 for 1 hour at 4° C. and then blocked for 1 hour at room temperature in blocking solution (PBS+3% BSA+5% normal goat serum). Primary antibody (rabbit anti-RAD51, Abcam ab63801, 1:500) was diluted in blocking solution and applied to coverslips overnight at 4° C. Cells were washed 3 times in PBST before application of secondary antibody (goat anti-rabbit IgG conjugate, Alexa Fluor 488, ThermoFisher A-11008) diluted in blocking solution for 1 hour at room temperature. Nuclei were counterstained with DAPI and coverslips were mounted to slides with Fluoromount Aqueous Mounting Medium (Sigma F4680). Cells were imaged on an Olympus Fluoview FV1000 confocal microscope with a 60× oil immersion objective and variable digital zoom. Raw image files were exported to FIJI[41] for Z-projection (sum slices), channel splitting, and scale bar generation.

Statistical Analyses:

Statistical analyses were performed using Prism 6 (Graphpad). For chi-square analyses, one-tailed tests were used in analyses of whether a factor could specifically increase interhomolog repair. For all other experiments, two-tailed analyses were performed. Details on statistical tests performed for each experiment are provided in text and figure legends. All graphs display mean±SEM.

Example 1: Efficient Homozygous Knock-in with RAD51

Figure 5:
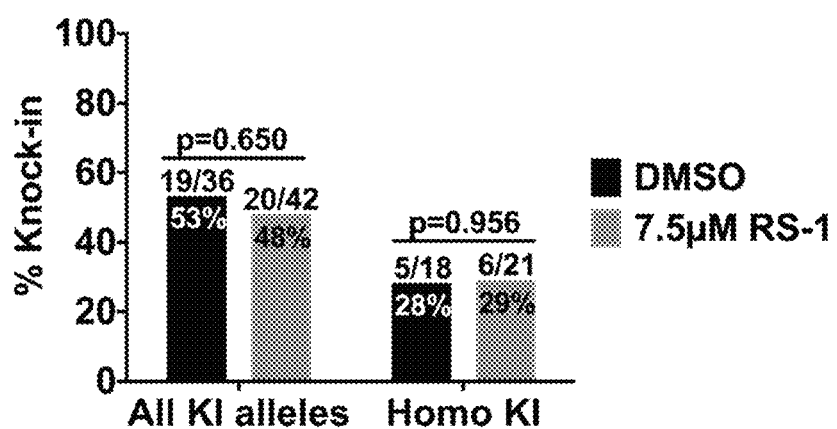
FIG. 5. RS-1 does not alter KI efficiency with ssODNs in mouse zygotes. Chd2$^{R1684H}$ KI and homozygous KI efficiency in embryos cultured in either DMSO or 7.5 µM RS-1 for 24 hours (two-tailed chi-square test).

Experiments were performed to develop a methodology that would generate high-efficiency knock-in of an autism-associated point mutation in Chd2 (c.5051G>A; R1685H in human, R1684H in mouse; hereon referred to as Chd2$^{R1684H}$; FIG. 1A). Previous studies have shown that KI efficiency is affected by the proximity of the Cas9 cut site and the insertion site (Paquet D., et al., Nature. 2016 May 5; 533(7601): 125-9), so a guide was developed so that the cut site was positioned directly adjacent to the desired G>A point mutation. Genotyping of mouse embryos after pronuclear injection and in vitro culture with or without RS-1 (7.5 µM) showed a high KI efficiency at the targeted Chd2 locus; however, inclusion of RS-1 did not improve KI efficiency (FIG. 5).

Because, RS-1 can be highly dosage-sensitive (Song J., et al., Nat. Commun. 2016 Jan. 28; 10548), exogenous RAD51 protein was tested in combination with a three-component CRISPR (Aida T., et al., BMC Genomics. 2016 Nov. 28; 17(1): 979.; Aida T., et al., Genome Biol. 2015 Apr. 29; 16: 87; Quadros R. M., et al., Genome Biol. 2017 May 17; 18(1): 92; Ma X., et al., Sci. Rep. 2017 Feb. 8; 7: 42244). Both pronuclear (PNI) and cytoplasmic (CPI) injections of crRNA, tracrRNA, Cas9, single-strand oligo donor (ssODN; 30 ng/µL for PNI and 100 ng/µL for CPI), and RAD51 protein (10 ng/µL) were performed in mouse zygotes. The resulting $F_0$ pups were genotyped (example chromatograms in FIG. 1B). In 18 pups, an overall KI efficiency of 61.1% and, surprisingly, a homozygous KI efficiency of 55.5% were observed (FIGS. 1C-1D). Because the differences in efficiency between CPI and PNI were not significant (FIG.

6, TABLE 4), PNI was used for the remainder of the experiments described herein.

Although all genotyping was performed using primers designed outside of the homology arms, it is possible that the homozygous animals reported by these genotyping experiments were actually compound heterozygotes—with large deletions emanating from the cut site on one allele (Shin H. Y., et al., Nat. Commun. 2017 May 31; 8: 15464). Therefore, six of the $F_0$ homozygous KI mice were bred with wildtype C57BL/6N animals, and the resulting $F_1$ progeny were genotyped. This revealed that 100% of $F_1$ pups (n=36) were heterozygous mutants and confirmed the homozygosity of $F_0$ animals (FIG. 1E).

TABLE 4

Confirmation of F0 homozygosity. Genotyping results for all F0 pups obtained from either cytoplasmic (CPI) or pronuclear (PNI) injections for Chd2R1684H knock-in experiments described in FIG. 1.

| Sex | Injection Type | Genotype | Notes |
| --- | --- | --- | --- |
| Female | CPI | RH/RH | |
| Female | CPI | RH/Indel | |
| Female | CPI | RH/RH | |
| Male | CPI | RH/RH | |
| Male | CPI | RH/RH | |
| Female | CPI | Indel/Indel | Same Indel |
| Female | CPI | RH/Indel | |
| Female | CPI | RH/RH | |
| Male | CPI | Indel/Indel | Different Indels |
| Female | PNI | RH/RH | |
| Male | PNI | RH/RH | |
| Male | PNI | RH/RH | |
| Female | PNI | Indel/Indel | Different Indels |
| Male | PNI | Indel/Indel | Same Indel |
| Male | PNI | RH/RH | |
| Male | PNI | Indel/Indel | Same Indel |
| Female | PNI | Indel/Indel | Same Indel |
| Female | PNI | RH/RH | |

Example 2: Exogenous RAD51 Enhances KI Efficiency at Multiple Loci

Additional experiments were performed to directly assess the ability of RAD51 to increase KI efficiency. Zygotic pronuclear injections were performed with and without RAD51, embryos were cultured for two days, and nested PCR (~1.3 kb first-round PCR, 358 bp nested) was performed for genotyping. Sanger sequencing revealed that RAD51 only slightly increased overall KI efficiency (FIG. 2A left, p<0.05, one-tailed chi-square test) but drastically increases homozygous KI efficiency (FIG. 2A, right, p<0.0001, one-tailed chi-square test). It is widely accepted that CRISPR/Cas9-mediated editing efficiency can be highly locus- and guide-dependent, so the effects of RAD51 at a second genomic locus was investigated to confirm this efficacy. Using the same injection strategy employed for Chd2, experiments were performed to knock in an albinism-associated human mutation (c.265T>A; C89S; hereon referred to as $Tyr^{C89S}$; schematic in FIG. 2B) in the Tyr gene (Ghodsinejad Kalahroudi V., et al., PLoS ONE. 2014 Sep. 12; 9(9): e106656), which encodes for tyrosinase, the rate-limiting enzyme in melanin production. Albinism is a recessive disorder and, as such, homozygous mutation of Tyr results in mice completely lacking pigment (FIGS. 2C-2D). Injections without RAD51 showed a high overall KI efficiency that was not significantly affected by the addition of RAD51 (FIG. 2E, left). However, the genotyping results again indicated that RAD51 can significantly increase homozygous KI efficiency, with 44.4% of pups exhibiting an albino phenotype resulting from homozygous KI of the $Tyr^{C89S}$ allele with RAD51, as compared to only 12% without (FIG. 2E, right).

Figure 2C:
Figure 2D:
Figure 2E:
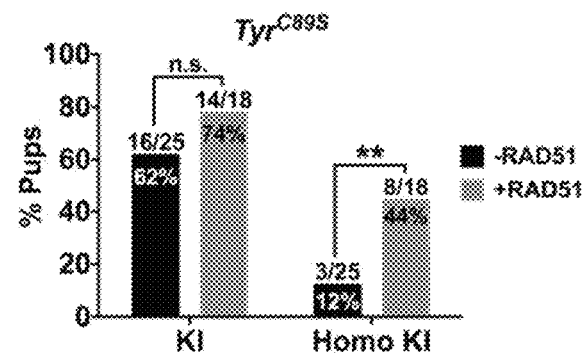
Figure 7A:
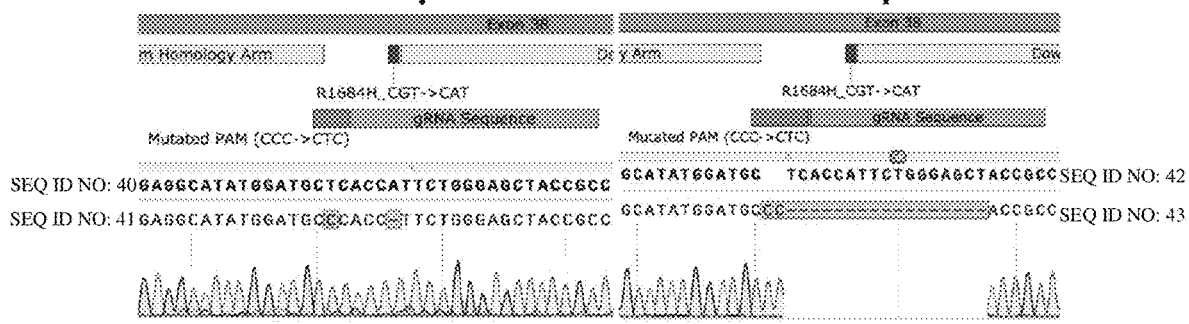
FIGS. 7A-7C. RAD51 stimulates the generation of homozygous indels.
Figure 7B:
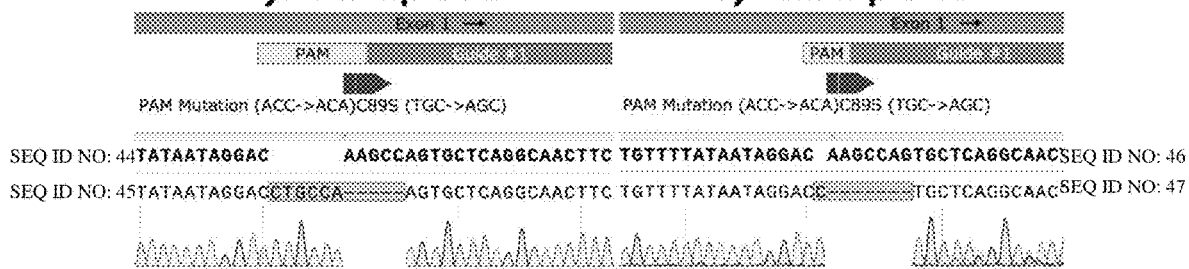
Figure 7C:
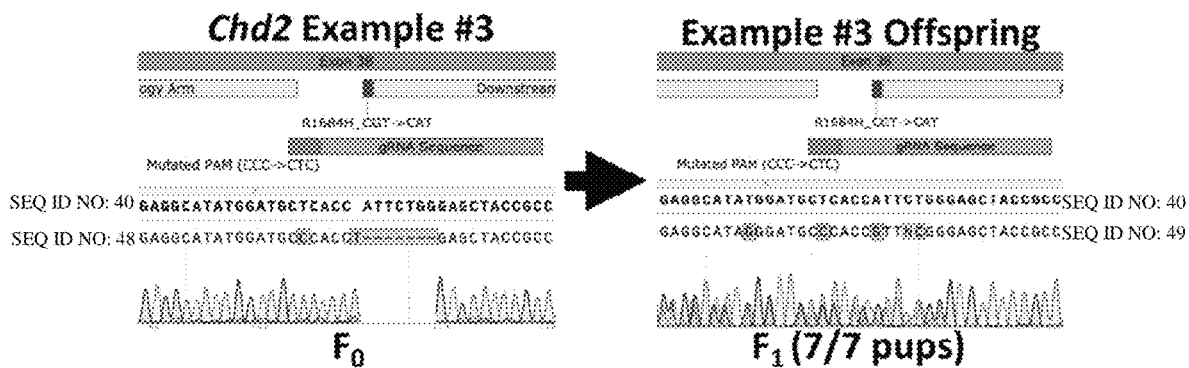
Figure 8:
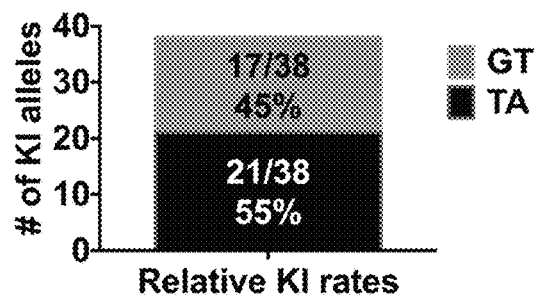
FIG. 8. TA (Chd2$^{R1684H}$) and GT donors show unbiased knock-in efficiencies. Quantification of KI rates observed for the TA (standard Chd2$^{R1684H}$ donor) and GT donors used in FIG. 2D shows no significant difference (two-tailed chi-square test).

Strikingly, RAD51 co-injection more than doubled the observed homozygous KI rate at both the Chd2 and Tyr loci (FIG. 2A and FIG. 2E.). Previous attempts to increase HDR through pharmacological or genetic mechanisms have not shown such high homozygosity rates (Maruyama T., et al., Nat. Biotechnol. 2015 May; 33(5): 538-42; Paquet D., et al., Nature. 2016 May 5; 533(7601): 125-9; Takayama K., et al., Nucleic Acids Res. 2017 May 19; 45(9): 5198-207). The results presented here suggest that RAD51 does not strongly affect overall efficiency of ssODN-mediated knock-in (FIG. 2A and FIG. 2D), suggesting that its effects on homozygosity do not come from directly increasing independent KI events on both alleles. Based on the random nature of insertion-deletions (indels) produced by non-homologous end joining (NHEJ), it was surprising that multiple embryos from both $Chd2^{R1684H}$ and $Tyr^{C89S}$ injections whose genotypes suggested the presence of the same indel on both alleles was observed (FIGS. 7A-7C). Genotyping of $F_1$ pups derived from a female with such a homozygous indel revealed that all pups were heterozygous for the same indel, indicating that the phenomenon was not due to an indel on one allele and a large deletion encompassing the cut site on the other (FIGS. 7A-7C). Although the experimental design could not rule out that these deletions resulted from MMEJ—which can result in stereotyped indels based on local homology (Aida T., et al., BMC Genomics. 2016 Nov. 28; 17(1): 979.4; McVey M. et al., Trends Genet. 2008 November; 24(11): 529-38)—the variety of observed indels suggested that the homozygosity resulted from recombination between homologs that transferred the KI or indel allele from one chromosome to the other.

Example 3: RAD51 Enhances Interchromosomal Homologous Recombination

Previous experiments in mouse ES cells found evidence of interchromosomal homologous recombination/repair (ICHR) events (Moynahan M. E. and Jasin M., Proc. Natl. Acad. Sci. U.S.A. 1997 Aug. 19; 94(17): 8988-93; Richardson C., et al., Genes Dev. 1998 Dec. 15; 12(24): 3831-42). While these ICHR events are well-understood in meiotic cells, their occurrence in zygotes and somatic cells is poorly described. However, several recent studies have described a potential zygotic ICHR mechanism whereby one allele can serve as the repair template for the other after induction of a double-strand break (DSB) by Cas9 (Ma H., et al. Nature. 2017 Aug. 24; 548(7668): 413-19; Wu Y., et al., Cell Stem Cell. 2013 Dec. 5; 13(6): 659-62).

Figure 3A:
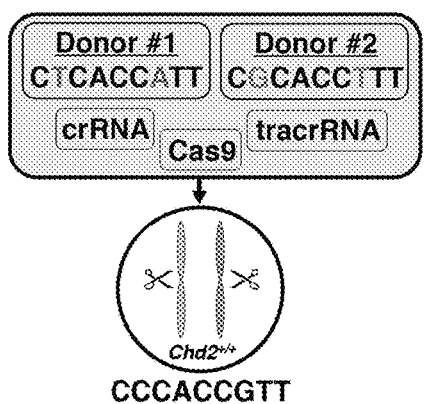
Figure 3B:
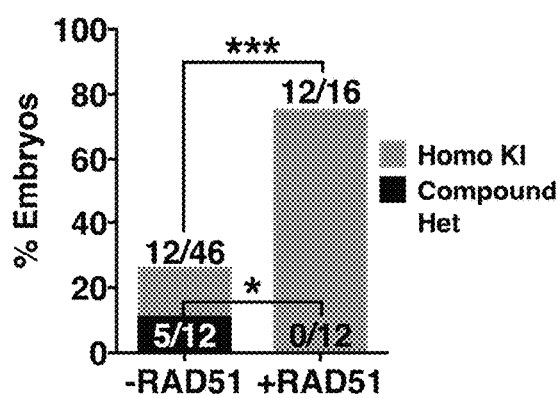

To test whether RAD51 promotes homozygous KI through a similar mechanism, PNI was performed using an injection mixture containing an equimolar ratio of two separate ssODNs containing different point mutations at the same loci, facilitating the identification of independent knock-in events via the observation of compound heterozygosity (FIG. 3A). Like the results seen in FIG. 2A, co-injection of RAD51 significantly increased homozygous KI efficiency (FIG. 3B). Strikingly, compound heterozygosity was observed in 5/12 control embryos with a KI event on both alleles but was not observed in any RAD51-injected embryos (FIG. 3B), supporting the hypothesis that RAD51 increases homozygosity through an enhanced ICHR mechanism. Importantly, no significant differences in overall KI rates between the two ssODNs were observed (FIG. 8), ruling out the possibility that these results were due to a bias toward one donor over the other.

Figure 9:
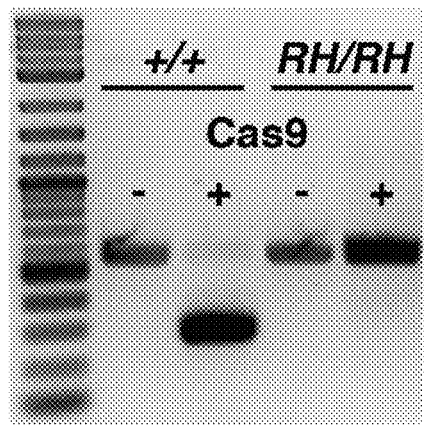
FIG. 9. PCR was performed using the Chd2-RH_F/R primer pair with DNA purified from either wildtype or Chd2$^{R1684H/R1684H}$ mice and the PCR product was used as a template for in vitro digestion assays with or without Cas9.

To more directly test the ICHR mechanism, experiments were performed to generate homozygous Chd2$^{R1684H}$ embryos without the use of an exogenous donor through homozygous conversion. Using wildtype C57Bl/6N eggs and sperm from homozygous Chd2$^{R1684H}$ male mice, heterozygous zygotes were generated by IVF and specifically targeted Cas9 to the maternal Chd2 locus. As illustrated in FIG. 3C, PNI was performed on zygotes at ~8 hours post fertilization (hpf) using a mixture of crRNA, tracrRNA, and Cas9 with or without RAD51. The Chd2$^{R1684H}$ allele contains mutations in both the guide sequence and its associated PAM, and it was confirmed that Cas9 is only capable of cutting the wildtype maternal allele (FIG. 9). By omitting a donor template from the injection mixture it was possible to directly test both the rate of baseline CRISPR/Cas9-mediated ICHR in the zygote and the ability of RAD51 to enhance such a mechanism. In agreement with previous evidence of ICHR in zygotes (Ma H., et al. Nature. 2017 Aug. 24; 548(7668): 413-19), ICHR was observed in 26% of control injected embryos (FIGS. 3D-3E). Strikingly, co-injection of RAD51 was capable of significantly increasing this rate to 74% (FIG. 3E), demonstrating the ability of RAD51 to stimulated high-efficiency ICHR in fertilized mouse zygotes.

Although previous studies have shown that large indels occur at far too low of a frequency to account for the loss-of-heterozygosity observed in these experiments (Shin H. Y., et al., Nat. Commun. 2017 May 31; 8: 15464.), multiple experiments were performed to directly rule out the possibility of false positives resulting from monoallelic deletion of the maternal allele. First, a multiplex genomic qPCR assay was developed and performed to analyze copy number at the targeted locus (see Materials and Methods). Using genomic DNA from wildtype mice and Shank3B$^{+/-}$ mice harboring a heterozygous deletion of exon 13 of Shank3 (Peca J., et al., Nature. 2011 Apr. 28; 472(7344): 437-42), it was confirmed that this method was capable of identifying heterozygous deletions (FIG. 3F). It was also confirmed that PCR targeting the Chd2$^{R1684H}$ locus is sensitive enough to detect changes in copy-number by halving the input DNA (FIG. 3F). Finally, using this genomic qPCR strategy, normal copy-number at the R1684H locus was confirmed in 5/5 randomly selected homozygous mutants (FIG. 3F). Next, F$_0$ Chd2$^{R1684H/R1684H}$ animals were generated via the IVF strategy descried in FIG. 3C (including RAD51). Homozygotes were then crossed with wildtype C57Bl/6N mice to generate F$_1$ animals. Genotyping of the F$_1$ offspring confirmed that 100% were heterozygous for the R1684H mutation (FIG. 3G), supporting the conclusion that all F$_0$ animals were homozygotes produced by ICHR. Taken together, these results show that RAD51 is capable of stimulating highly-efficient ICHR in zygotes.

Example 4: Timing of ICHR

Figure 11A:
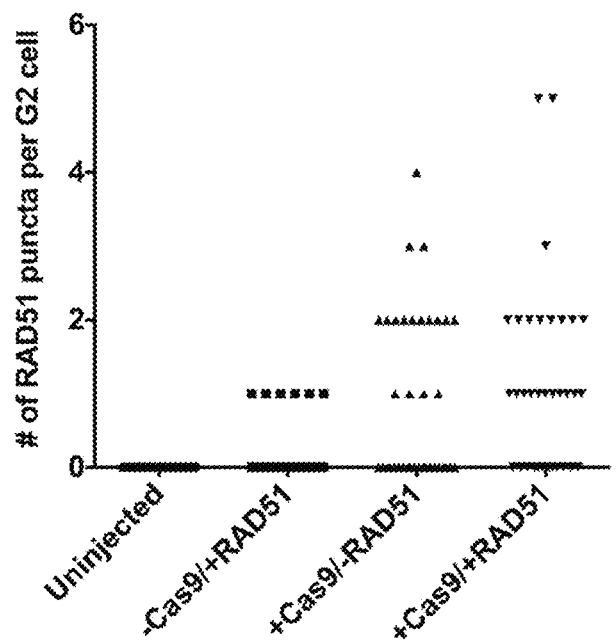
FIGS. 11A-11B. Cas 9 injection alters the number of RAD51 puncta in G2.
Figure 11B:
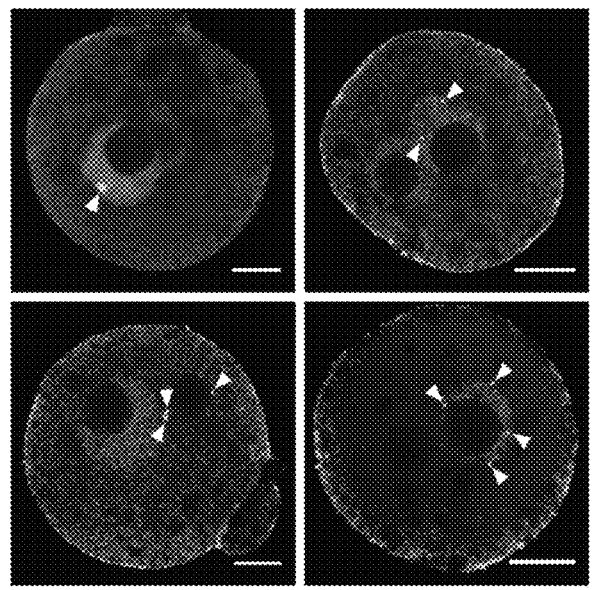

After fertilization, the maternal and paternal pronuclei remain until the completion of S-phase, at which time the pronuclei fuse in preparation for mitosis. This poses a significant problem for ICHR, which requires physical association of the maternal and paternal chromosomes and suggests that ICHR must occur after pronuclear fusion, either during G2 or M-phase. To begin to address the timing of zygotic ICHR, genotyping of individual blastomeres was performed in early 2-cell embryos generated through the IVF strategy and co-injected with RAD51. Blastomeres collected at 24hpf revealed mosaicism in 4/6 of embryos with an ICHR event in at least one cell (FIG. 4A), a finding that supports the chromatogram-based estimations of mosaicism in IVF-based ICHR experiments (FIGS. 10A-10D). Because the blastomeres were collected early in the 2-cell stage, it is unlikely that all observed mosaicism resulted from editing events after the completion of mitosis. Nonetheless, to more directly test the timing of zygotic ICHR, immunocytochemistry (ICC) was performed for RAD51 in uninjected, RAD51-injected, Cas9-injected (with Chd2-targeting crRNA), and Cas9- and RAD51-injected zygotes at three time points: G1 [9 hours post-fertilization (hpf), 1-hour post-injection (hpi)], G2 (14hpf, 6hpf, post S-phase), and M-phase (16hpf, 8hpi). Previous studies have shown that RAD51 staining is weak and/or diffuse in wildtype cells, but that strong RAD51 puncta appear in response to DSBs (Ladstätter S. and Tachibana-Konwalski K., Cell. 2016 Dec. 15; 167(7): 1774-87). In agreement with the genotyping data described above and the hypothesis that ICHR occurs after pronuclear fusion, the appearance of RAD51 puncta was observed solely during G2 (FIGS. 4B-4C). Although RAD51 puncta were not observed in any uninjected G2 embryos, it was surprising that several embryos injected solely with RAD51 exhibited strong foci. The appearance of such events only after S-phase suggests that replication-induced DSBs are not typically repaired through ICHR, but that increased levels of RAD51 can bias the cell toward ICHR. However, embryos injected with Cas9 showed a significantly increased frequency of RAD51 puncta and the highest proportion of positively-stained embryos was observed in the group injected with both Cas9 and RAD51 (FIG. 4B, TABLE 5). Furthermore, RAD51-only embryos only exhibited single RAD51 puncta, but Cas-injected embryos were often observed with 2 or more puncta (FIGS. 11A-11B). Because ICHR occurs after S-phase, Cas9-induced DSBs can occur on the maternal allele and the replicated maternal allele (as well as at Cas9 off-target sites), meaning that cells with 2 or more puncta in Cas-injected cells likely represent those undergoing ICHR with both maternal alleles. Additionally, only single puncta were observed in cells injected solely with RAD51, which supports the hypothesis that these puncta represent the repair of stochastic DSBs. Together, these data support a model whereby RAD51 stimulates ICHR in zygotes during G2, but a deeper understanding of the pathways involved in ICHR is still necessary.

TABLE 5

Chi-square analyses of immunocytochemistry data from FIG. 4B.

| Condition | Positive | Negative | Tot. | p-Value vs. Uninjected | p-Value vs. RAD51-only | p-Value vs. Cas9-only | p-Value vs. Cas9 + Rad51 |
|---|---|---|---|---|---|---|---|
| Uninjected | 0 | 15 | 15 | — | 0.0677 | 0.002 | <0.0001 |
| RAD51-only | 6 | 25 | 31 | 0.0677 | — | 0.016 | 0.0003 |

TABLE 5-continued

Chi-square analyses of immunocytochemistry data from FIG. 4B.

| Condition | Positive | Negative | Tot. | p-Value vs. Uninjected | p-Value vs. RAD51-only | p-Value vs. Cas9-only | p-Value vs. Cas9 + Rad51 |
|---|---|---|---|---|---|---|---|
| Cas9-only | 17 | 22 | 39 | 0.002 | 0.016 | — | 0.0646 |
| Cas9 + RAD51 | 22 | 14 | 36 | <0.001 | 0.0003 | 0.0646 | — |

Example 5: Identification of Additional Proteins Capable of Promoting ICHR

Figure 4D:
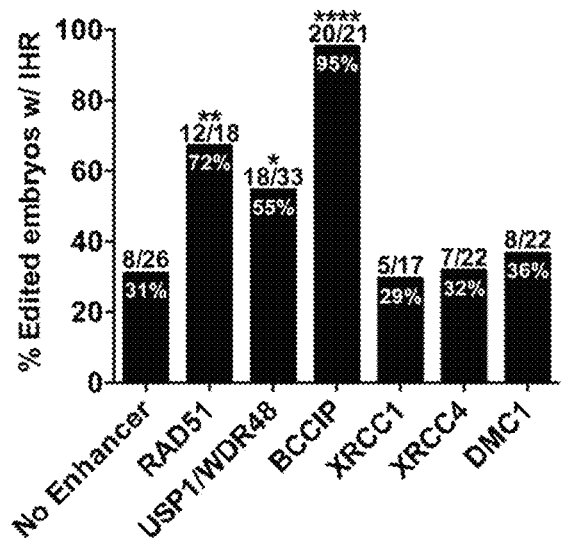

In an effort to identify additional proteins capable of promoting zygotic ICHR, a series of injections in Cas9-injected $Chd2^{+/R1684H}$ zygotes was performed with the following HR- and DSB repair-associated proteins: USP1/WDR48 [promotes HR via Fanconi-Anemia (FA) pathway (Mural J., et al., Mol. Cell Biol. 2011 June; 31(12): 2462-69)], BCCIP (promotes BRCA2-mediated HR (Lu H., et al., Mol. Cell Biol. 2005 May; 25(5): 1949-57; Wray J., et al., Cancer Res. 2008 Apr. 15; 68(8): 2699-707; Kelso A. A., et al., Nucleic Acids Res. 2017 Jan. 25; 45(2): 711-25), participates in FA pathway (Moldovan G. L. and D'Andrea, A. D., Annu. Rev. Genet. 2009; 43: 223-49)), XRCC1 (promotes MMEJ and co-localizes with RAD51 (Taylor R. M., et al., Mol. Cell Biol. 2000 January; 20(2): 735-40; Dutta A., et al., Nucleic Acids Res. 2017 Mar. 17; 45(5): 2585-99)), XRCC4 (promotes NHEJ and regulator of V(D)J recombination (Critchlow S. E., et al., Curr. Biol. 1997 Aug. 1; 7(8): 588-98; Normanno D., et al., Elife. 2017 May 13; 6)), and DMC1 (meiotic HR regulator (Sehorn M. G., et al., Nature. 2004 May 27; 429(6990): 433-37)). XRCC1, XRCC4, and DMC1 were not capable of inducing ICHR at rates above baseline (FIG. 4D). Co-injection of USP1/WDR48, on the other hand, was capable of significant enhancement of ICHR (FIG. 4D). Strikingly, BCCIP exhibited a significantly stronger effect on ICHR rates than USP1/WDR48 (p=0.0014, two-tailed chi-square test), with 95% of edited embryos showing ICHR (FIG. 4D). Since BCCIP-mediated activation of BRCA2 promotes RAD51 activation, these data suggest that proteins capable of directly affecting RAD51 activity are likely to promote high-efficiency ICHR. Additionally, the ability of BCCIP, USP1/WDR48, and RAD51, which are all FA pathway members, to enhance zygotic ICHR implicates the FA pathway in this process.

Example 6: Analyses of RAD51 Mutants

Figure 4E:
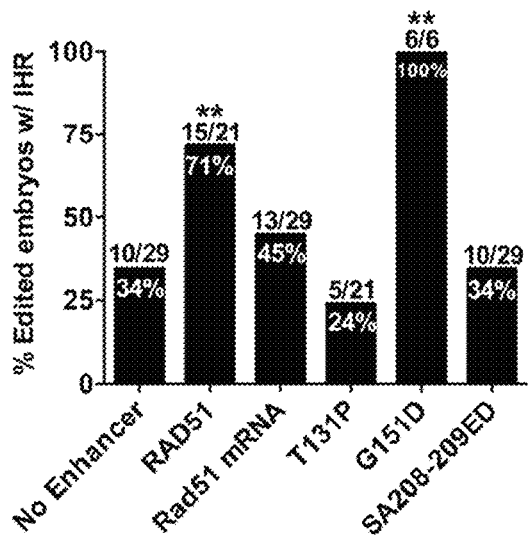
Figure 4F:
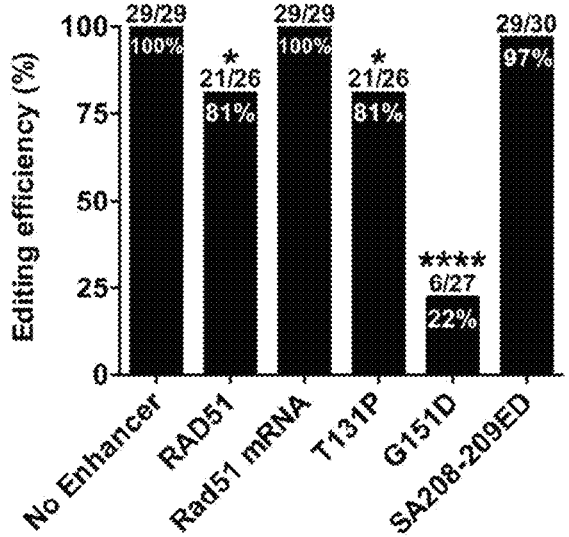
Figure 4G:
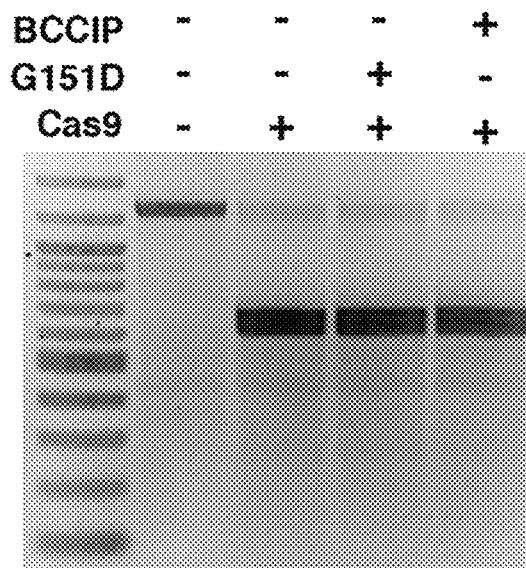
FIG. 4G. In vitro Cas9 nuclease activity assay using a PCR amplimer of the $Chd2^{R1684H}$ locus and Cas9 alone or co-incubated with either RAD51 G151D or BCCIP.
Figure 4H:
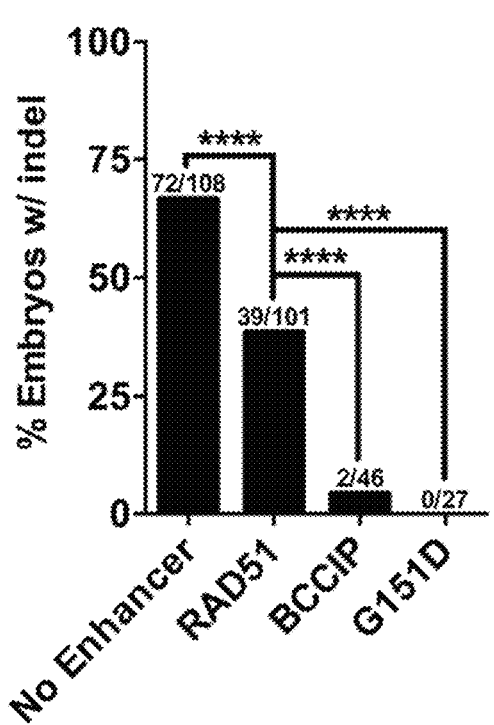
FIG. 4H. Quantification of the percent of total injected embryos carrying an indel after injection with the specified proteins.
Figure 4I:
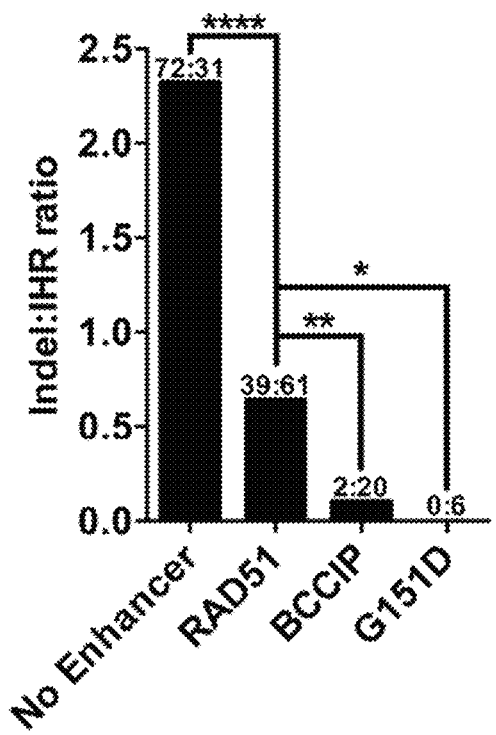
FIG. 4I. Quantification of the ratio of indel-positive embryos to IHR-positive embryos derived from injections with the specified proteins.
Figure 12:
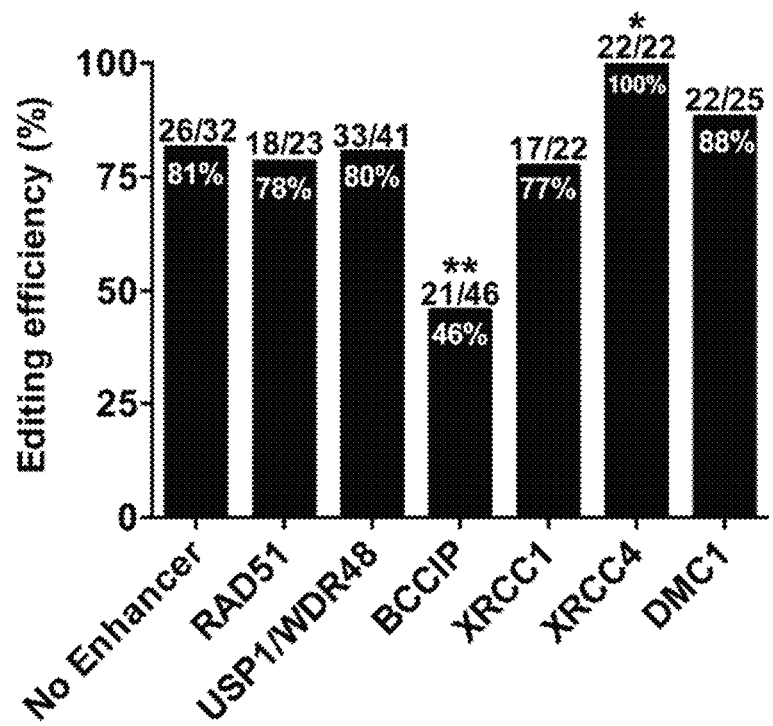
FIG. 12. Decreased editing efficiency in BCCIP-injected cells. Editing efficiency observed in IVF-derived embryos injected with Cas9/crRNA/tracrRNA only (no enhancer) or the indicated HR- and DSB repair-associated proteins (BCCIP: p=0.0016, two-tailed chi-square test; XRCC4: p=0.031, two-tailed chi-square test).
Figure 13A:
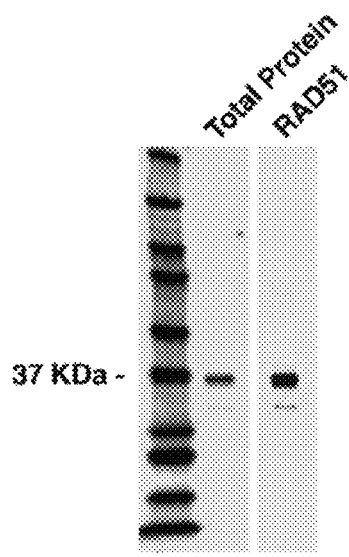
FIGS. 13A-13C. Verification of recombinant protein identity and purity.
Figure 13B:
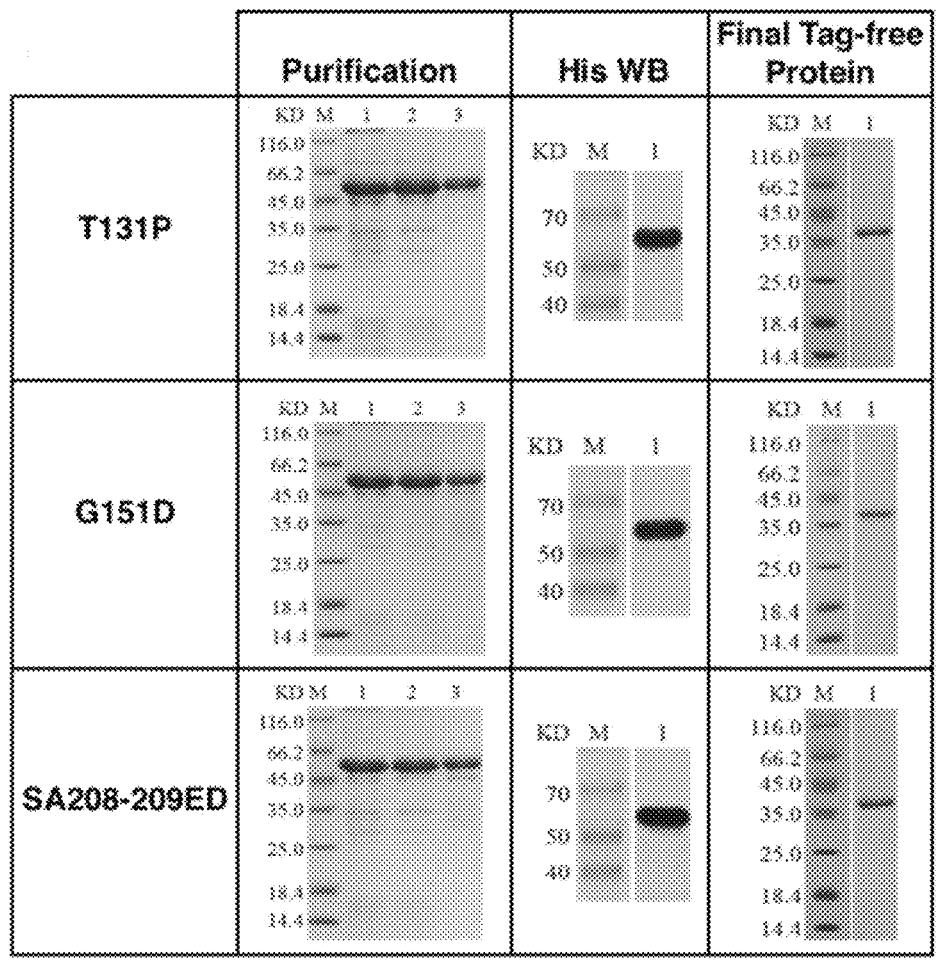
Figure 13C:
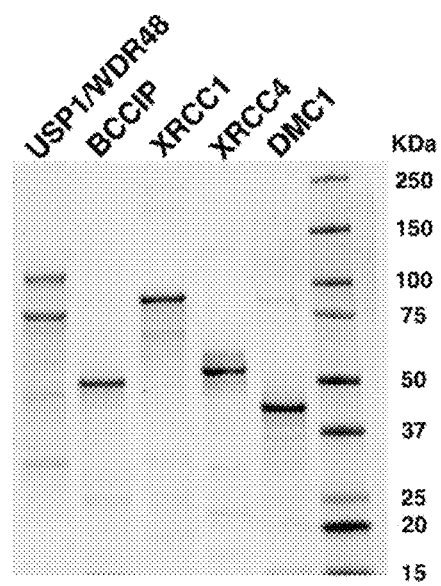

RAD51 mutations have been identified in multiple human cancers and Fanconi-Anemia, and several of these mutations have been studied in-depth. In an effort to better understand the role of RAD51 in ICHR, three different recombinant RAD51 mutant proteins were co-injected with Cas9 and $Chd2^{R1684H}$ crRNA into IVF-generated $Chd2^{R1684H/+}$ embryos. The mutants were as follows: T131P [deficient in interstrand crosslink repair (ICL), but not homologous recombination (HR) (Critchlow S. E., et al., Curr. Biol. 1997 Aug. 1; 7(8): 588-98; Normanno D., et al., Elife. 2017 May 13; 6)], G151D (gain-of-function mutant with increased strand exchange activity (Marsden C. G., PLoS Genet. 2016 Aug. 11; 12(8): e1006208)), and SA208-209ED (disrupted BRCA2-association (Yu D. S., et al., Mol. Cell. 2003 October; 12(4): 1029-41)). T131P injection was not capable of increasing ICHR frequency compared to Cas9-only embryos (FIG. 4E), indicating that RAD51 function associated with ICL repair is required for the induction of ICHR. SA208-209ED also showed unchanged ICHR rates compared to Cas9-only embryos (FIG. 4E), illustrating a requirement for BRCA2 association in RAD51-mediated promotion of ICHR. Surprisingly, in 27 zygotes injected with the RAD51 gain-of-function variant, not a single indel event was identified, and ICHR was observed in all edited cells (FIG. 4E). However, the apparent editing efficiency dropped to 22% (FIG. 4F), suggesting either that G151D either directly inhibits Cas9 nuclease activity or stimulates ICHR at such high levels that the replicated wildtype maternal allele is often used as an ICHR template. To test whether G151D can directly inhibit Cas9 activity, in vitro Cas9 digestion assays were performed with and without co-incubation with G151D and did not observe any direct inhibition of Cas9 activity (FIG. 4G). Interestingly, a similar decrease in editing efficiency was observed with BCCIP-injected embryos that was not due to direct inhibition of Cas9 activity (FIG. 12 and FIG. 4G). Additional analyses of overall indel rates and the indel-to-ICHR ratios in embryos injected with RAD51, BCCIP, or RAD51 G151D revealed a drastic decrease in both rates compared to control embryos (FIG. 4H and FIG. 4I). Furthermore, both BCCIP and RAD51 G151D embryos showed significant decreases in these rates compared to embryos injected with wildtype RAD51. Example 4 demonstrated that ICHR occurs after S-phase in zygotes, when a second wildtype allele is present to serve as an ICHR template. Therefore, this data demonstrates that rather than inhibiting Cas9-mediated DSBs, BCCIP and the RAD51 G151D mutant stimulate ICHR with essentially 100% efficiency and indel-to-ICHR ratios near zero.

Example 7: Discussion

This data demonstrates that RAD51, the BRCA2-interacting protein BCCIP, and the FA pathway-associated protein complex of USP1 and WDR48 are capable of significantly enhancing the rate of zygotic interhomolog repair. Furthermore, this enhancement can be utilized for both donor-free homozygous conversion and de novo homozygous KI using the targeted endonuclease Cas9. Importantly, these results provide the most comprehensive analysis of mammalian zygotic ICHR to-date. While previous work has described the induction of interhomolog repair in zygotes, comprehensive analysis of zygosity and dissection of the underlying mechanisms has been lacking (Egli D., et al., bioRxiv. 2017 Aug. 28; doi:10.1101/181255). This disclosure supports these findings and builds upon them through comprehensive analysis of copy number, identification of pathways involved in zygotic ICHR, visualization of the timing of putative ICHR events, and demonstration of methods for enhancing ICHR for gene editing applications.

Interestingly, this disclosure suggests that the FA pathway may be directly involved in zygotic ICHR. While the FA pathway plays many roles within the cell, its primary function is the repair of DNA interstrand crosslinks (ICLs) (Moldovan G. L. and D'Andrea, A. D., Annu. Rev. Genet.

2009; 43: 223-49). Therefore, the observation that the RAD51 T131P mutant is not capable of enhancing ICHR is intriguing, as this mutant has been shown to function normally in homologous recombination, but not ICL repair (Marsden C. G., et al., PLoS Genet. 2016 Aug. 11; 12(8): e1006208; Yu D. S., et al., Mol. Cell. 2003 October; 12(4): 1029-41). Therefore, these results indicate that ICHR-related proteins may overlap with those involved in ICL and suggest that additional FA pathway members could be capable of enhancing ICHR.

The mechanistic characterization of ICHR in zygotes suggests a model whereby Cas9-induced DSBs are repaired through the use of a homologous chromosome as a template during G2. At this time, the maternal and paternal genomes have already undergone replication and the pronuclei undergo fusion prior to the start of M-phase. This creates a significant hurdle for pure, non-mosaic ICHR, as the cell must now edit two alleles instead of one. This is highlighted by the high degree of mosaicism observed in embryos exhibiting ICHR (FIG. 4A and FIG. 10B), but these experiments do not indicate that any factors other than BCCIP exhibit a strong effect on mosaicism compared to enhancer-free embryos. However, only 1/14 BCCIP-injected embryos with mosaic ICHR was mosaic with an indel (FIG. 10C), suggesting that BCCIP may protect against indels by greatly increasing the probability of ICHR with the replicated wildtype allele or either mutant allele as a template. Together, the mosaicism analyses support the ICC results showing that zygotic ICHR occurs following pronuclear fusion when there are multiple ICHR templates available for repair.

Single-cell RNA-sequencing has shown that Rad51 mRNA is present in zygotes at relatively low levels (FPKM<50) (Deng Q., et al., Science. 2014 Jan. 10; 343 (6167): 193-96). Nonetheless, the existence of endogenous RAD51 in zygotes begs the question of exactly how exogenous RAD51 enhances ICHR. It is possible that increased concentrations of RAD51 in the zygotic pronuclei increase the probability of RAD51 locating and binding to a DSB. Previous work has shown that accumulation of endogenous RAD51 can occur at zygotic DSBs in genetic models of genome instability. Here, RAD51 puncta in uninjected cells was not observed at any stage of the cell cycle. However, injection of RAD51 protein alone revealed a small number of cells with RAD51 puncta (FIG. 4B), suggesting that increasing RAD51 levels is capable of biasing repair of endogenous DSBs toward RAD51-dependent pathways. Furthermore, Rad51 mRNA, which requires time to be translated and therefore provides a graded increase in RAD51 levels in injected zygotes, is only capable of weakly enhancing ICHR (FIG. 4E). The highly-efficient, error-free editing observed in cells injected with the G151D mutant further supports this proximity-based mechanism. Although G151D was injected into cells at the same concentration as wildtype RAD51, the G151D mutant has a higher on-rate for binding to DSBs and binds DSBs more stably due to its increased strand-exchange activity (Marsden C. G., et al., PLoS Genet. 2016 Aug. 11; 12(8): e1006208) and decreased affinity for and hydrolysis of ATP (Chen J., et al., Nucleic Acids Res. 2015 January; 43(2): 1098-111). This could help explain why indels were not observed in these cells, as G151D is likely capable of binding DSBs faster than other DNA repair molecules following Cas9-induced breaks after the completion of S-phase. Therefore, in addition to helping explain the mechanism of RAD51-induced enhancement of zygotic ICHR, these results suggest the potential for highly efficient, error-free ICHR in somatic cells via transient overexpression of the G151D mutant with targeted endonuclease technologies.

In addition to providing a valuable insight into the basic mechanisms of ICHR zygotes, this disclosure's demonstration of enhanced ICHR also has great potential value for therapeutic gene editing. The observation that BCCIP and RAD51 G151D are capable of stimulating essentially error-free (at least in some contexts, error-free) ICHR highlights their potential for the development of safe and effective gene therapies that do not require the use of exogenous DNA as a donor template. In addition to the capability of these proteins to stimulate what is near-100% efficient ICHR, the strikingly low rate of indels observed in cells co-injected with either protein highlights their potential use in safe therapeutic gene editing strategies. Recently developed base editing technologies show promise for the error-free repair of point mutations (Gaudelli N. M., et al., Nature. 2017 Nov. 23; 551(7681): 464-71; Komor A. C., et al., Nature. 2016 May 19; 533(7603): 420-24; 25; Nishida K., Science. 2016 Sep. 16; 353(6305); aaf8729-aaf8729), but similar technologies do not exist for repairing insertions and deletions. Although these studies focused on repairing a single point mutation, Chd2$^{R1684H}$ animals actually harbor two separate point mutations spaced 5 bp apart (FIG. 1A), and conversion of both mutations was observed in 100% of ICHR events. Furthermore, Ma et al. described the repair of a 4 bp deletion in MYBPC3 in human embryos through ICHR (Ma H., Nature. 2017 Aug. 24; 548(7668): 413-9) and previous studies of ICHR in somatic cells demonstrated recombination up to 6 kb from a DSB (Stark J. M. and Jasin M., Mol. Cell Biol. 2003 January; 23(2): 733-43), highlighting the potential for using enhanced ICHR to repair small indels and CNVs with a high degree of accuracy. Importantly, such strategies are not limited to biomedical applications. Therefore, these findings have the potential to develop new approaches to gene therapy, as well as problems in the basic sciences, disease modeling, and biotechnology and suggest that additional studies of endogenous DNA repair pathways are fundamental to the development of new tools and strategies for safe and efficient gene editing.

Example 8: Gene Drive Application

Figure 14A:
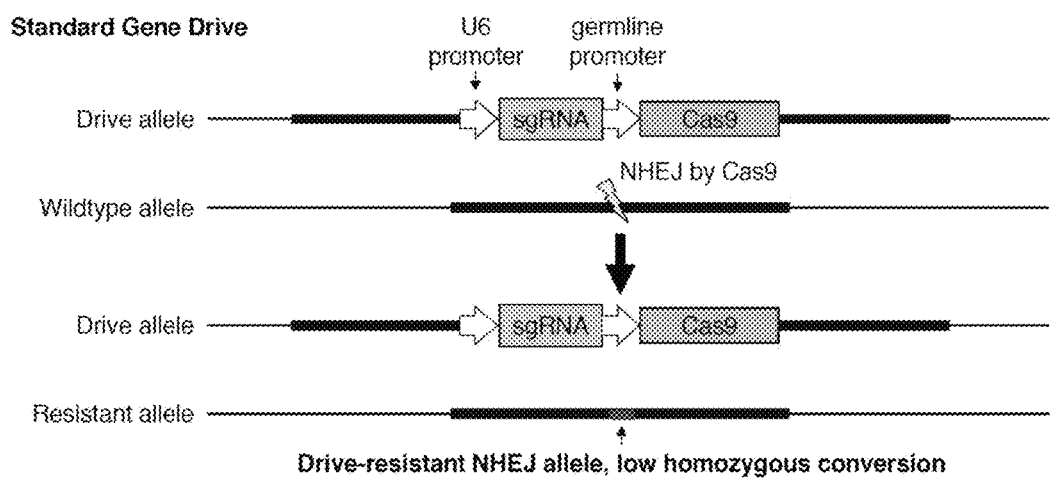
FIGS. 14A-14B. Schematic demonstrating advantages of enhanced ICHR methodologies in gene drive applications over standard gene drive methodologies.
Figure 14B:
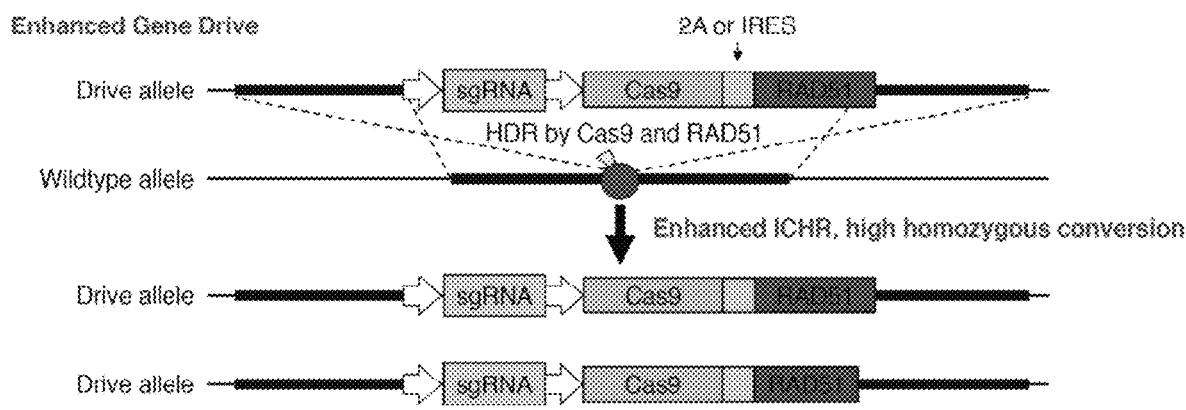

One major application of RAD51 in gene editing is the development of novel gene drive technologies. Current CRISPR-based gene drive strategies rely solely upon CRISPR/Cas9, but these strategies fail to show long-term propagation of the desired allele due to ablation of the guide RNA target site by Cas9-induced indels (FIG. 14A). However, inclusion of RAD51 as an enhancer significantly lessens the chances of this happening by promoting repair from the correctly edited allele, which decreases indel rates at the target site (FIG. 14B).

Example 9: Enhancing Inter-Homolog Recombination in Stem and Somatic Cells for AIDS Treatment and Gene Therapy Recent advances in CRISPR/Cas-based genome editing technologies have provided unprecedented opportunity for preventing and curing human diseases. These technologies can be used to modify genes in particular cell types to lower disease or infection risks and to correct genetic mutations to cure monogenic disorders. Although the CRISPR/Cas system is efficient in disrupting genes through non-homologous end joining (NHEJ), precise repair of genetic mutations (knockin), especially with homozygosity, remains inefficient. Disclosed herein are novel approaches for the enhancement of ICHR. ICHR can convert heterozygous WT/mutant alleles into homozygous mutant alleles without the need for supplying an exogenous repair template and can also convert WT alleles into homozygous mutant alleles with (knockin) or without (knockout) exogenous templates. Thus, this work provides a highly efficient, potentially error-free ICHR method for use in disease prevention and treatment.

One potentially immediate application is for the treatment and prevention of HIV infection. The C—C chemokine receptor type 5 (CCR5) is a co-receptor for HIV infection of white blood cells. 1% Europeans has a homozygous loss-of-function mutation of the gene (CCR5-delta32 mutation), and they are healthy and resistant to HIV infection. The ICHR method can be harnessed to generate hematopoietic stem cells that harbor the homozygous CCR5 mutation in HIV-infected patients. These stem cells can produce HIV-resistant white blood cells, and they can gradually take over the population since they will not be killed by HIV.

Another potential application is to correct genetic mutations in severe monogenic disorders. Most human monogenic disorders are heterozygous. Thus, using the ICHR system, one could effectively use the endogenous normal copy to repair the mutant copy. In addition to the high efficiency of repairing mutations, one significant advantage of ICHR is that in the event of off-target cutting by CRISPR/Cas, it will be effectively repaired from the other normal copy.

Example 10. Enhancement of ICHR in Human Cells

C—C Chemokine Receptor Type 5 (CCR5) is the main co-receptor used by macrophage-tropic strains of HIV-1 and HIV-2, which are responsible for viral transmission. The CCR5 delta 32 mutation (a deletion of 32 base pairs) results in the generation of a premature and non-functional CCR5 receptor. Homozygous CCR5 delta 32 individuals are resistant to CCR5-tropic HIV infection, and heterozygous carriers exhibit slowed AIDS progression (Liu R. et al., Cell. 1996 Aug. 9; 86(3):367-77). Carriers of hetero- and homozygous delta 32 mutations are found in approximately 10% and 1% of the European population, respectfully. HEK293T cells have a heterozygous delta 32 deletion (Qi C. et al., PLoS One. 2016; 11(4): e0152975; Lin Y. C. et al., Nat. Commun. 2014 Sep. 3; 5:4767) (FIG. 15A).

Figure 15A:
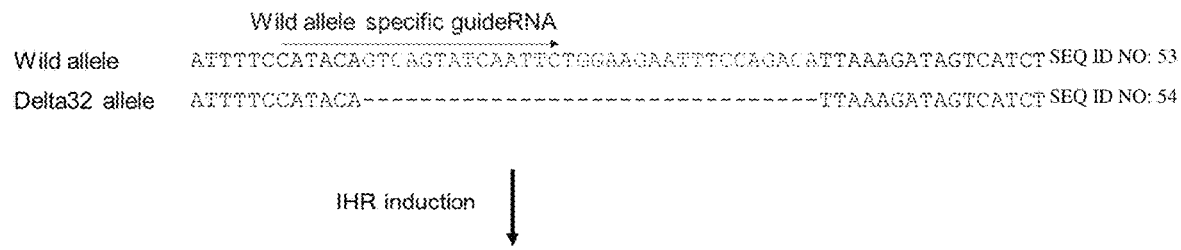
FIGS. 15A-15C. Enhancement of ICHR in human cells.
Figure 15B:
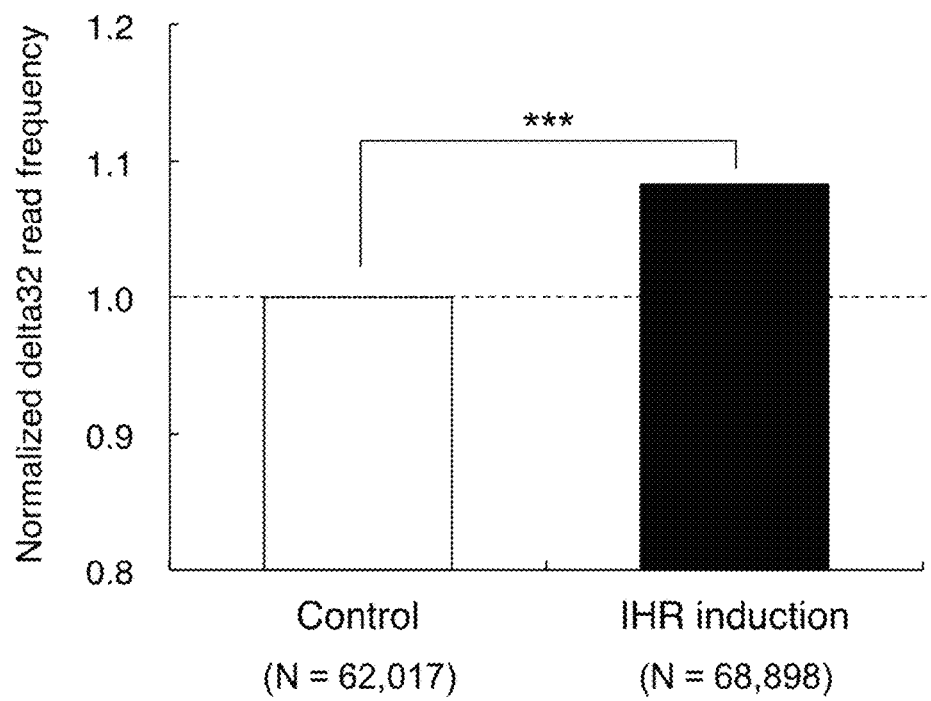
Figure 15C:
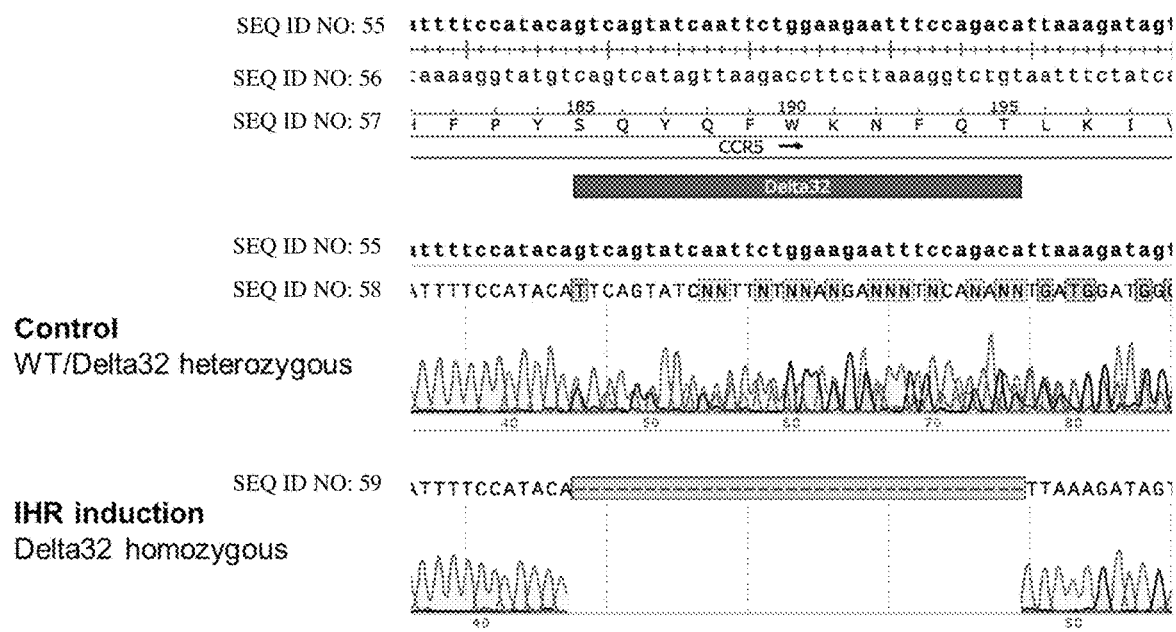

Experiments were designed to assess whether ICHR can be stimulated in human cells (e.g., HEK293T cells) via the enhancement methodologies described herein (FIG. 15A). ICHR enhancement was targeted in HEK293 cells using an sgRNA specific to the wild type CCR5 allele. Delta 32 allele frequency in pooled HEK293T cell populations was measured by deep sequencing. Normalized delta 32 read frequency was elevated when ICHR was stimulated relative to control cells (p<0.001) (FIG. 15B). Sequencing of delta 32 homozygous HEK293T cells clones after ICHR induction demonstrated the conversion of heterozygous HEK293T cells into delta 32 homozygous genotypes (FIG. 15C).

These experiments demonstrate that ICHR can be stimulated in human cells via the enhancement methodologies described herein.

Example 11. ICHR Reporter Mice

Figure 16A:
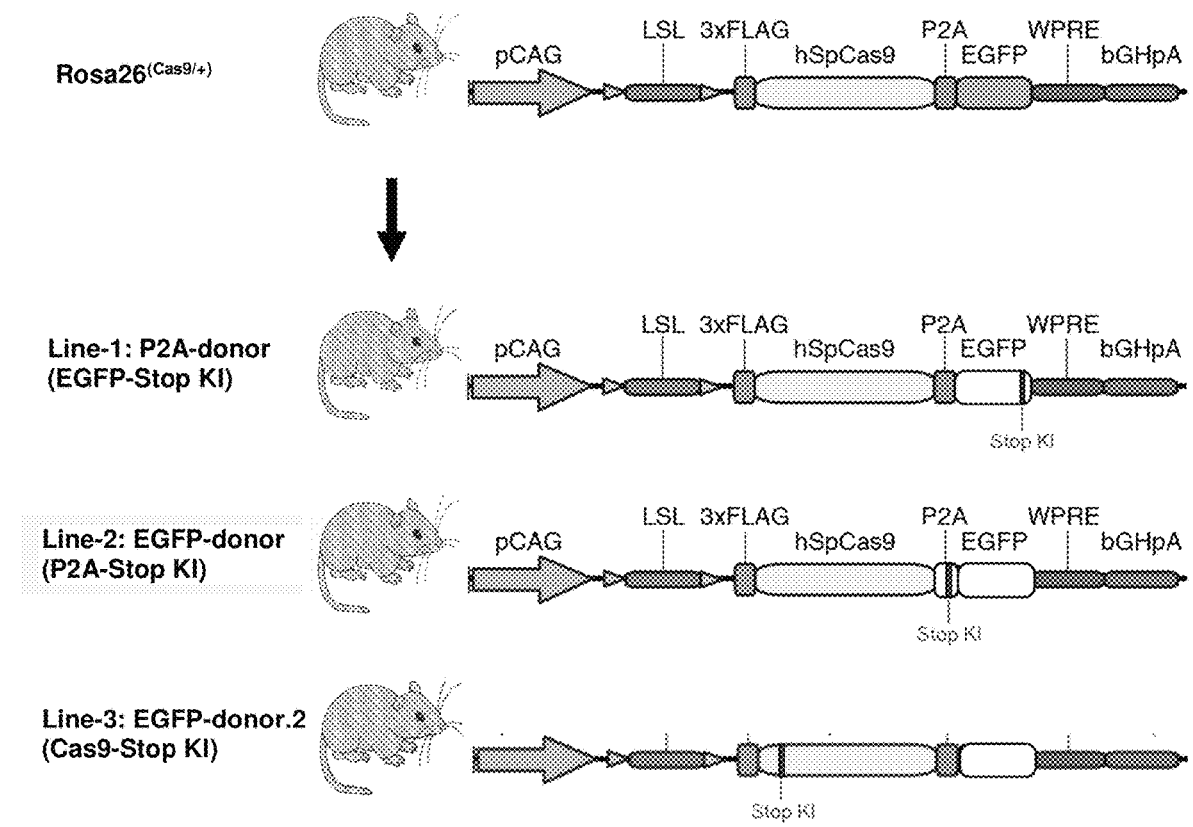
FIGS. 16A-16C. ICHR reporter mice.
Figure 16B:
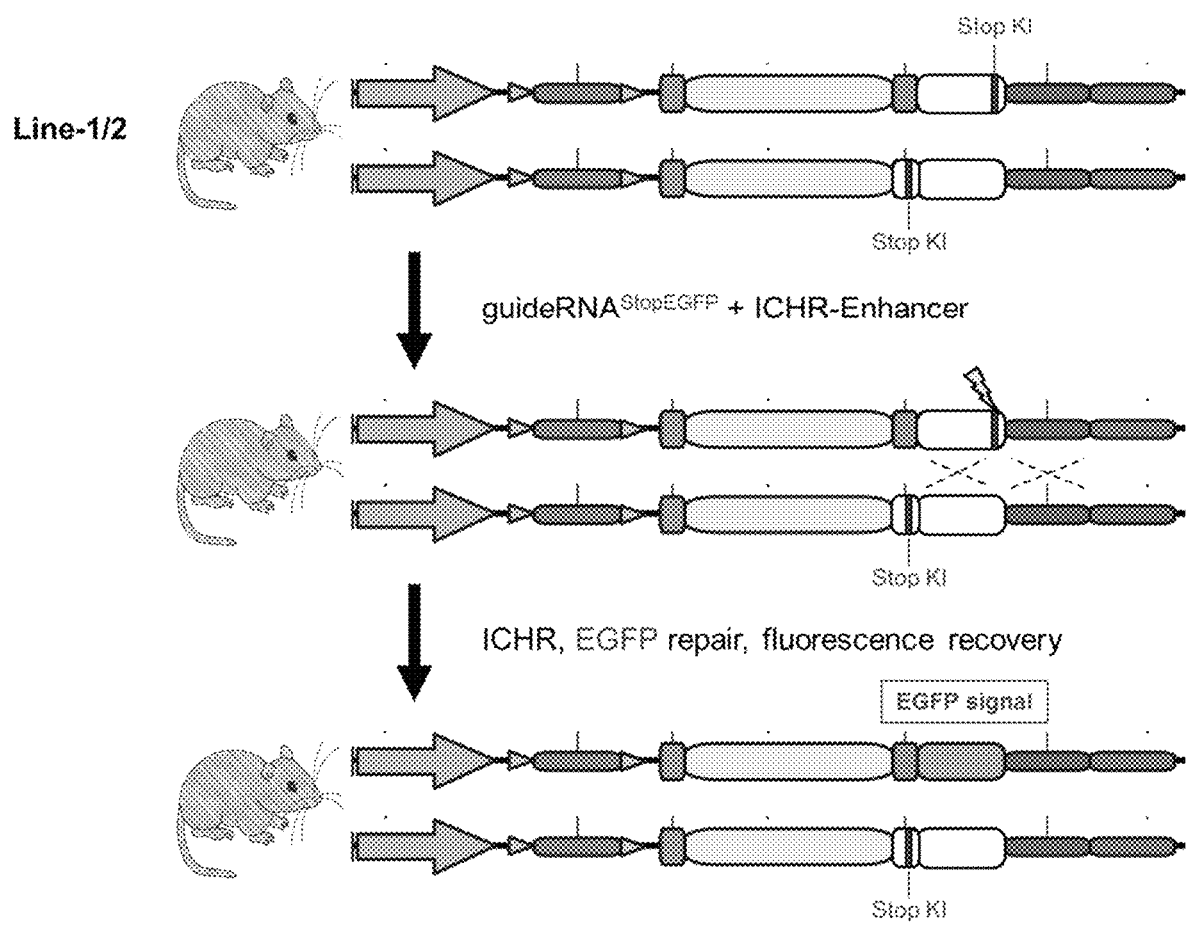
Figure 16C:
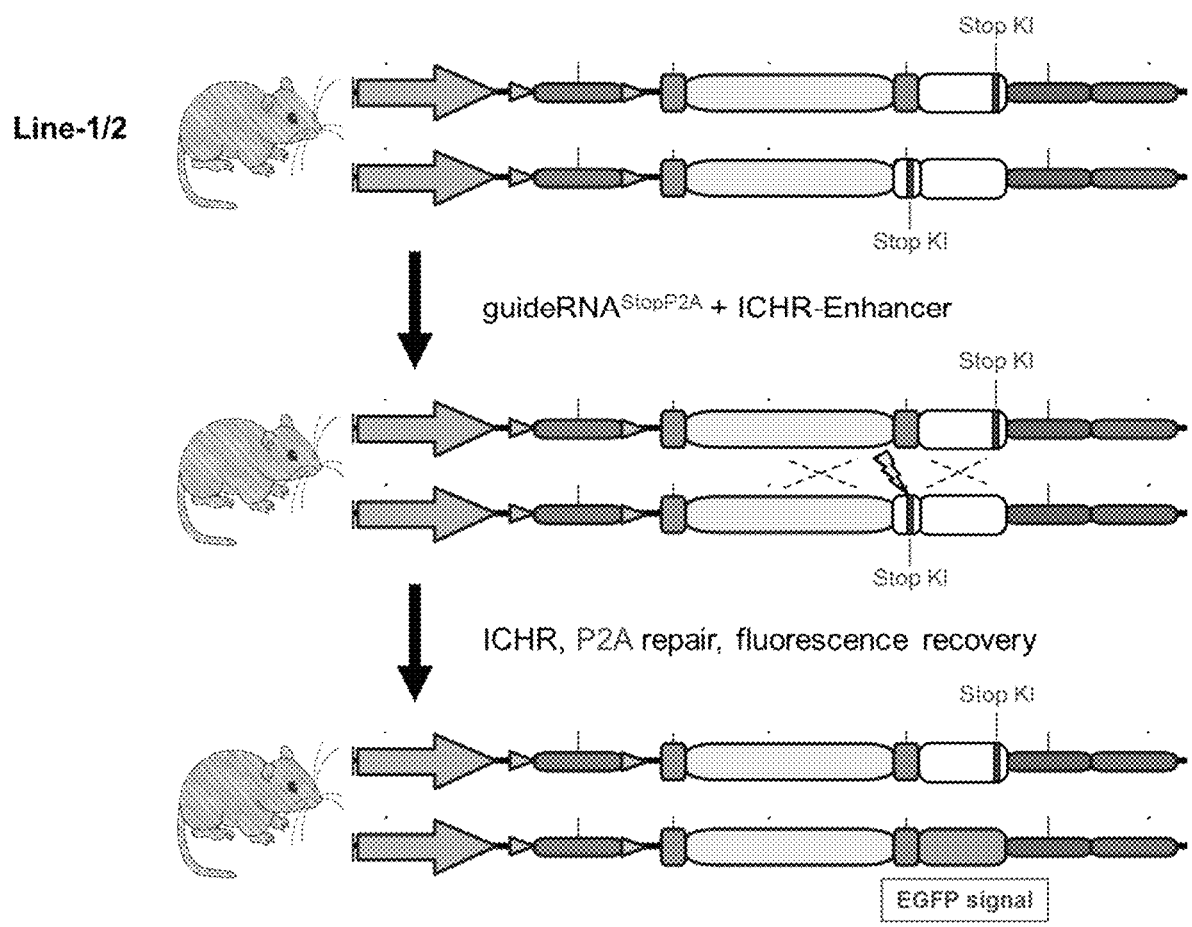
Figures 16D, 16E:
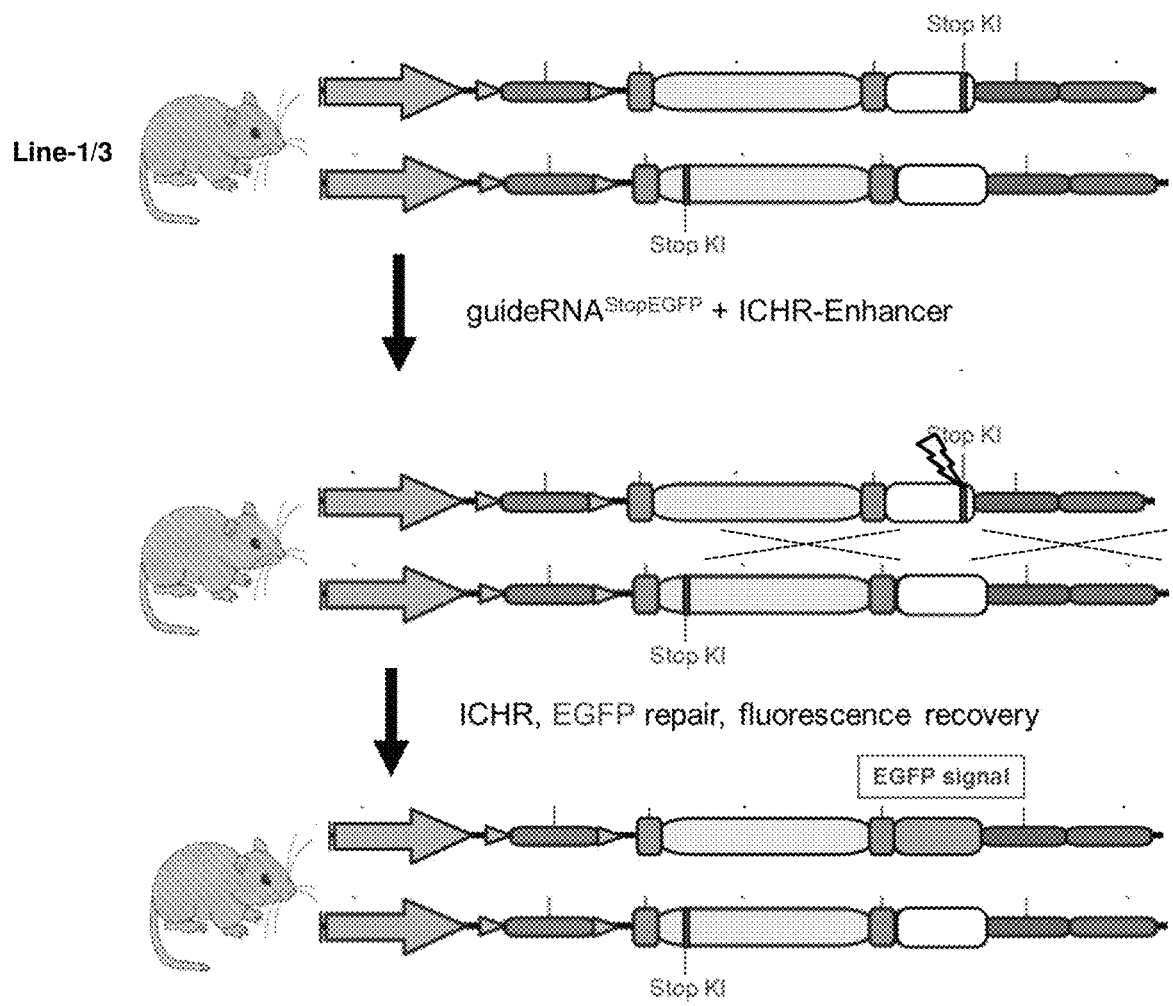
FIG. 16D. Schematic depicting targeted ICHR (i.e., EGFP conversion) in a Line-1/3 transgenic mouse using a guideRNA (i.e., guideRNA$^{StopEGFP}$) directed at the premature stop codon at the 3' end of the nucleic acid sequence of EGFP.
FIG. 16E. Genotyping of transgenic mice. pCAG: CAG promoter; LSL: loxP-stop (33 polyA signal)-loxP; hSpCas9: S. pyogenes Cas9; P2A: self-cleaving P2A peptide; EGPF: enhanced green fluorescent protein; WPRE: woodchuck hepatitis virus (WHP) posttranscriptional regulatory element; bGHpA: human growth hormone polyA sequence.

ICHR reporter mice (Line-1: P2A-donor and Line-2: EGFP-donor) were designed that allow rapid ICHR visualization/identification in vivo in mice of all ages. Two novel mouse lines were generated from the pre-existing Rosa26$^{(Cas9/+)}$ transgenic mouse (Platt R. J. et al., Cell. 2014 Oct. 9; 159(2): 440-55). The Rosa26$^{(Cas9/+)}$ transgene consists of a 33 FLAG-tagged *S. pyogenes* Cas9 linked via a self-cleaving P2A peptide to an enhanced green fluorescent protein (EGFP). The transgene is driven by the ubiquitous CAG promoter and is interrupted by a loxP-stop (33 polyA signal)-loxP (LSL) cassette. For Line-1: P2A-donor, a premature stop codon was introduced at the 3' end of the nucleic acid sequence of EGFP (EGFP-I188X), and for Line-2: EGFP-donor, a premature stop codon was introduced in the nucleic acid sequence of P2A (FIG. 16A). For Line-3: EGFP-donor.2, a premature stop codon was introduced in the nucleic acid sequence of hSpCas9 (D10X). Line-1/2 transgenic mice are generated by crossing Line-1: P2A-donor and Line-2: EGFP-donor mice (FIGS. 16B-16C). Line-1/3 transgenic mice are generated by crossing Line-1: P2A-donor and Line-3: EGFP-donor.2 mice (FIGS. 16D-16E).

EGFP conversion (i.e., EGFP production) can be stimulated in Line-1/2 transgenic mice via two ICHR mechanisms. Conversion may result from an ICHR event that eliminates the premature stop codon at the 3' end of the nucleic acid sequence of EGFP (e.g., using guide RNA$^{StopEGFP}$) (FIG. 16B) or from an ICHR event that eliminates the premature stop codon in the nucleic acid sequence of P2A (e.g., using guideRNA$^{StopP2A}$) (FIG. 16C). Likewise, EGFP conversion (i.e., EGFP production) can be stimulated in Line-1/3 transgenic mice from an ICHR event that eliminates the premature stop codon at the 3' end of the nucleic acid sequence of EGFP (e.g., using guideRNA$^{StopEGFP}$) (FIG. 16D).

These ICHR reporter mice facilitate visualization/identification of ICHR in vivo and can be utilized to evaluate: enhancers of ICHR; ICHR dynamics; and ICHR mosaicism. They can also be used for genome-wide CRISPR screening.

REFERENCES

1. Aida T., Chiyo K., Usami T., Ishikubo H., Imahashi R., Wada Y., Tanaka K. F., Sakuma T., Yamamoto T., and Tanaka K., Cloning-free CRISPR/Cas system facilitates functional cassette knock-in in mice. Genome Biol. 2015 Apr. 29; 16: 87.
2. Aida T., Nakade S., Sakuma T., Izu Y., Oishi A., Mochida K., Ishikubo H., Usami T., Aizawa H., Yamamoto T., and Tanaka K., Gene cassette knock-in in mammalian cells and zygotes by enhanced MMEJ. BMC Genomics. 2016 Nov. 28; 17(1): 979.
3. Chen J., Morrical M. D., Donigan K. A., Weidhaas J. B., Sweasy J. B., Averill A. M., Tomczak J. A., and Morrical S. W., Tumor-associated mutations in a conserved structural motif alter physical and biochemical properties of human RAD51 recombinase. Nucleic Acids Res. 2015 January; 43(2): 1098-111.
4. Critchlow S. E., Bowater R. P., and Jackson S. P., Mammalian DNA double-strand break repair protein XRCC4 interacts with DNA ligase IV. Curr. Biol. 1997 Aug. 1; 7(8): 588-98.
5. Deng Q., Ramskold D., Reinius B., and Sandberg R., Single-cell RNA-seq reveals dynamic, random monoallelic gene expression in mammalian cells. Science. 2014 Jan. 10; 343(6167): 193-96.
6. Dutta A., Eckelmann B., Adhikari S., Ahmed K. M., Sengupta S., Pandey A., Hegde P. M., Tsai M. S., Tainer J. A., Weinfeld M., Hedge M. L., and Mitra S., Microhomology-mediated end joining is activated in irradiated human cells due to phosphorylation-dependent formation of the XRCC1 repair complex. Nucleic Acids Res. 2017 Mar. 17; 45(5): 2585-99.
7. Egli D., Zuccaro M., Kosicki M., Church G., and Bradley A., Inter-homologue repair in fertilized human eggs? bioRxiv. 2017 Aug. 28; doi:10.1101/181255.
8. Gaudelli N. M., Komor A. C., Rees H. A., Packer M. S., Badran A. H., Bryson D. I., and Liu D. R., Programmable base editing of A·T to G·C in genomic DNA without DNA cleavage. Nature. 2017 Nov. 23; 551(7681): 464-71.
9. Ghodsinejad Kalahroudi V., Kamalidehghan B., Arasteh Kani A., Aryani O., Tondar M., Ahmadipour F., Chung L. Y., and Houshmand M., Two novel tyrosinase (TYR) gene mutations with pathogenic impact on oculocutaneous albinism type 1 (OCA1). PLoS ONE. 2014 Sep. 12; 9(9): e106656.
10. Kelso A. A., Goodson S. D., Watts L. E., Ledford L. L., Waldvogel S. M., Diehl J. N., Shah S. B., Say A. F., White J. D., and Sehorn M. G., The β-isoform of BCCIP promotes ADP release from the RAD51 presynaptic filament and enhances homologous DNA pairing. Nucleic Acids Res. 2017 Jan. 25; 45(2): 711-25.
11. Komor A. C., Kim Y. B., Packer M. S., Zuris J. A., and Liu, D. R. Programmable editing of a target base in genomic DNA without double-stranded DNA cleavage. Nature. 2016 May 19; 533(7603): 420-24.
12. Li G., Zhang X., Zhong C., Mo J., Quan R., Yang J., Liu D., Li Z., Yang H., and Wu Z., Small molecules enhance CRISPR/Cas9-mediated homology-directed genome editing in primary cells. Sci. Rep. 2007 Aug. 21; 7(1): 8943.
13. Ladstätter S. and Tachibana-Konwalski K., A Surveillance Mechanism Ensures Repair of DNA Lesions during Zygotic Reprogramming. Cell. 2016 Dec. 15; 167(7): 1774-87.
14. LaRocque J. R., Stark J. M., Oh J., Bojilova E., Yusa K., Horie. K., Takeda J., and Jasin M., Interhomolog recombination and loss of heterozygosity in wild-type and Bloom syndrome helicase (BLM)-deficient mammalian cells. Proc. Natl. Acad. Sci. U.S.A. 2011 Jul. 19; 108(29): 11971-76.
15. Lim D. S. and Hasty P. A mutation in mouse rad51 results in an early embryonic lethal that is suppressed by a mutation in p53. Mol. Cell Biol. 1996 December; 16(12): 7133-43.
16. Lu H., Guo X., Meng X., Liu J., Allen C., Wray J., Nickoloff J. A., and Shen Z., The BRCA2-Interacting Protein BCCIP Functions in RAD51 and BRCA2 Focus Formation and Homologous Recombinational Repair. Mol. Cell Biol. 2005 May; 25(5): 1949-57.
17. Ma H., Marti-Gutierrez N., Park S. W., Wu J., Lee Y., Suzuki K., Koski A., Ji D., Hayama T., Ahmed R., Darby H., Van Dyken C., Li Y., Kang E., Park A. R., Kim D., Kim S. T., Gong J., Gu Y., Xu X., Battaglia D., Krieg S. A., Lee D. M., Wu D. H., Wolf D. P., Heitner S. B., Belmonte J. C. I., Amato P., Kim J. S., Kaul S., and Mitalipov S., Correction of a pathogenic gene mutation in human embryos. Nature. 2017 Aug. 24; 548(7668): 413-9.
18. Ma X., Chen C., Veevers J., Zhou X., Ross R. S., Feng W., and Chen J., CRISPR/Cas9-mediated gene manipulation to create single-amino-acid-substituted and floxed mice with a cloning-free method. Sci. Rep. 2017 Feb. 8; 7: 42244.
19. Marsden C. G., Jensen R. B., Jagelbaum J., Rothenberg E., Morrical S. W., Wallace S. S., and Sweasy J. B., The Tumor-Associated Variant RAD51 G151D Induces a Hyper-Recombination Phenotype. PLoS Genet. 2016 Aug. 11; 12(8): e1006208.
20. Maruyama T., Dougan S. K., Truttman M. C., Bilate A. M., Ingram J. R., and Ploegh H. L., Increasing the efficiency of precise genome editing with CRISPR-Cas9 by inhibition of nonhomologous end joining. Nat. Biotechnol. 2015 May; 33(5): 538-42.
21. McVey M. and Lee S. E., MMEJ repair of double-strand breaks (director's cut): deleted sequences and alternative endings. Trends Genet. 2008 November; 24(11): 529-38.
22. Moldovan G. L. and D'Andrea, A. D., How the fanconi anemia pathway guards the genome. Annu. Rev. Genet. 2009; 43: 223-49.
23. Moynahan M. E. and Jasin M., Loss of heterozygosity induced by a chromosomal double-strand break. Proc. Natl. Acad. Sci. U.S.A. 1997 Aug. 19; 94(17): 8988-93.
24. Murai J., Yang K., Dejsuphong D., Hirota K., Takeda S., and D'Andrea A. D., The USP1/UAF1 complex promotes double-strand break repair through homologous recombination. Mol. Cell Biol. 2011 June; 31(12): 2462-69.
25. Nishida K., Arazoe T., Yachie N., Banno S., Kakimoto M., Tabata M., Mochizuki M., Miyabe A., Araki M., Hara K. Y., Shimatani Z., and Kondo A., Targeted nucleotide editing using hybrid prokaryotic and vertebrate adaptive immune systems. Science. 2016 Sep. 16; 353(6305); aaf8729-aaf8729.
26. Normanno D., Negrel A., de Melo A. J., Betzi S., Meek K., and Modesti M., Mutational phospho-mimicry reveals a regulatory role for the XRCC4 and XLF C-terminal tails in modulating DNA bridging during classical non-homologous end joining. Elife. 2017 May 13; 6.
27. Paquet D., Kwart D., Chen A., Sproul A., Jacob S., Teo S., Olsen K. M., Gregg A., Noggle S., and Tessier-Lavigne M., Efficient introduction of specific homozygous and heterozygous mutations using CRISPR/Cas9. Nature. 2016 May 5; 533(7601): 125-9.
28. Peca J., Feliciano C., Ting J. T., Wang W., Wells M. F., Venkatraman T. N., Lascola C. D., Fu Z., and Feng G., Shank3 mutant mice display autistic-like behaviours and striatal dysfunction. Nature. 2011 Apr. 28; 472(7344): 437-42.
29. Quadros R. M., Miura H., Harms D. W., Akatsuka H., Sato T., Aida T., Redder R., Richardson G. P., Inagaki Y., Sakai D., Buckley S. M., Seshacharyulu P., Batra S. K., Behlke M. A., Zeiner S. A., Jacobi A. M., Izu Y., Thoreson W. B., Urness L. D., Mansour S. L., Ohtsuka M., and Gurumurthy C. B., Easi-CRISPR: a robust method for one-step generation of mice carrying conditional and insertion alleles using long ssDNA donors and CRISPR ribonucleoproteins. Genome Biol. 2017 May 17; 18(1): 92.
30. Richardson C., Moynahan M. E., and Jasin M., Double-strand break repair by interchromosomal recombination: suppression of chromosomal translocations. Genes Dev. 1998 Dec. 15; 12(24): 3831-42.
31. Richardson C. D., Ray G. J., DeWitt M. A., Curie G. L., and Corn J. E., Enhancing homology-directed genome editing by catalytically active and inactive CRISPR-Cas9 using asymmetric donor DNA. Nat. Biotechnol. 2016 March; 34(3): 339-44.
32. Schindelin J. et al., Arganda-Carreras I., Frise E., Kaynig V., Longair M., Pietzsh T., Preibisch S., Rueden C., Saalfeld S., Schmid B., Tinevez J. Y., White D. J., Hartenstein V., Eliceiri K., Tomancak P., and Cardona A., Fiji: an open-source platform for biological-image analysis. Nat. Methods. 2012 Jun. 28; 9(7): 676-82.

33. Schwacha A. and Kleckner N., Interhomolog bias during meiotic recombination: meiotic functions promote a highly differentiated interhomolog-only pathway. Cell. 1997 Sep. 19; 90(6): 1123-35.
34. Sehorn M. G., Sigurdsson S., Bussen W., Unger V. M., and Sung P., Human meiotic recombinase Dmc1 promotes ATP-dependent homologous DNA strand exchange. Nature. 2004 May 27; 429(6990): 433-37.
35. Shin H. Y., Wang C., Lee H. K., Yoo K. H., Zeng X., Kuhns T., Yang C. M., Mohr T., Liu C., and Hennighausen L., CRISPR/Cas9 targeting events cause complex deletions and insertions at 17 sites in the mouse genome. Nat. Commun. 2017 May 31; 8: 15464.
36. Song J., Yang D., Xu J., Zhu T., Chen Y. E., and Zhang J., RS-1 enhances CRISPR/Cas9- and TALEN-mediated knock-in efficiency. Nat. Commun. 2016 Jan. 28; 10548.
37. Stark J. M. and Jasin M., Extensive loss of heterozygosity is suppressed during homologous repair of chromosomal breaks. Mol. Cell Biol. 2003 January; 23(2): 733-43.
38. Takayama K., Igai K., Hagihara Y., Hashimoto R., Hanawa M., Sakuma T., Tachibana M., Sakurai F., Yamamoto T., and Mizuguchi H., Highly efficient biallelic genome editing of human ES/iPS cells using a CRISPR/Cas9 or TALEN system. Nucleic Acids Res. 2017 May 19; 45(9): 5198-207.
39. Taylor R. M., Moore D. J., Whitehouse J., Johnson P., and Caldecott K. W., A cell cycle-specific requirement for the XRCC1 BRCT II domain during mammalian DNA strand break repair. Mol. Cell Biol. 2000 January; 20(2): 735-40.
40. Tsuzuki T., Fujii Y., Sakumi K., Tominaga Y., Nakao K., Sekiguchi M., Matsashiro A., Yoshimura Y., and Morita T., Targeted disruption of the Rad51 gene leads to lethality in embryonic mice. Proc. Natl. Acad. Sci. U.S.A. 1996 Jun. 25; 93(13): 6236-40.
41. Wray J., Liu J., Nickoloff J. A., and Shen Z., Distinct RAD51 Associations with RAD52 and BCCIP in Response to DNA Damage and Replication Stress. Cancer Res. 2008 Apr. 15; 68(8): 2699-707.
42. Wu Y., Liang D., Wang Y., Bai M., Tang W., Bao S., Yan Z., Li D., and Li J., Correction of a genetic disease in mouse via use of CRISPR-Cas9. Cell Stem Cell. 2013 Dec. 5; 13(6): 659-62.
43. Yu C., Liu Y., Ma T., Liu K., Xu S., Zhang Y., Liu H., La Russa M., Xie M., Ding S., and Qi L. S., Small molecules enhance CRISPR genome editing in pluripotent stem cells. Cell Stem Cell. 2015 Feb. 5; 16(2): 142-7.
44. Yu D. S., Sonoda E., Takeda S., Huang C. L., Pellegrini L., Blundell T. L., and Venkitaraman A. R., Dynamic control of Rad51 recombinase by self-association and interaction with BRCA2. Mol. Cell. 2003 October; 12(4): 1029-41.
45. Liu R., Paxton W. A., Choe S., Ceradini D., Martin S. R., MacDonald M. E., Stuhlmann H., Koup R. A., and Landau N. R., Homozygous defect in HIV-1 coreceptor accounts for resistance of some multiply-exposed individuals to HIV-1 infection. Cell. 1996 Aug. 9; 86(3):367-77.
46. Qi C., Jia X., Lu L., Ma P., and Wei M., HEK293T Cells are Heterozygous for CCR5 Delta 32 Mutation. PLoS One. 2016 Apr. 4; 11(4): e0152975.
47. Lin Y. C., Boone M., Meuris L., Lemmens I., Van Roy N., Soete A., Reumers J., Moisse M., Plaisance S., Drmanac R., Chen J., Speleman F., Lambrechts D., Ban de Peer Y., Tavernier J., and Callewaert N., Genome dynamics of the human embryonic kidney 293 lineage in response to cell biology manipulations. Nat. Commun. 2014 Sep. 3; 5:4767.
48. Platt R. J., Chen S., Zhou Y., Yim M. J., Swiech L., Kempton H. R., Dahman J. E., Parnas O., Eisenhaure T. M., Jovanic M., Graham D. B., Jhunjhunwala S., Heidenreich M., Xavier R. J., Langer R., Anderson D. G., Hacohen N., Refev A., Feng G., Sharp P. A., and Zhang F., CRISPR-Cas9 knockin mice for genome editing and cancer modeling. Cell. 2014 Oct. 9; 159(2): 440-55.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method of stimulating a loss of heterozygosity at a gene locus of interest in a living cell comprising:
   identifying a gene locus of interest in a living cell, wherein the gene locus of interest comprises a desired allele and an undesired allele; and
   introducing an enzymatic unit into the living cell, wherein the enzymatic unit enhances interchromosomal homologous recombination between the desired allele and the undesired allele of the gene locus of interest and wherein the enzymatic unit comprises:
   an enhancer component comprising Rad51; and
   a target-specific endonuclease component, wherein the target-specific endonuclease component: (I) provides the enzymatic unit with target specificity; and (ii) has or alternatively lacks endonuclease activity.

2. The method of claim 1, wherein the enzymatic unit cleaves the undesired allele of the gene locus of interest and wherein:
   a. the undesired allele of the gene locus of interest is cleaved only once;
   b. the desired allele of the gene locus of interest remains uncleaved;
   c. the interchromosomal homologous recombination generates homozygosity at the gene locus of interest, wherein the gene of interest comprises two desired alleles after interchromosomal homologous recombination; and
   d. exogenous donor DNA is not introduced into the living cell, wherein the exogenous donor DNA comprises a polynucleic acid sequence that is homologous to the gene locus of interest.

3. The method of claim 2, wherein:
   a. the enzymatic unit cleaves the undesired allele of the gene locus of interest through the introduction of a single-strand break; or
   b. the enzymatic unit cleaves the undesired allele of the gene locus of interest through the introduction of a double-strand break.

4. The method of claim 1, wherein the enzymatic unit lacks the ability to cleave DNA; and wherein:
   a. the interchromosomal homologous recombination generates homozygosity at the gene locus of interest, wherein the gene of interest comprises two desired alleles after interchromosomal homologous recombination; and
   b. exogenous donor DNA is not introduced into the living cell, wherein the exogenous donor DNA comprises a poly nucleic acid sequence that is homologous to the gene locus of interest.

5. The method of claim 4, wherein the target-specific endonuclease component specifically binds to the undesired allele of the gene locus of interest.

6. The method of claim 1, wherein;
   a. the enhancer component comprises a poly nucleic acid that encodes for a poly peptide sequence that comprises the polypeptide sequence of Rad51; or
   b. the enhancer component comprises a polypeptide that comprises the polypeptide sequence of Rad51.

7. The method of claim 1, wherein the enhancer component further comprises a small molecule that enhances homologous directed repair.

8. The method of claim 7, wherein the small molecule that enhances homologous directed repair is RS-1.

9. The method of claim 1, wherein the target-specific endonuclease component comprises:
   a. a polynucleic acid that encodes for a polypeptide sequence that comprises the polypeptide sequence of a target-specific endonuclease; or
   b. a polypeptide that comprises the polypeptide sequence of a target-specific endonuclease.

10. The method of claim 9, wherein the target-specific endonuclease is a RNA-dependent endonuclease.

11. The method of claim 10, wherein;
    a. the RNA-dependent endonuclease is a CRISPR/Cas protein;
    b. the enzymatic unit further comprises a crRNA, a tracrRNA, and/or a sgRNA; or
    c. a combination thereof.

12. The method of claim 11, wherein the CRISPR/Cas protein is a mutated CRISPR/Cas protein.

13. The method of claim 12, wherein the mutated CRISPR/Cas protein comprises a mutated nuclease domain and wherein the mutated CRISPR/Cas protein generates single-strand breaks.

14. The method of claim 9, wherein the target-specific endonuclease is a RNA-independent endonuclease.

15. The method of claim 14, wherein the RNA-independent endonuclease is selected from the group consisting of a meganuclease, a zinc-finger nuclease, a transcription activator-like effector nuclease, and a restriction enzyme, optionally wherein the restriction enzyme is a site-specific DNA-nicking enzyme.

16. The method of claim 1, wherein the loss of heterozygosity is enhanced by at least 20% relative to the loss of heterozygosity in the absence of the at least one enhancer component.

17. The method of claim 1, wherein the enhancer component stimulates essentially error-free interchromosomal homologous recombination.

18. The method of claim 1, wherein the living cell is;
    a. a cell of a multicellular organism, wherein the multicellular organism is administered a composition comprising: the at least one enhancer component; the target-specific endonuclease component; and optionally a cellular delivery component; or
    b. a unicellular organism.

19. The method of claim 18, wherein the multicellular organism is a human.

20. The method of claim 19, wherein the human is a patient suffering from a disease, wherein the disease is caused by heterozygosity a gene locus of interest.

21. The method of claim 18 wherein the unicellular organism is a bacteria.

22. The method of claim 1, wherein the living cell is a cell of a genetically engineered transgenic organism and wherein the gene locus of interest comprises a transgenic gene locus, wherein the desired allele of the transgenic gene locus is a transgenic payload gene and the undesired allele of the transgenic gene locus is an endogenous sequence.

23. A therapeutic composition for use in a method of treating a medical condition caused by heterozygosity at an allele of a gene of interest, the composition comprising:
    an enhancer component comprising Rad51;
    a target-specific endonuclease component wherein the target-specific endonuclease component has or alternatively lacks endonuclease activity; and
    optionally a cellular delivery component.

24. The therapeutic composition of claim 23, wherein the medical condition is:
    a. an autosomal dominant disorder; or
    b. caused by codominance or incomplete dominance.

* * * * *

UNITED STATES PATENT AND TRADEMARK OFFICE
CERTIFICATE OF CORRECTION

| | |
|---|---|
| PATENT NO. | : 11,643,670 B2 |
| APPLICATION NO. | : 16/260630 |
| DATED | : May 9, 2023 |
| INVENTOR(S) | : Jonathan Wilde et al. |

It is certified that error appears in the above-identified patent and that said Letters Patent is hereby corrected as shown below:

In the Claims

At Column 67, Claim 4, Line 34:
--…poly nucleic acid sequence…--
Should read:
"…polynucleic acid sequence…"

At Column 67, Claim 6, Lines 41-42:
--…comprises a poly nucleic acid that encodes for a poly peptide sequence…--
Should read:
"…comprises a polynucleic acid that encodes for a polypeptide sequence…"

Signed and Sealed this
Fourteenth Day of May, 2024

Katherine Kelly Vidal
*Director of the United States Patent and Trademark Office*

SEQUENCE LISTING

```
<160> NUMBER OF SEQ ID NOS: 59

<210> SEQ ID NO 1
<211> LENGTH: 69
<212> TYPE: RNA
<213> ORGANISM: Artificial Sequence
<220> FEATURE:
<223> OTHER INFORMATION: Synthetic Polynucleotide

<400> SEQUENCE: 1
aaacagcaua gcaaguuaaa auaaggcuag uccguuauca acuugaaaaa guggcaccga        60
gucggugcu                                                                69

<210> SEQ ID NO 2
<211> LENGTH: 42
<212> TYPE: RNA
<213> ORGANISM: Artificial Sequence
<220> FEATURE:
<223> OTHER INFORMATION: Synthetic Polynucleotide
```

<400> SEQUENCE: 2
gcgguagcuc ccagaacggu guuuuagagc uaugcuguuu ug        42

<210> SEQ ID NO 3
<211> LENGTH: 126
<212> TYPE: DNA
<213> ORGANISM: Artificial Sequence
<220> FEATURE:
<223> OTHER INFORMATION: Synthetic Polynucleotide

<400> SEQUENCE: 3
tcagtatgag cagcattggt ataaggacca ccactatggt gaccggaggc atatggatgc        60
tcaccattct gggagctacc gccctaacaa catgtccaga agaggccgt atgagcagta        120 caacag        126

<210> SEQ ID NO 4
<211> LENGTH: 125
<212> TYPE: DNA
<213> ORGANISM: Artificial Sequence
<220> FEATURE:
<223> OTHER INFORMATION: Synthetic Polynucleotide

<400> SEQUENCE: 4
tcagtatgag cagcattggt ataaggacca ccactatggt gaccggaggc atatggatgc        60
cacctttctg ggagctaccg ccctaacaac atgtccagaa agaggccgta tgagcagtac       120
aacag        125

<210> SEQ ID NO 5
<211> LENGTH: 42
<212> TYPE: RNA
<213> ORGANISM: Artificial Sequence
<220> FEATURE:
<223> OTHER INFORMATION: Synthetic Polynucleotide

<400> SEQUENCE: 5
gaaguugccu gagcacuggc guuuuagagc uaugcuguuu ug        42

<210> SEQ ID NO 6
<211> LENGTH: 122
<212> TYPE: DNA
<213> ORGANISM: Artificial Sequence
<220> FEATURE:
<223> OTHER INFORMATION: Synthetic Polynucleotide

<400> SEQUENCE: 6
gttccccttc aaagggtgg atgaccgtga gtcctggccc tctgtgtttt ataataggac        60
aagccagtgc tcaggcaact tcatgggttt caactgcgga aactgtaagt ttggatttgg       120
gg        122

<210> SEQ ID NO 7
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 7
atggcaatgc agatgcagct tgaagcaaat gcagatactt cagtggaaga agaaagcttt        60
ggcccacaac ccatttcacg gttagagcag tgtggcataa atgccaacga tgtgaagaaa       120

```
ttggaagaag ctggattcca tactgtggag gctgttgcct atgcgccaaa gaaggagcta    180
ataaatatta agggaattag tgaagccaaa gctgataaaa ttctgacgga gtctcgctct    240
gttgccaggc tggagtgcaa tagcgtgatc ttggtctact gcaccctccg cctctcaggt    300
tcaagtgatt ctcctgcctc agcctcccga gtagttggga ctacaggtgg aattgagact    360
ggatctatca cagaaatgtt tggagaattc cgacctggga agacccagat ctgtcatacg    420
ctagctgtca cctgccagct tcccattgac cggggtggag gtgaaggaaa ggccatgtac    480
attgacactg agggtacctt taggccagaa cggctgctgg cagtggctga gaggtatggt    540
ctctctggca gtgatgtcct ggataatgta gcatatgctc gagcgttcaa cacagaccac    600
cagacccagc tcctttatca agcatcagcc atgatggtag aatctaggta tgcactgctt    660
attgtagaca gtgccaccgc cctttacaga acagactact cgggtcgagg tgagctttca    720
gccaggcaga tgcacttggc caggtttctg cggatgcttc tgcgactcgc tgatgagttt    780
ggtgtagcag tggtaatcac taatcaggtg gtagctcaag tggatggagc agcgatgttt    840
gctgctgatc ccaaaaaacc tattggagga aatatcatcg cccatgcatc aacaaccaga    900
ttgtatctga ggaaaggaag agggaaaccc agaatctgca aaatctacga ctctccctgt    960
cttcctgaag ctgaagctat gttcgccatt aatgcagatg gagtgggaga tgccaaagac    1020
tga                                                                  1023

<210> SEQ ID NO 8
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 8
atggcaatgc agatgcagct tgaagcaaat gcagatactt cagtggaaga agaaagcttt    60
ggcccacaac ccatttcacg gttagagcag tgtggcataa atgccaacga tgtgaagaaa    120
ttggaagaag ctggattcca tactgtggag gctgttgcct atgcgccaaa gaaggagcta    180
ataaatatta agggaattag tgaagccaaa gctgataaaa ttctgacgga gtctcgctct    240
gttgccaggc tggagtgcaa tagcgtgatc ttggtctact gcaccctccg cctctcaggt    300
tcaagtgatt ctcctgcctc agcctcccga gtagttggga ctacaggtgg aattgagact    360
ggatctatca cagaaatgtt tggagaattc gaactgggaa agacccagat ctgtcatacg    420
ctagctgtca cctgccagct tcccattgac cgggatggag gtgaaggaaa ggccatgtac    480
attgacactg agggtacctt taggccagaa cggctgctgg cagtggctga gaggtatggt    540
ctctctggca gtgatgtcct ggataatgta gcatatgctc gagcgttcaa cacagaccac    600
cagacccagc tcctttatca agcatcagcc atgatggtag aatctaggta tgcactgctt    660
attgtagaca gtgccaccgc cctttacaga acagactact cgggtcgagg tgagctttca    720
gccaggcaga tgcacttggc caggtttctg cggatgcttc tgcgactcgc tgatgagttt    780
ggtgtagcag tggtaatcac taatcaggtg gtagctcaag tggatggagc agcgatgttt    840
gctgctgatc ccaaaaaacc tattggagga aatatcatcg cccatgcatc aacaaccaga    900
ttgtatctga ggaaaggaag agggaaaccc agaatctgca aaatctacga ctctccctgt    960
cttcctgaag ctgaagctat gttcgccatt aatgcagatg gagtgggaga tgccaaagac    1020
tga                                                                  1023
```

```
<210> SEQ ID NO 9
<211> LENGTH: 1023
<212> TYPE: DNA
<213> ORGANISM: Artificial Sequence
<220> FEATURE:
<223> OTHER INFORMATION: Synthetic Polynucleotide

<400> SEQUENCE: 9
atggcaatgc agatgcagct tgaagcaaat gcagatactt cagtggaaga agaaagcttt      60
ggcccacaac ccatttcacg gttagagcag tgtggcataa atgccaacga tgtgaagaaa     120
ttggaagaag ctggattcca tactgtggag gctgttgcct atgcgccaaa gaaggagcta     180
ataaatatta agggaattag tgaagccaaa gctgataaaa ttctgacgga gtctcgctct     240
gttgccaggc tggagtgcaa tagcgtgatc ttggtctact gcaccctccg cctctcaggt     300
tcaagtgatt ctcctgcctc agcctcccga gtagttggga ctacaggtgg aattgagact     360
ggatctatca cagaaatgtt tggagaattc gaactgggaa gacccagat ctgtcatacg      420
ctagctgtca cctgccagct tcccattgac cggggtggag gtgaaggaaa ggccatgtac     480
attgacactg agggtacctt taggccagaa cggctgctgg cagtggctga gaggtatggt     540
ctctctggca gtgatgtcct ggataatgta gcatatgctc gagcgttcaa cacagaccac     600
cagacccagc tcctttatca agcagaagac atgatggtag aatctaggta tgcactgctt     660
attgtagaca gtgccaccgc cctttacaga acagactact cgggtcgagg tgagctttca     720
gccaggcaga tgcacttggc caggtttctg cggatgcttc tgcgactcgc tgatgagttt     780
ggtgtagcag tggtaatcac taatcaggtg gtagctcaag tggatggagc agcgatgttt     840
gctgctgatc caaaaaacc tattggagga aatatcatcg cccatgcatc aacaaccaga      900
ttgtatctga ggaaaggaag aggggaaacc agaatctgca aaatctacga ctctccctgt     960
cttcctgaag ctgaagctat gttcgccatt aatgcagatg gagtgggaga tgccaaagac    1020
tga                                                                  1023

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
actgacacat gggagaagcc                                                   20

<210> SEQ ID NO 11
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 11
agtgcctcac ctctcacacc                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide
```

```
<400> SEQUENCE: 12
tcactgggtc acaagcaaag                                               20

<210> SEQ ID NO 13
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 13
tcaatttagt tacctcacta tgggc                                         25

<210> SEQ ID NO 14
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 14
tttggccata ggtgcctg                                                 18

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
aggaaagcaa ggttgagctg                                               20

<210> SEQ ID NO 16
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 16
gagctctact cccttaggac tt                                            22

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
tacgggtgca cgtagctcag                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
tccctagacc cgtacagtgc                                               20

<210> SEQ ID NO 19
```

```
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 19
tctccttata acaggccaac c                                            21

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 20
actggcagag ggaaagaaag                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 21
gaagcagatg cccatctcag                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 22
gatcgaggag actggcagag                                              20

<210> SEQ ID NO 23
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 23
caagtactca tctgtgcaaa tgtc                                         24

<210> SEQ ID NO 24
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 24
gagcctgtgc ctcctctaag                                              20

<210> SEQ ID NO 25
<211> LENGTH: 19
<212> TYPE: DNA
<213> ORGANISM: Artificial Sequence
<220> FEATURE:
<223> OTHER INFORMATION: Synthetic Polynucleotide
```

```
<400> SEQUENCE: 25
ctctgaggct tgcagacgg                                                    19

<210> SEQ ID NO 26
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 26
tccccctttc actggacacc c                                                 21

<210> SEQ ID NO 27
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 27
cgaaggacac caggcagtc                                                    19

<210> SEQ ID NO 28
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 28
ctctgctcct ccctgttcc                                                    19

<210> SEQ ID NO 29
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 29
tcagtatgac atatggatgc ccaccgttct gggagctacc gccctaacaa cgtacaacag       60

<210> SEQ ID NO 30
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa may be His or Arg

<400> SEQUENCE: 30

His Met Asn Ala His Xaa Ser Gly Ser Tyr Arg Pro Asn Asn
1               5                   10

<210> SEQ ID NO 31
<211> LENGTH: 60
<212> TYPE: DNA
<213> ORGANISM: Artificial Sequence
<220> FEATURE:
<223> OTHER INFORMATION: Synthetic Polynucleotide
```

-continued

<400> SEQUENCE: 31
tcagtatgac atatggatgc tcaccattct gggagctacc gccctaacaa cgtacaacag    60

<210> SEQ ID NO 32
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 32
tgcccaccgt tc    12

<210> SEQ ID NO 33
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 33
tgctcaccat tc    12

<210> SEQ ID NO 34
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 34
acctgccagt gctcaggcaa cttc    24

<210> SEQ ID NO 35
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(2)
<223> OTHER INFORMATION: Xaa may be Cys or Ser

<400> SEQUENCE: 35

Thr Xaa Gln Cys Ser Gly Asn Phe
1               5

<210> SEQ ID NO 36
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 36
acaagccagt gctcaggcaa cttc    24

<210> SEQ ID NO 37
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 37
gatgcccacc gttctg                                                           16

<210> SEQ ID NO 38
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 38
gatgcycacc rttctg                                                           16

<210> SEQ ID NO 39
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 39
gatgctcacc attctg                                                           16

<210> SEQ ID NO 40
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 40
gaggcatatg gatgctcacc attctgggag ctaccgcc                                   38

<210> SEQ ID NO 41
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 41
gaggcatatg gatgcccacc ttctgggagc taccgcc                                    37

<210> SEQ ID NO 42
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 42
gcatatggat gctcaccatt ctgggagcta ccgcc                                      35

<210> SEQ ID NO 43
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 43
gcatatggat gcccaccgcc                                                       20

<210> SEQ ID NO 44

```
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 44
tataatagga caagccagtg ctcaggcaac ttc                              33

<210> SEQ ID NO 45
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 45
tataatagga cctgccaagt gctcaggcaa cttc                             34

<210> SEQ ID NO 46
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 46
tgttttataa taggacaagc cagtgctcag gcaac                            35

<210> SEQ ID NO 47
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 47
tgttttataa taggacctgc tcaggcaac                                   29

<210> SEQ ID NO 48
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 48
gaggcatatg gatgcccacc tgagctaccg cc                               32

<210> SEQ ID NO 49
<211> LENGTH: 38
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (24)..(24)
<223> OTHER INFORMATION: n is a, c, g, or t

<400> SEQUENCE: 49
gaggcatagg gatgcccacc gttncgggag ctaccgcc                         38

<210> SEQ ID NO 50
<211> LENGTH: 10
<212> TYPE: DNA
<213> ORGANISM: Artificial Sequence
```

```
<220> FEATURE:
<223> OTHER INFORMATION: Synthetic Polynucleotide

<400> SEQUENCE: 50
gcccaccgtt                                                                10

<210> SEQ ID NO 51
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 51
gcccaccatt                                                                10

<210> SEQ ID NO 52
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 52
gctcaccatt                                                                10

<210> SEQ ID NO 53
<211> LENGTH: 60
<212> TYPE: DNA
<213> ORGANISM: Homo sapiens

<400> SEQUENCE: 53
attttccata cagtcagtat caattctgga agaatttcca gacattaaag atagtcatct         60

<210> SEQ ID NO 54
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 54
attttccata cattaaagat agtcatct                                            28

<210> SEQ ID NO 55
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 55
atttccatac agtcagtatc aattctggaa gaatttccag acattaaaga tagt              54

<210> SEQ ID NO 56
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 56
caaaaggtat gtcagtcata gttaagacct tcttaaaggt ctgtaatttc tatca             55

<210> SEQ ID NO 57
```

```
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 57

His Phe Pro Tyr Ser Gln Tyr Gln Phe Trp Lys Asn Phe Gln Thr Leu
1               5                   10                  15

Lys Ile Val

<210> SEQ ID NO 58
<211> LENGTH: 55
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 58
attttccata cattcagtat cnnttntnna ngannntnca nanntgatgg atggt        55

<210> SEQ ID NO 59
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 59
attttccata cattaaagat agt                                           23
```